US012642854B2

(12) United States Patent
Gunbas et al.

(10) Patent No.: US 12,642,854 B2
(45) Date of Patent: Jun. 2, 2026

(54) NEAR-INFRARED (NIR) ABSORBING PHOTOSENSITIZERS

(71) Applicants: ORTA DOGU TEKNIK UNIVERSITESI, Ankara (TR); KOC UNIVERSITESI, Istanbul (TR)

(72) Inventors: Gorkem Gunbas, Ankara (TR); Safacan Kolemen, Istanbul (TR); Osman Karaman, Ankara (TR); Gizem Atakan, Ankara (TR); Toghrul Almammadov, Istanbul (TR)

(73) Assignees: ORTA DOGU TEKNIK UNIVERSITESI, Ankara (TR); KOC UNIVERSITESI, Istanbul (TR)

( * ) Notice: Subject to any disclaimer, the term of this patent is extended or adjusted under 35 U.S.C. 154(b) by 0 days.

(21) Appl. No.: 18/669,670

(22) Filed: May 21, 2024

(65) Prior Publication Data

US 2024/0342286 A1 Oct. 17, 2024

Related U.S. Application Data

(62) Division of application No. 16/973,435, filed as application No. PCT/TR2018/050322 on Jun. 25, 2018, now abandoned.

(51) Int. Cl.

| | |
|---|---|
| ***A61K 41/00*** | (2020.01) |
| ***C07F 5/02*** | (2006.01) |
| ***C07F 7/08*** | (2006.01) |

(52) U.S. Cl.

CPC .......... *A61K 41/0057* (2013.01); *C07F 5/022* (2013.01); *C07F 7/0814* (2013.01)

(58) Field of Classification Search

CPC .... C07F 7/0816; C07F 9/6584; C07F 7/0814; A61K 41/0057

See application file for complete search history.

(56) References Cited

FOREIGN PATENT DOCUMENTS

| | | | | | |
|---|---|---|---|---|---|
| CN | 103232483 A | | 8/2013 | | |
| CN | 106188113 A | | 12/2016 | | |
| JP | 2014139167 A | * | 7/2014 | ............ | H10K 85/30 |

OTHER PUBLICATIONS http://www.merriamwebster.com/dictionary/derivative, retrieved online Dec. 9, 2015 (Year: 2015).*

Serdar Atilgan, et al., Water soluble distyryl-boradiazaindacenes as efficient photosensitizers for photodynamic therapy, Chemical Communications, 2006, pp. 4398-4400.

Natalia O. Didukh, et al., NIR absorbing diferrocene-containing meso cyano-BODIPY with a UV-Vis-NIR spectrum remarkably close to magnesium tetracyanotetraferrocenyltetraazaporphyrin, Chemical Communications, 2016, pp. 1-5.

Natalia O. Didukh, et al., meso-Nitromethyl-Substituted BODIPYs—A new type of water switchable fluorogenic dyes useful for further core modifications, Dyes and Pigments, 2017.

Daisuke Taguchi, et al., Synthesis and Unique Optical Properties of Selenophenyl BODIPYs and Their Linear Oligomers, The Journal of Organic Chemistry, 2018, pp. 5331-5337, 83.

* cited by examiner

*Primary Examiner* — James W Rogers

(74) *Attorney, Agent, or Firm* — Bayramoglu Law Offices LLC

(57) ABSTRACT

Near-infrared (NIR) absorbing photosensitizers for imaging and treatment of cancer in a photodynamic therapy (PDT) are provided. Specifically, the NIR photosensitizers are mitochondria targeted and water-soluble, and used as a cytotoxic drug in a photodynamic therapy of the cancer. The NIR photosensitizers are activated with wavelengths of light, wherein the light penetrates through a body not just a skin. Hence the NIR photosensitizers aim to transform PDT from being a specialized treatment to a generally applicable one. PDT is almost completely non-invasive compared to current treatment methods.

6 Claims, 1 Drawing Sheet

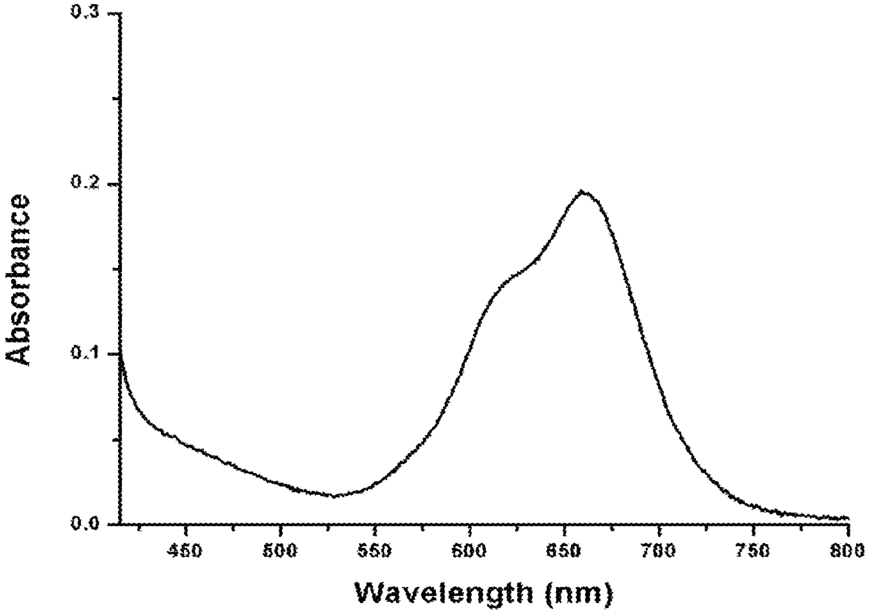
0.3
0.2
0.1
0.0
Absorbance
450
500
550
600
650
700
750
800
Wavelength (nm)

NEAR-INFRARED (NIR) ABSORBING PHOTOSENSITIZERS

CROSS REFERENCE TO THE RELATED APPLICATIONS

This application is a divisional of U.S. application Ser. No. 16/973,435 filed Dec. 9, 2020, which is the national stage entry of International Application No. PCT/TR2018/050322, filed on Jun. 25, 2018, the entire contents of which are incorporated herein by reference.

TECHNICAL FIELD

The present invention relates to photosensitizers to be used for imaging and treatment of cancer by using photodynamic therapy (PDT).

BACKGROUND

Photodynamic therapy (PDT) is a treatment that uses special drugs, called photosensitizing agents, along with light to kill cancer cells. The drugs only work after they have been activated or turned on by certain kinds of light.

In PDT, therapeutic action is satisfied by the generation of singlet oxygen (102) upon irradiation of well-designed PDT agents (photosensitizers or drugs) by light. Singlet oxygen is the excited form of molecular oxygen (302) and it is cytotoxic due to its high reactivity towards vital biomolecules. In addition to this oxidative damage triggered direct killing mode (apoptosis or necrosis) arises from 102 reactivity, PDT also restricts the flow of nutrients and oxygen to cancer cells by disturbing the vasculatures around tumor regions and at the same time activates the immune system against cancer cells. The advantages and importance of PDT are more pronounced when it is compared with widely used conventional chemotherapy and radiotherapy. Although these therapies are the primary choices in clinic practices with a huge market in pharmaceutical industry, they have numerous side effects and give serious damage to the immune system which make them patient unfriendly.

When considered from this aspect; PDT is highly promising, however its broader applicability in clinical treatments is restricted due to some problems. The most important one is the limited penetration of the irradiation light through tissues, which leaves the deeper tumors out from the scope of PDT. Studies have shown that red or near-IR (NIR) absorbing PDT agents should be employed to get the best penetration depth and to avoid the absorption of incoming light by biomolecules. Although, a very wide range of well-known fluorescent probe cores have been converted to PDT agents, red and near-IR absorbing PDT agents are still rare.

The second major problem of the PDT is the oxygen deficiency (hypoxia) in cancer cells. During PDT; singlet oxygen generation is highly dependent on oxygen, which decreases the efficacy of the treatment on hypoxic cancer cells. In addition to this, further oxygen consumption of PDT agents aggravates tumor hypoxia. Accordingly, some of the signaling pathways (ex: HIF-1) are turned-on under severe hypoxia and cause angiogenesis, proliferation and metastasis of hypoxic cancer cells.

The third problem that PDT should overcome is the selective generation of singlet oxygen only in cancer cells without giving harm to healthy cells by employing water soluble and activatable drugs.

Most of the initial photosensitizers (first-generation) and FDA approved drugs are based on a porphyrin skeleton. Although they are really satisfying in terms of singlet oxygen generation and cytotoxicity, almost all of them have water solubility and photostability problems. Later phthalocyanine derivatives were introduced as promising photosensitizers for PDT applications, however synthetic problems and lack of control on photophysical properties restricted their use.

At this point, dipyrrometheneboron difluoride (BODIPY) core appeared to be good candidate due to its tunable photophysical properties, ease of synthesis and modification. Parent BODIPY core is highly hydrophobic and absorbs around 500 nm. Thus; for PDT applications, the core should be modified with water-soluble groups and p-conjugation should be extended in order to have a red-absorbing photosensitizer.

In literature, it is possible to find different version of BODIPYs serving as PDT drugs, however a water-soluble, red-absorbing and at the same time mitochondria targeted BODIPY based PDT agent has not been introduced before. Mitochondria is an important target in order to address hypoxia problem of PDT. It is known that oxygen mechanism is highly evaluated in mitochondria, and this high level of oxygen can be used by PDT agents to generate singlet oxygen efficiently even in aggressive solid tumors, in which severe hypoxia can be observed.

Also; resorufin cores have been extensively used as fluorescent agents for bio-imaging during the last decades, but have not been employed in PDT studies. Resorufin skeleton is quite suitable for PDT applications as it is intrinsically red-absorbing without any modification, photostable and water-soluble.

There is no doubt that revealing new PDT agent cores holding aforementioned properties is highly critical but the most promising and breakthrough outcomes will come from the studies aimed at gaining precise control over the location and rate of the cytotoxic singlet oxygen generation. To that end, most of the new generation PDT drugs are so called "activatable". They remain in a passive state (no cytotoxicity) even under light irradiation and are activated at the site where therapy is desired by cancer cell associated stimuli. In literature, the most widely used approach is to take advantage of the acidic microenvironment of tumors by designing acidic pH activatable PDT drugs. Another common design principle is to employ bio-thiols that are elevated in cancer cells such as glutathione (GSH) as an activating biological input.

As studies on cancer biology and signalling pathways increase, role of many different enzymes in cancer have been uncovered during last decades. Consequently enzymes that are overexpressed in cancer cells appeared to be good candidates for activatable PDT drug designs. Accordingly, caspase-3, cathepsin B, nitroreductase and b-galactosidase activated PDT drugs were introduced with conventional PDT agent cores, however enzyme-activated agents are still rare and their potential can be further evaluated with the help of new generation PDT drug cores.

In this invention, enzyme activated resorufin based PDT agents and BODIPY based PDT agents are synthesized to use in treatment of cancer.

SUMMARY

The invention is about new photosensitizers for wide variety of cancer cells treatment by using photodynamic therapy. These photosensitizers can be activated with wavelengths of light that can penetrate through the body not just skin. Hence the present invention aims to transform PDT from being a specialized treatment to a generally applicable one. PDT is almost completely non-invasive compared to current treatment methods. Additionally due to its non-invasive nature treatment, it can be performed with much shorter intervals compared to chemotherapy. From the perspective of financials, it is known that chemotherapy reagents are expensive. The photosensitizers developed in this invention designed in a way that target compounds can be attained with very small number of steps with cost effective reagents/reactants. Most of the known literature compounds require long synthetic approaches towards achieving some of properties (water solubility, targeting, Near-IR absorption, etc.). The synthetic approaches described in this invention require a small number of steps from commercially available starting materials. Core structures can be attained in 5-6 steps. This creates a significant opportunity for commercialization of these drugs as PDT agents. In addition to this, the BODIPY derivatives synthesized in this invention are addressing the critical light penetration depth and hypoxia problems of PDT and theses BODIPY based photosensitizers are water-soluble, red-absorbing and at the same time mitochondria targeted.

BRIEF DESCRIPTION OF THE DRAWINGS

FIG. 1 Absorption of selenophene-substituted BODIPY derivative.

DETAILED DESCRIPTION OF THE EMBODIMENTS

In the present invention, BODIPY based and resorufin based photosensitizers are synthesized for use in photodynamic therapy of cancer.

BODIPY-Based Photosensitizers

These sensitizers are modified with selenophene (Se-BOD) or iodo-selenophene (SeL-BOD) units at 2 and 6 positions of the BODIPY core in order to facilitate intersystem crossing (ISC) upon external light irradiation as a result of heavy atom (selenium or selenium (Se) and iodine (I)) mediated spin-orbit coupling. These BODIPY derivatives absorb red-light around 650 nm and highly water soluble with the help of methyl pyridinium moities such that only 0.1% DMSO as a co-solvent is needed to get clear solutions. Methyl pyridinium groups contribute to three important issues. First, these groups improve the water solubility of the PDT drug as mentioned. Second, they cause a red-shift in the absorption signal and finally they direct the drug to mitochondria (mitochondria targeting). It is known in the literature that most of the solid tumors are oxygen deficient (hypoxic). This hypoxic condition within the tumor cells is areal challenge for PDT drugs since the therapy itself consumes oxygen to generate cytotoxic singlet oxygen, which makes PDT a self-restricting method. One way to address this drawback is to direct PDT drugs to mitochondria, where the oxygen metabolism is high. Common strategy for mitochondria targeting is to use cationic species such as triphenylphosphine and methyl/hexyl pyridinium moieties. In this invention it is decided to use preferably methyl pyridinium, since it has several aforementioned advantages and it is east to synthesize.

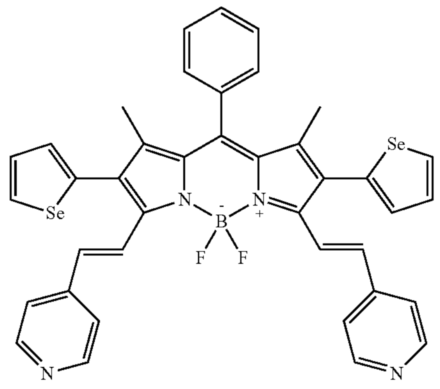

Se-BOD

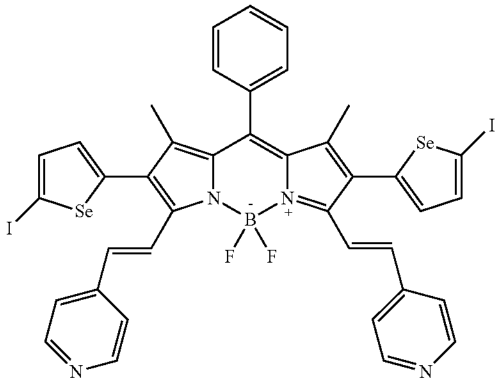

SeI-BOD

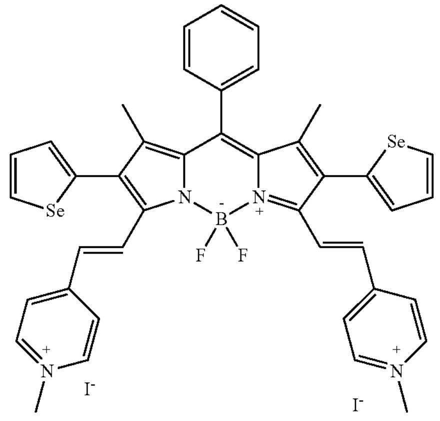

Se-BOD-Me

-continued

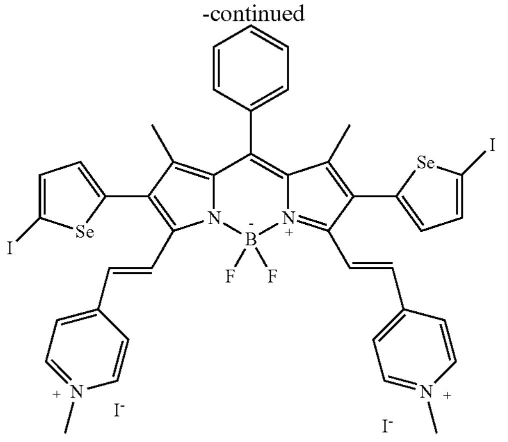

Se-BOD-Me

All these features mentioned above combined with selenophene incorporation into the BODIPY results in a PDT drug with high water solubility, absorption in the near IR region (>650 nm) increased singlet oxygen generation efficiency (compared to bromine substitution) and mitochondria targeting abilities. Hence, the system described here in this invention is a patient ready cancer treatment PDT drug. Fluorescence quantum yield of the sensitizers (8.5% for Se-BOD) are low as ISC pathway is active. Singlet oxygen quantum yield for Se-BOD was calculated as 18% in phosphate buffered saline (PBS) (pH 7.4, 10 mM) with 0.1% dimethyl sulfoxide (DMSO).

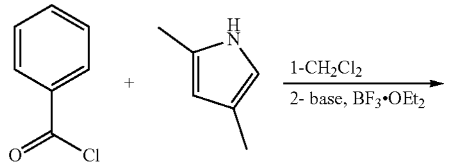

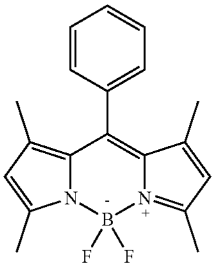

(1)

Commercially available benzoyl chloride ($C_6H_5COCl$) and 2,4-dimethylpyrrole are dissolved in methylene chloride ($CH_2Cl_2$) and stirred at 0° C. to 40° C. until starting material finished. Then proper amine base and boron trifluoride diethyl etherate ($BF_3{\cdot}OEt_2$) is added and stirred 6-12 h. Then washed with water and purified by column chromatography and Compound 1 is synthesized successfully.

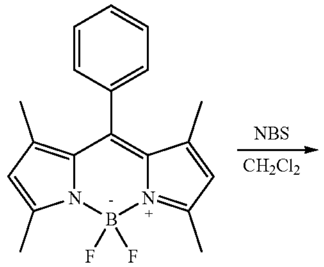

(1)

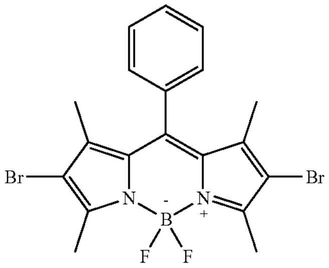

(2)

To a solution of Compound 1 in $CH_2Cl_2$, a solution of N-bromosuccinimide (NBS) in $CH_2Cl_2$ is added and stirred 2-4 h at 0-40° C. then washed with water and brine and purified by column chromatography and Compound 2 is synthesized successfully.

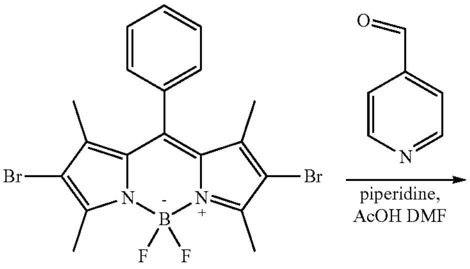

(2)

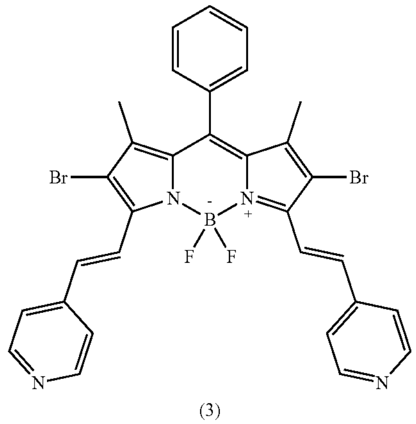

(3)

Compound 2 dissolved in dry N,N-dimethylformamide (DMF) and 4-pyridinecarboxyaldehyde, piperidine and acetic acid (AcOH) are added. Reaction mixture is stirred for 1-2 h at 0°-40° C., then solvent is evaporated and purified by column chromatography to yield Compound 3 successfully.

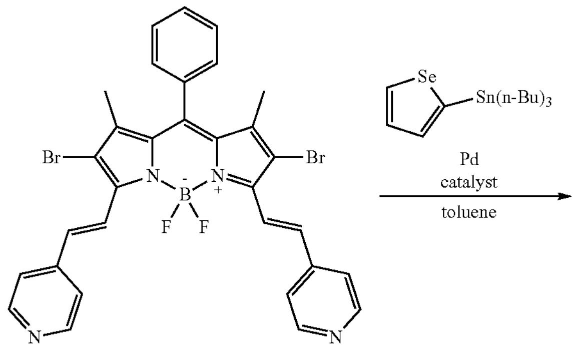

(3)

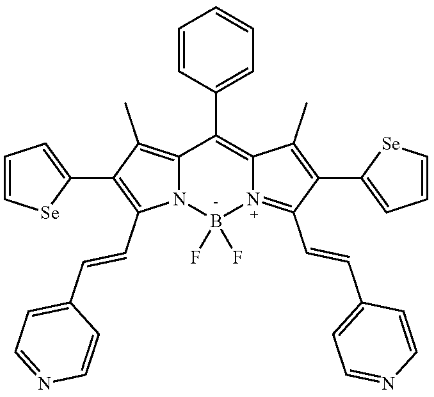

(4)

Compound 3 is dissolved in toluene, then stannylated selenophene and palladium (Pd) catalyst (Pd(PPh3)Cl2, Pd(OAc)2 etc.) are added and stirred for 4-6 days at 100-140° C. Then it is washed with potassium fluoride (KF) solution and purified by column chromatography to yield Compound 4.

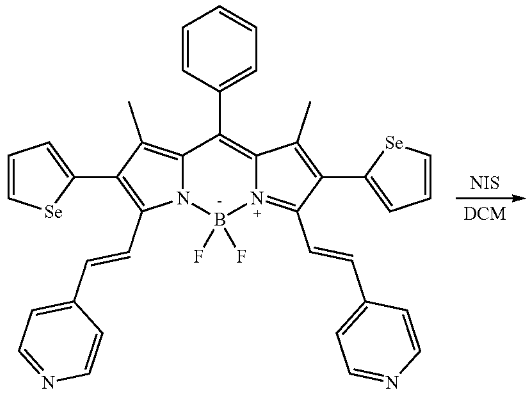

(4)

-continued

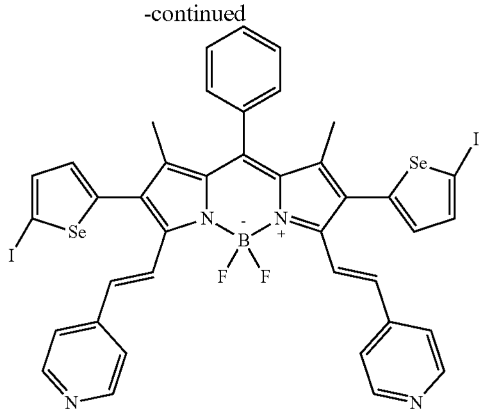

(5)

To a solution of Compound 4 in $CH_2Cl_2$, a solution of N-iodosuccinimide (NIS) in $CH_2Cl_2$ is added. Reaction mixture is stirred for 12-24 h at 0-40° C. and washed with water and sodium bicarbonate ($NaHCO_3$). Purification is performed by column chromatography to yield Compound 5.

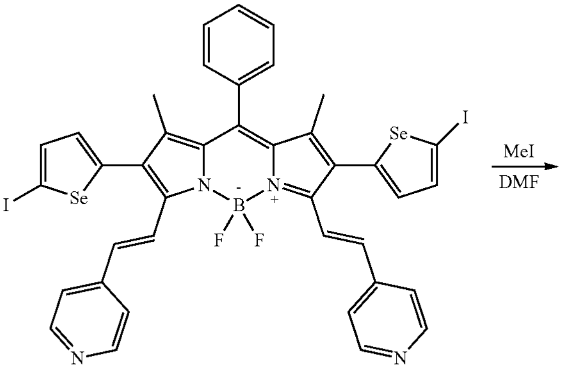

(5)

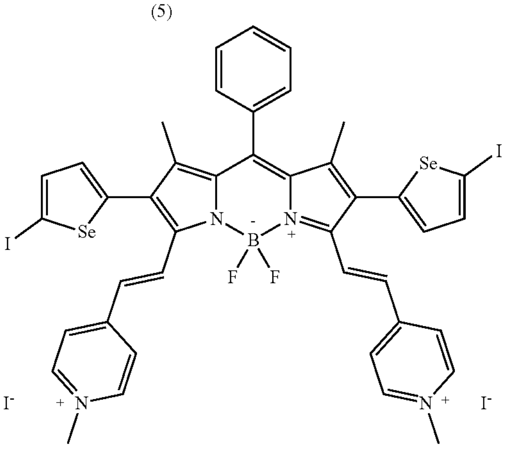

(6)

To a solution of Compound 5 in dry DMF, methyliodide is added and stirred 1-3 days at 0-40° C. The reaction mixture is precipitated with diethylether with the presence of DMF and Compound 6 is synthesized successfully.

In this invention heavy atoms are used in the synthesis of photosensitizer derivatives. Presence of heavy atoms is a requirement for a PDT drug. Once the sensitizers are excited with light to a singlet excited state presence of heavy atoms results in inter system crossing and a triplet excited state is generated. This triplet excited states is responsible for the generation of triplet oxygen from the oxygen present in the cells. Iodine as a heavy atom favors inter-system crossing by itself. In this invention, the aim is to increase the number of heavy atoms on the BODIPY core in order to increase the singlet oxygen generation yield of the drug synthesized in this invention through synergistic effect of selenium and iodine. Upon generation of singlet oxygen, it reacts with vital bio-molecules causing oxidative damage, which results in cell death. In addition to direct killing of cancer cells, PDT also restricts the follow of nutrients and oxygen to cancer cells by damaging the vasculatures around tumor regions and at the same time activates immune system against cancer cells.

General Structure of Synthesized BODIPY-Based Photosensitizers

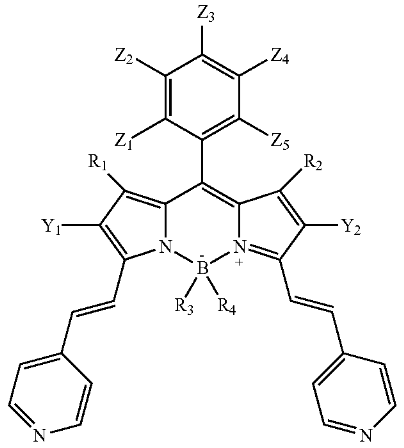

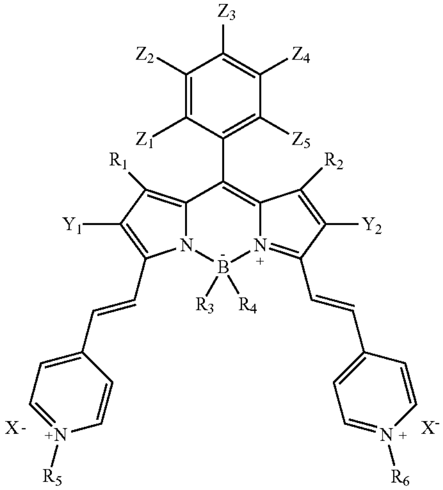

$Z_1$ =

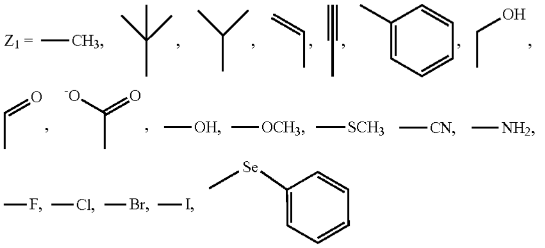

-continued $Z_2$ =

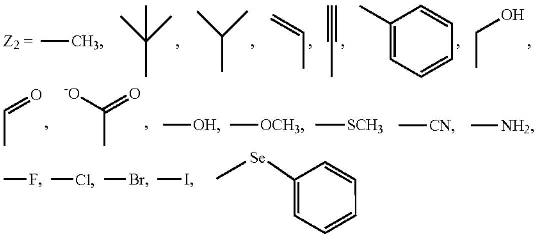

$Z_3$ =

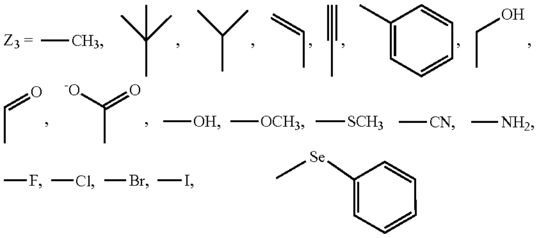

$Z_4$ =

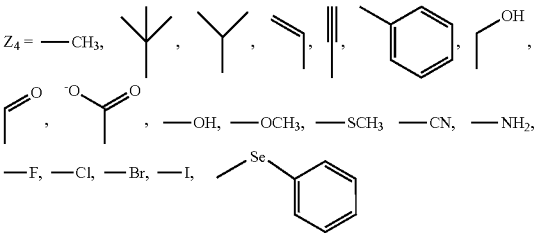

$Z_5$ =

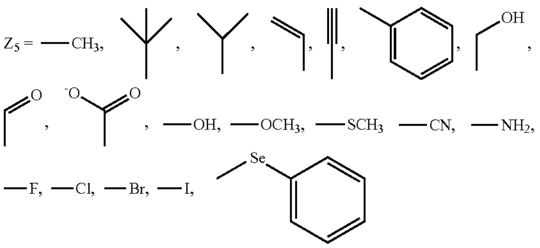

$R_1$ =

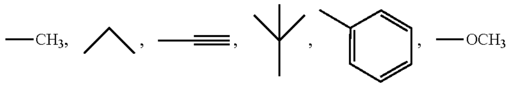

$R_2$ =

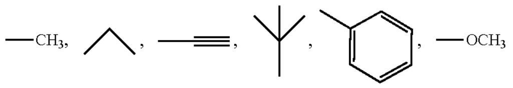

$R_3$ =

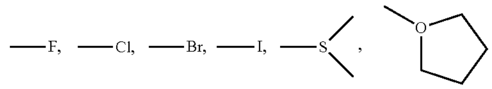

$R_4$ =

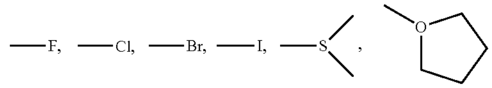

$R_5$ = —Me, —Et, —Pt, —Bu, any other possible alkyl and aryl derivatives.

$R_6$ = —Me, —Et, —Pt, —Bu, any other possible alkyl and aryl derivatives.

X = F, Cl, Br, I $Y_1$ =

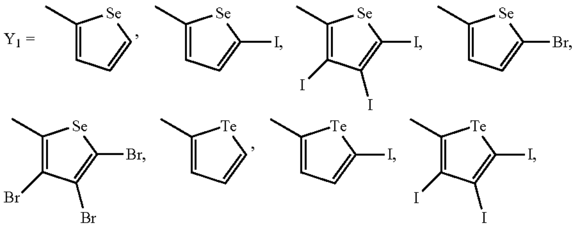

-continued

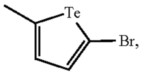 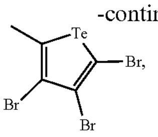 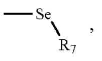

$R_7$ = alkyl or aryl derivatives

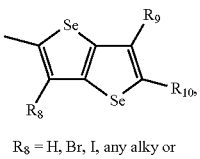 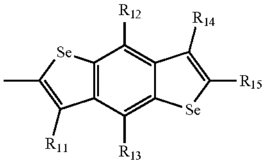

$R_8$ = H, Br, I, any alky or aryl derivatives
$R_9$ = H, Br, I, any alkyl or aryl derivatives
$R_{10}$ = H, Br, I, any alkyl or aryl derivatives $R_{11}$ = H, Br, I, any alkyl or aryl derivatives
$R_{12}$ = H, Br, I, any alkyl or aryl derivatives
$R_{13}$ = H, Br, I, any alkyl or aryl derivatives
$R_{14}$ = H, Br, I, any alkyl or aryl derivatives
$R_{15}$ = H, Br, I, any alkyl or aryl derivatives $Y_2$ = 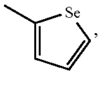 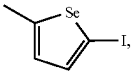 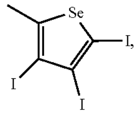 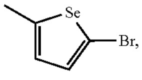

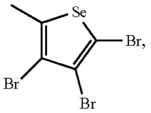 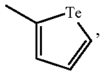 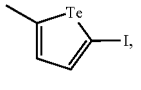 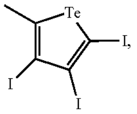

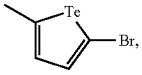 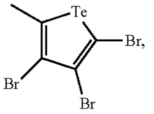 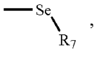

$R_7$ = alkyl or aryl derivatives

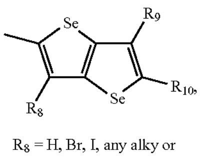 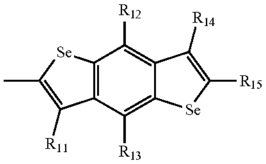

$R_8$ = H, Br, I, any alky or aryl derivatives
$R_9$ = H, Br, I, any alkyl or aryl derivatives
$R_{10}$ = H, Br, i, any alkyl or aryl derivatives $R_{11}$ = H, Br, I, any alkyl or aryl derivatives
$R_{12}$ = H, Br, I, any alkyl or aryl derivatives
$R_{13}$ = H, Br, I, any alkyl or aryl derivatives
$R_{14}$ = H, Br, I, any alkyl or aryl derivatives Resorufin-Based Photosensitizers Resorufin derivatives are introduced as photosensitizers for photodynamic therapy of cancer for the first time in this invention. Iodine is incorporated to the core structure as a heavy atom in order to favor ISC. These resorufin-based sensitizers are enzyme activated in such a way that cytotoxicity can only be observed in cancer cells. In the case of PDT agent, a sugar cage group β-D-galactopyranoside is attached to the iodinated-resorufin core and this modification shifted the absorption maximum of the drug to 500 nm. In literature it is known that β-D-galactopyranoside sugar cage can be removed selectively with b-galactosidase enzyme, which is overexpressed in several cancer types including ovarian and liver cancers. As a result of reaction between b-galactosidase and the PDT agent sugar cage removed and the absorption maximum of the resorufin core is red-shifted to 600 nm. Consequently, by adjusting the excitation wavelength during the PDT action to 600 nm, the PDT agent becomes cytotoxic only in cancer cells in which the b-galactosidase concentration is high, and on the contrary no cytotoxicity is observed in healthy cells as the PDT agent does not absorb the irradiation light at 600 nm. PDT drug functions are similar, but the cage group is replaced by a propanamine, which can be selectively cleaved by monoamine oxidase (MAO) enzyme. The PDT drug does not show any cytotoxicity in health cells, but it is highly cytotoxic in cancer cells upon 600 nm irradiation.

A new fluorophore core, silicon-substituted resorufin (Turkey Red) is designed and synthesized in this invention. It has red shifted absorption and emission signals compared to conventional resorufin (oxygen-substituted resorufin). This new core is also converted to a cytotoxic photosensitizer for PDT applications simply by decorating the core structure with heavy atoms such as bromine or iodine.

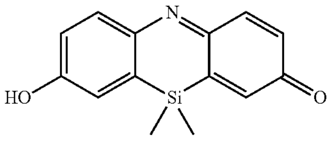

Turkey Red

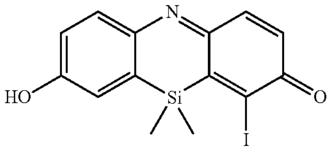

(mono)iodo-Turkey Red

Replacing oxygen with silicon and phosphine oxide is causing approximately 100 nm red shift in the absorption spectra of the cores which is quite unusual. Just replacing one atom of the core results in a very strong shift which in turn makes these cores quite valuable for PDT applications. The change of $sp^2$ carbon atom with nitrogen in the fluorescein core results in resorufin. Here almost a 100 nm shift is also observed. One of the main ideas in this invention is combining both sp2 carbon to nitrogen change and oxygen to silicon/phosphine oxide change in the same core and has a combined effect of almost 200 nm red shift. This results in a record red shift with simply modifying the core structures which is very valuable since other approaches to attain NIR absorption requires many synthetic steps and transformations which make the drug candidates extremely expensive.

The Synthesis of Resorufin-Based Photosensitizer of Formula Below:

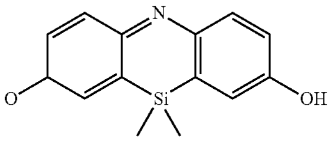 [SMILES: C[Si]1(C)C2=CC(O)C=CC2=Nc2ccc(O)cc21]

Commercially available bis(4-methoxyphenyl)amine is treated with % 30-50 hydrogen bromide (HBr) and Aliquat 336 at 70-120° C. for 12-48 hours. Mixture is diluted with water and extracted with ethyl acetate (EtOAc). The solvent is evaporated and residue is washed with hexane to get the demethylated product 4,4'-azanediyldiphenol.

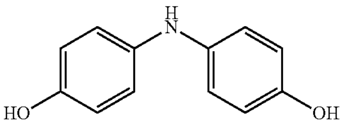 [SMILES: Oc1ccc(Nc2ccc(O)cc2)cc1]

4,4'-azanediyldiphenol 4,4'-azanediyldiphenol is brominated with NBS (2-4 equivalents) in acetonitrile at (−10)-25° C. The mixture is stirred for 2-8 hours. Solvent is removed and the residue is dissolved in THF. The mixture is filtered through Celite and purified by column chromatography to give the dibrominated product 4,4'-azanediylbis(3-bromophenol).

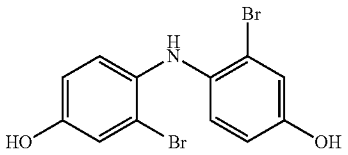 [SMILES: Oc1ccc(Nc2ccc(O)cc2Br)c(Br)c1]

4,4'-azanediylbis(3-bromophenol)

4,4'-azanediylbis(3-bromophenol) is treated with sodium hydride (NaH, 4-6 equivalents) in DMF at (−10)-25° C. Mixture is stirred for 1-2 hours and then benzyl bromide (4-6 equivalents) is added and the mixture is heated to 70-100° C. for 4-18 hours. Water is added and the mixture was extracted with diethyl ether ($Et_2O$). The solvent is evaporated and the product shown in below is attained by column chromatography.

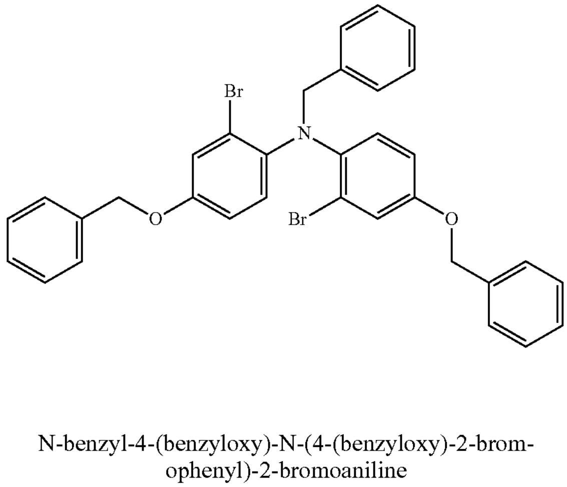

N-benzyl-4-(benzyloxy)-N-(4-(benzyloxy)-2-bromophenyl)-2-bromoaniline

N-benzyl-4-(benzyloxy)-N-(4-(benzyloxy)-2-bromophenyl)-2-bromoaniline is dissolved in $Et_2O$ and the mixture is cooled to −80° C. to −20° C. n-butyllithium (n-BuLi) is added and the mixture is stirred for 1 hour. Then dichloro (dimethyl)silane ($SiMe_2Cl_2$) is added and the mixture is gradually warmed to room temperature. $Et_2O$ and water are added into the mixture and the organic phase is separated. Solvent is evaporated and the residue is purified by column chromatography to give 5-benzyl-2,8-bis(benzyloxy)-10,10-dimethyl-5,10-dihydrodibenzo[b,e][1,4]azasiline.

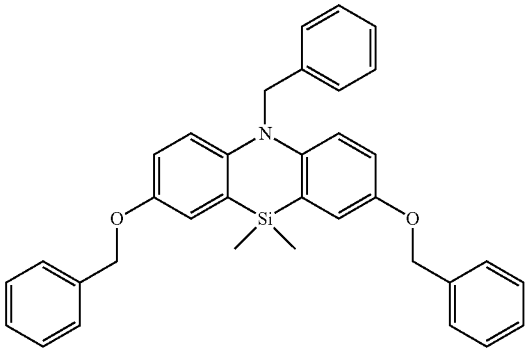 [SMILES: C[Si]1(C)c2cc(OCc3ccccc3)ccc2N(Cc2ccccc2)c2ccc(OCc3ccccc3)cc21]

5-benzyl-2,8-bis(benzyloxy)-10,10-dimethyl-5,10-dihydrodibenzo[b,e][1,4]azasiline 5-benzyl-2,8-bis(benzyloxy)-10,10-dimethyl-5,10-dihydrodibenzo[b,e][1,4]azasiline is dissolved in ethanol and palladium on carbon (Pd/C) is added at 0-30° C. The system is vacuumed and filled with hydrogen ($H_2$) gas. The mixture is stirred for 4-12 hours. The mixture is diluted with ethanol and filtered through celite. The solvent is evaporated and the mixture is purified by column chromatography.

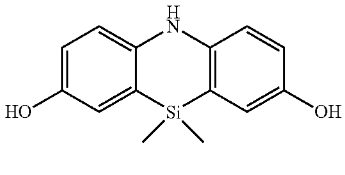 [SMILES: C[Si]1(C)c2cc(O)ccc2Nc2ccc(O)cc21]

10,10-dimethyl-5,10-dihydrodibenzo[b,e][1,4]azasiline-2,8-diol 10,10-dimethyl-5,10-dihydrodibenzo[b,e][1,4]azasiline-2,8-diol is dissolved in DCM and an appropriate oxidant (DDQ, Dess-Martin, etc) is added at (−10)-25° C. The mixture is stirred for 2-12 hours and the mixture is diluted with dichloromethane (DCM) and filtered through celite. The residue is washed with water and the organic solvent is evaporated. The residue was purified by column chromatography to get the title compound of formula below.

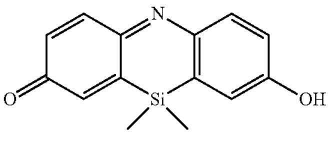 [SMILES: C[Si]1(C)C2=CC(=O)C=CC2=Nc2ccc(O)cc21]

8-hydroxy-10,10-dimethyldibenzo[b,e][1,4]azasilin-2(10H)-one

The synthesis of resorufin-based photosensitizer of formula below:

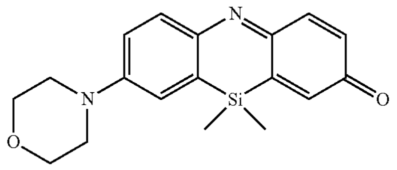 [SMILES: C[Si]1(C)C2=CC(=O)C=CC2=Nc2ccc(N3CCOCC3)cc21]

10,10-dimethyl-5,10-dihydrodibenzo[b,e][1,4]azasiline-2,8-diol is dissolved in DCM. Pyridine is added and the mixture is cooled to (−20)−10° C. Triflic anhydride is then added and the mixture is stirred for 1-4 hours. The mixture is diluted with DCM and washed with water. The organic solvent is evaporated and the product shown in below is attained.

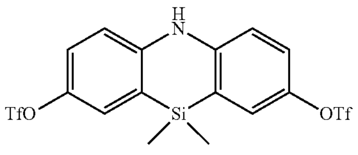 [SMILES: C[Si]1(C)c2cc(OS(=O)(=O)C(F)(F)F)ccc2Nc2ccc(OS(=O)(=O)C(F)(F)F)cc21]

10,10-dimethyl-5,10-dihydrodibenzo[b,e][1,4]azasiline-2,8-diyl bis(trifluoromethanesulfonate)

10,10-dimethyl-5,10-dihydrodibenzo[b,e][1,4]azasiline-2,8-diyl bis(trifluoromethanesulfonate) is dissolved in toluene and Pd(OAc)2 and an appropriate ligand (Xantphos, DavePhos, XPhos, etc) is added. The system is purged with argon and the appropriate amine (in this example morpholine) is added. The mixture is stirred at 50-100° C. for 12-36 hours. The reaction was diluted with EtOAc and washed with water. The solvent was evaporated. The residue was treated with Et4NOH in MeOH the residue was purified by column chromatography.

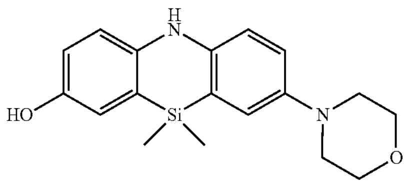 [SMILES: C[Si]1(C)c2cc(O)ccc2Nc2ccc(N3CCOCC3)cc21]

10,10-dimethyl-8-morpholino-5,10-dihydrodibenzo[b,e][1,4]azasilin-2-ol 10,10-dimethyl-8-morpholino-5,10-dihydrodibenzo[b,e][1,4]azasilin-2-ol was dissolved in DCM and an appropriate oxidant (DDQ, Dess-Martin, etc) was added at −10-25° C. The mixture was stirred for 2-12 hours and the mixture was diluted with DCM and filtered through Celite. The residue was washed with water and the organic solvent was evaporated. The residue was purified by column chromatography to get the title compound.

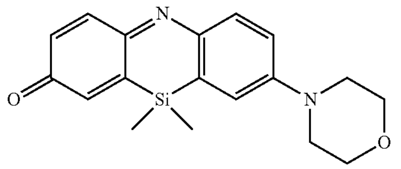 [SMILES: C[Si]1(C)C2=CC(=O)C=CC2=Nc2ccc(N3CCOCC3)cc21]

10,10-dimethyl-8-morpholinodibenzo[b,e][1,4]azasilin-2(10H)-one

The synthesis of resorufin-based photosensitizer of formula below:

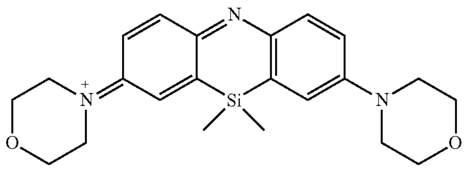

10,10-dimethyl-5,10-dihydrodibenzo[b,e][1,4]azasiline-2,8-diyl bis(trifluoromethanesulfonate) was dissolved in toluene and Pd(OAc)2 and an appropriate ligand (Xantphos, DavePhos, XPhos, etc) was added. The system was purged with argon and the appropriate amine (in this example dime was added. The mixture was stirred at 50-100° C. for 12-36 hours. The reaction was diluted with EtOAc and washed with water. The solvent was evaporated and the residue was purified by column chromatography.

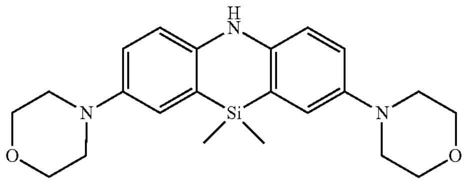 [SMILES: C[Si]1(C)c2cc(N3CCOCC3)ccc2Nc2ccc(N3CCOCC3)cc21]

10,10-dimethyl-8-morpholino-5,10-dihydrodibenzo[b,e][1,4]azasilin-2-ol 10,10-dimethyl-8-morpholino-5,10-dihydrodibenzo[b,e][1,4]azasilin-2-ol was dissolved in DCM and an appropriate oxidant (DDQ, Dess-Martin, etc) was added at −10-25° C. The mixture was stirred for 2-12 hours and the mixture was diluted with DCM and filtered through Celite. The residue was washed with water and the organic solvent was evaporated. The residue was purified by column chromatography to get the title compound.

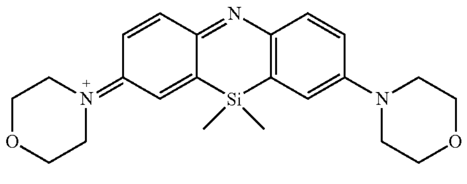

10,10-dimethyl-8-morpholinodibenzo[b,e][1,4]azasilin-2(10H)-one

The synthesis of resorufin-based photosensitizer of formula below:

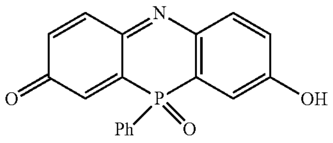 [SMILES: O=C1C=CC2=Nc3ccc(O)cc3P(=O)(c3ccccc3)C2=C1]

N-benzyl-4-(benzyloxy)-N-(4-(benzyloxy)-2-bromophenyl)-2-bromoaniline was dissolved in Et2O and the mixture was cooled to −80 to −20° C. n-BuLi was added and the mixture was stirred for 1 hour. Then PPhC12 was added and the mixture was gradually warmed to room temperature. H2O2 was added and the mixture was stirred for 1-3 hours. EtOAc was added and water was added the organic phase was separated. Solvent was evaporated and the residue purified by column chromatography to give the title compound.

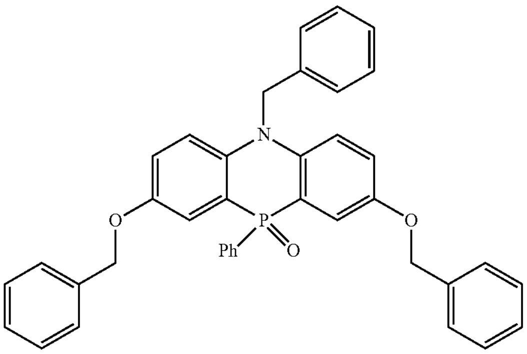 [SMILES: O=P1(c2ccccc2)c2cc(OCc3ccccc3)ccc2N(Cc2ccccc2)c2ccc(OCc3ccccc3)cc21]

5-benzyl-2,8-bis(benzyloxy)-10-phenyl-5H-phenophosphazinine 10-oxide 5-benzyl-2,8-bis(benzyloxy)-10-phenyl-5H-phenophosphazinine 10-oxide was dissolved in Ethanol and Pd/C was added at 0-30° C. The system was vacuumed and filled with H2 gas. The mixture was stirred for 4-12 hours. The mixture was diluted with Ethanol and filtered through Celite. The solvent was evaporated and the mixture was purified by column chromatography.

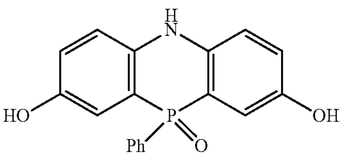 [SMILES: O=P1(c2ccccc2)c2cc(O)ccc2Nc2ccc(O)cc21]

2,8-dihydroxy-10-phenyl-5H-phenophosphazinine 10-oxide 2,8-dihydroxy-10-phenyl-5H-phenophosphazinine 10-oxide was dissolved in DCM and an appropriate oxidant (DDQ, Dess-Martin, etc) was added at −10-25° C. The mixture was stirred for 2-12 hours and the mixture was diluted with DCM and filtered through Celite. The residue was washed with water and the organic solvent was evaporated. The residue was purified by column chromatography to get the title compound.

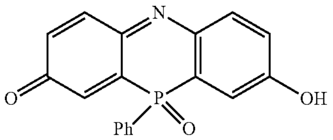 [SMILES: O=C1C=CC2=Nc3ccc(O)cc3P(=O)(c3ccccc3)C2=C1]

8-hydroxy-10-phenyl-2H-phenophosphazinin-2-one 10-oxide

The synthesis of resorufin-based photosensitizer of formula below:

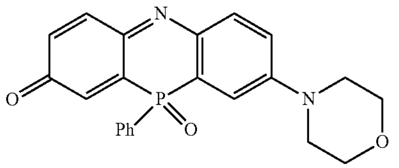 [SMILES: O=C1C=CC2=Nc3ccc(N4CCOCC4)cc3P(=O)(c3ccccc3)C2=C1]

2,8-dihydroxy-10-phenyl-5H-phenophosphazinine 10-oxide was dissolved in DCM. Pyridine was added and the mixture was cooled to −20-10° C. Triflic anhydride was then added and the mixture was stirred for 1-4 hours. The mixture was diluted with DCM and washed with water. The organic solvent was evaporated and the title product was attained.

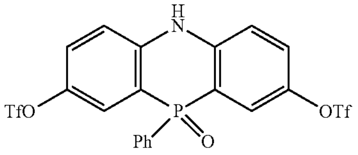 [SMILES: O=P1(c2ccccc2)c2cc(OS(=O)(=O)C(F)(F)F)ccc2Nc2ccc(OS(=O)(=O)C(F)(F)F)cc21]

10-oxido-10-phenyl-5H-phenophosphazinine-2,8-diyl bis(trifluoromethanesulfonate)

10-oxido-10-phenyl-5H-phenophosphazinine-2,8-diyl bis (trifluoromethanesulfonate) was dissolved in toluene and Pd(OAc)2 and an appropriate ligand (Xantphos, DavePhos, XPhos, etc) was added. The system was purged with argon and the appropriate amine (in this example morpholine) was added. The mixture was stirred at 50-100° C. for 12-36 hours. The reaction was diluted with EtOAc and washed with water. The solvent was evaporated. The residue was treated with Et4NOH in MeOH the residue was purified by column chromatography.

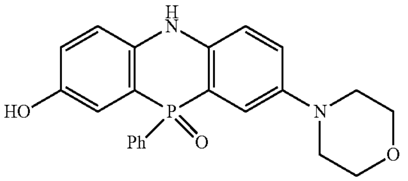 [SMILES: O=P1(c2ccccc2)c2cc(O)ccc2Nc2ccc(N3CCOCC3)cc21]

2-hydroxy-8-morpholino-10-phenyl-5H-phenophosphazinine 10-oxide 2-hydroxy-8-morpholino-10-phenyl-5H-phenophosphazinine 10-oxide was dissolved in DCM and an appropriate oxidant (DDQ, Dess-Martin, etc) was added at −10-25° C. The mixture was stirred for 2-12 hours and the mixture was diluted with DCM and filtered through Celite. The residue was washed with water and the organic solvent was evaporated. The residue was purified by column chromatography to get the title compound.

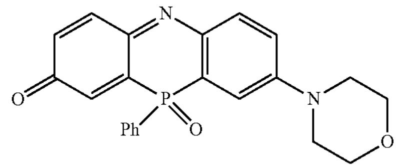 [SMILES: O=C1C=CC2=Nc3ccc(N4CCOCC4)cc3P(=O)(c3ccccc3)C2=C1]

8-morpholino-10-phenyl-2H-phenophosphazinin-2-one 10-oxide

The synthesis of resorufin-based photosensitizer of formula below:

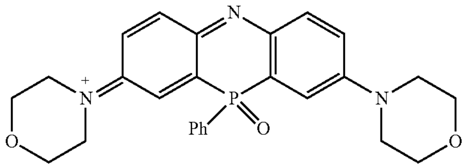

10-oxido-10-phenyl-5H-phenophosphazinine-2,8-diyl bis(trifluoromethanesulfonate) was dissolved in toluene and Pd(OAc)2 and an appropriate ligand (Xantphos, DavePhos, XPhos, etc) was added. The system was purged with argon and the appropriate amine (in this example morpholine) was added. The mixture was stirred at 50-100° C. for 12-36 hours. The reaction was diluted with EtOAc and washed with water. The solvent was evaporated. The residue was treated with Et4NOH in MeOH the residue was purified by column chromatography.

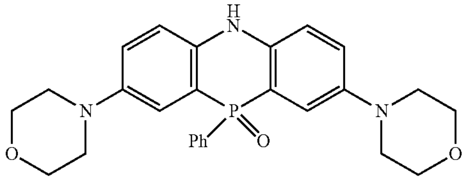 [SMILES: O=P1(c2ccccc2)c2cc(N3CCOCC3)ccc2Nc2ccc(N3CCOCC3)cc21]

2,8-dimorpholino-10-phenyl-5H-phenophosphazinine 10-oxide 2,8-dimorpholino-10-phenyl-5H-phenophosphazinine 10-oxide was dissolved in DCM and an appropriate oxidant (DDQ, Dess-Martin, etc) was added at −10-25° C. The mixture was stirred for 2-12 hours and the mixture was diluted with DCM and filtered through Celite. The residue was washed with water and the organic solvent was evaporated. The residue was purified by column chromatography to get the title compound.

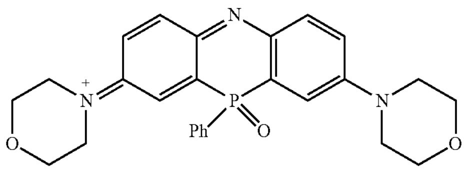

4-(8-morpholino-10-oxido-10-phenyl-2H-phenophosphazinin-2-ylidene)morpholin-4-ium General Structure of Synthesized Resorufin-Based Photosensitizers

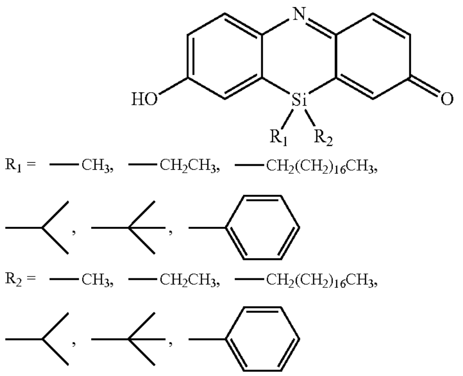

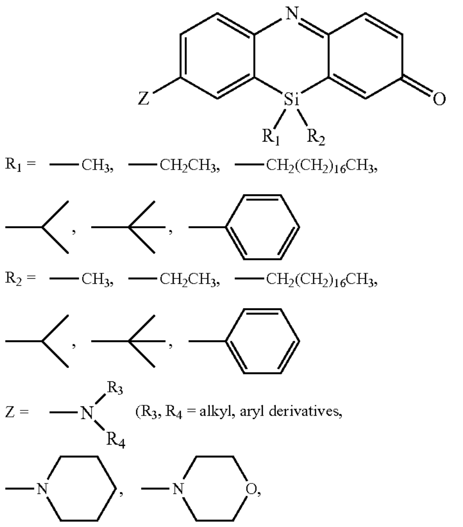

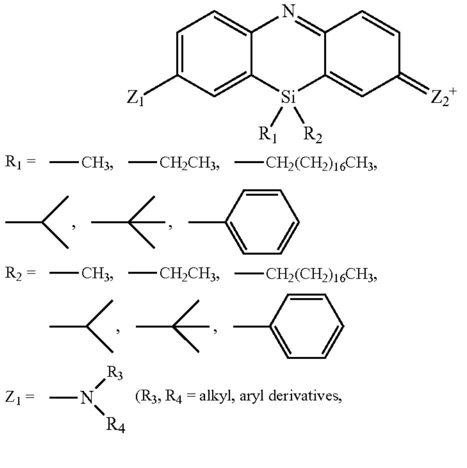

-continued

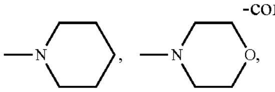

$Z_2$ = 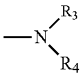 ($R_3$, $R_4$ = alkyl, aryl derivatives,

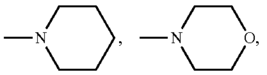

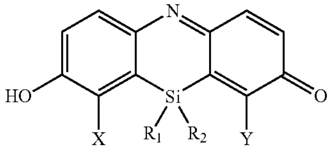

$R_1$ = $-CH_3$, $-CH_2CH_3$, $-CH_2(CH_2)_{16}CH_3$,

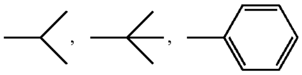

$R_2$ = $-CH_3$, $-CH_2CH_3$, $-CH_2(CH_2)_{16}CH_3$,

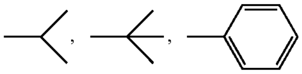

X = —Br, —I, 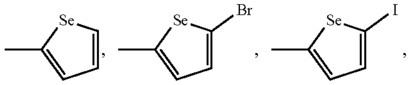

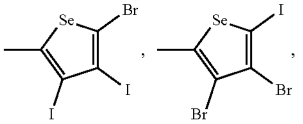

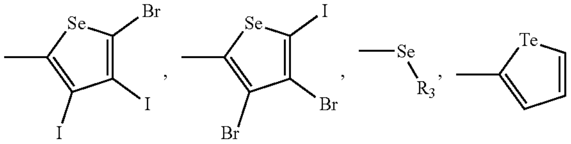

$R_3$ = alkyl, aryl derivatives

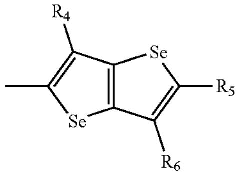

$R_4$ = H, Br, I alkyl and aryl derivatives
$R_5$ = H, Br, I alkyl and aryl derivatives
$R_6$ = H, Br, I alkyl and aryl derivatives

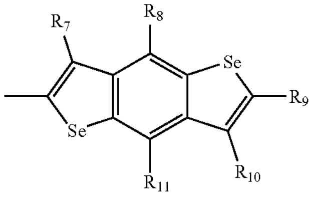

$R_7$ = H, Br, I alkyl and aryl derivatives
$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives Y = —Br, —I, 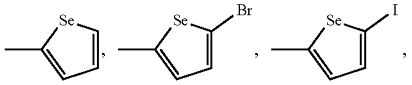

-continued

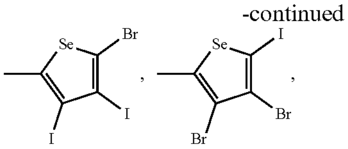

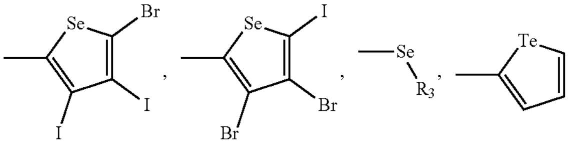

$R_3$ = alkyl, aryl derivatives

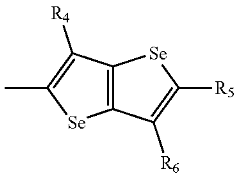

$R_4$ = H, Br, I alkyl and aryl derivatives
$R_5$ = H, Br, I alkyl and aryl derivatives
$R_6$ = H, Br, I alkyl and aryl derivatives

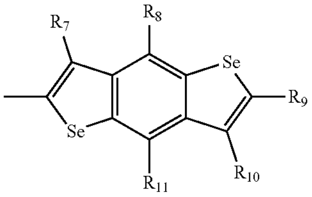

$R_7$ = H, Br, I alkyl and aryl derivatives
$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives

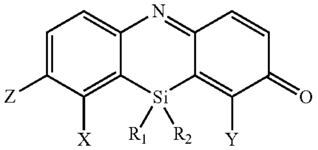

$R_1$ = $-CH_3$, $-CH_2CH_3$, $-CH_2(CH_2)_{16}CH_3$,

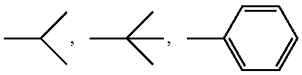

$R_2$ = $-CH_3$, $-CH_2CH_3$, $-CH_2(CH_2)_{16}CH_3$,

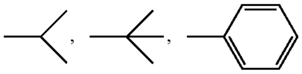

Z = 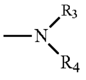 ($R_3$, $R_4$ = alkyl, aryl derivatives,

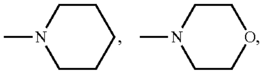

X = —Br, —I, 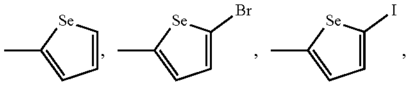

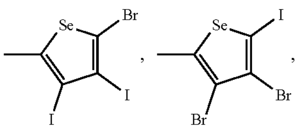

-continued

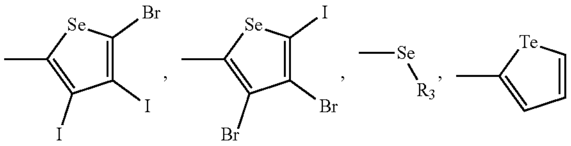

$R_3$ = alkyl, aryl derivatives

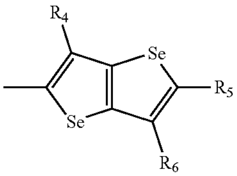

$R_4$ = H, Br, I alkyl and aryl derivatives
$R_5$ = H, Br, I alkyl and aryl derivatives
$R_6$ = H, Br, I alkyl and aryl derivatives

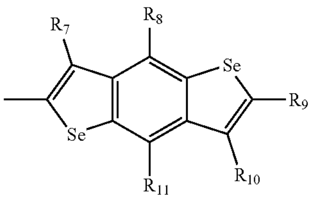

$R_7$ = H, Br, I alkyl and aryl derivatives
$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives

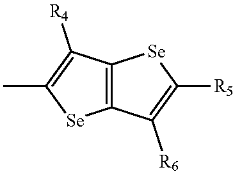

$R_4$ = H, Br, I alkyl and aryl derivatives
$R_5$ = H, Br, I alkyl and aryl derivatives
$R_6$ = H, Br, I alkyl and aryl derivatives

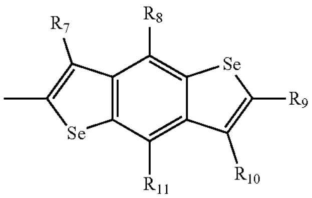

$R_7$ = H, Br, I alkyl and aryl derivatives
$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives Y = —Br, —I,

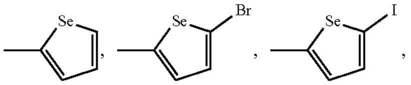

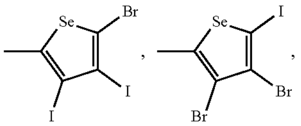

-continued

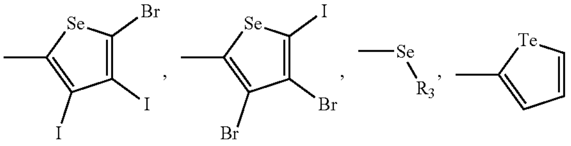

$R_3$ = alkyl, aryl derivatives

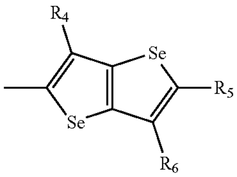

$R_4$ = H, Br, I alkyl and aryl derivatives
$R_5$ = H, Br, I alkyl and aryl derivatives
$R_6$ = H, Br, I alkyl and aryl derivatives

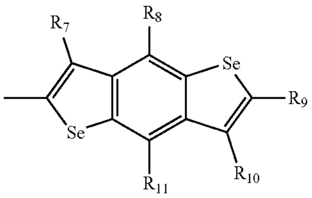

$R_7$ = H, Br, I alkyl and aryl derivatives
$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives

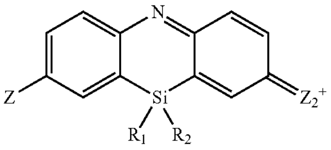

$R_1$ = $—CH_3$, $—CH_2CH_3$, $—CH_2(CH_2)_{16}CH_3$,

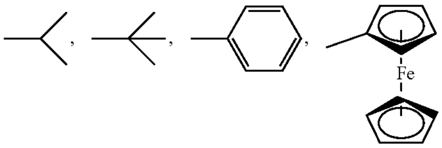

$R_1$ = $—CH_3$, $—CH_2CH_3$, $—CH_2(CH_2)_{16}CH_3$,

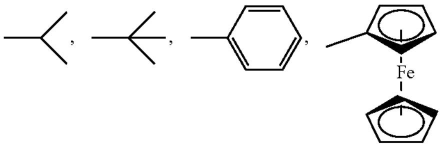

$Z_1$ = 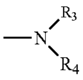 ($R_3$, $R_4$ = alkyl, aryl derivatives,

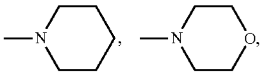

$Z_2$ = 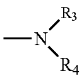 ($R_3$, $R_4$ = alkyl, aryl derivatives,

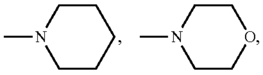

-continued

X = 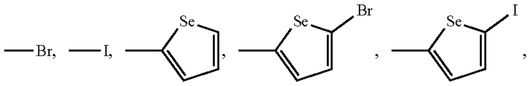

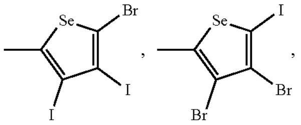

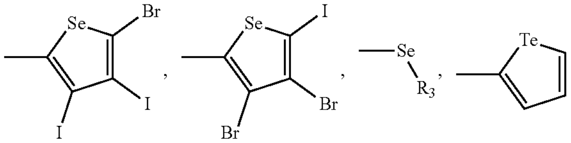

$R_3$ = alkyl, aryl derivatives

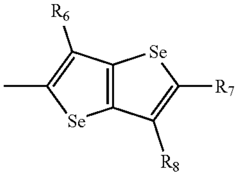

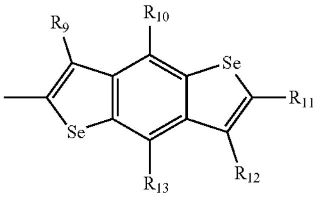

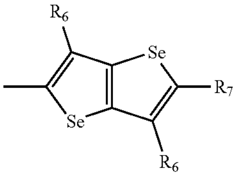

$R_6$ = H, Br, I alkyl and aryl derivatives
$R_7$ = H, Br, I alkyl and aryl derivatives
$R_8$ = H, Br, I alkyl and aryl derivatives

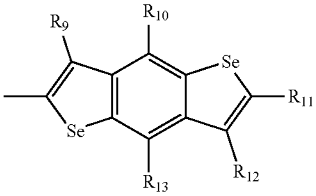

$R_9$ = H, Br, I alkyl and aryl derivatives
$R_{10}$ = H, Br, I alkyl and aryl derivatives
$R_{11}$ = H, Br, I alkyl and aryl derivatives
$R_{12}$ = H, Br, I alkyl and aryl derivatives
$R_{13}$ = H, Br, I alkyl and aryl derivatives Y = 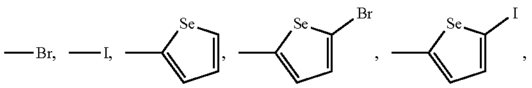

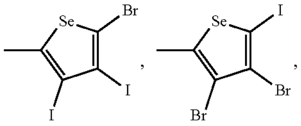

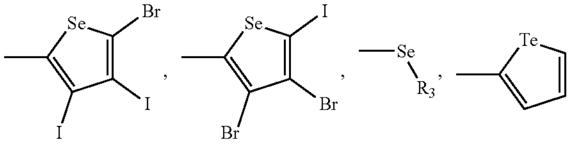

$R_3$ = alkyl, aryl derivatives

-continued

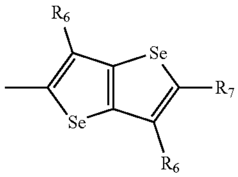

$R_6$ = H, Br, I alkyl and aryl derivatives
$R_7$ = H, Br, I alkyl and aryl derivatives
$R_8$ = H, Br, I alkyl and aryl derivatives

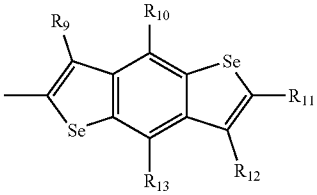

$R_9$ = H, Br, I alkyl and aryl derivatives
$R_{10}$ = H, Br, I alkyl and aryl derivatives
$R_{11}$ = H, Br, I alkyl and aryl derivatives
$R_{12}$ = H, Br, I alkyl and aryl derivatives
$R_{13}$ = H, Br, I alkyl and aryl derivatives

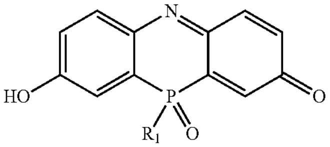

$R_1$ = 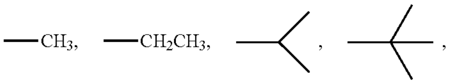

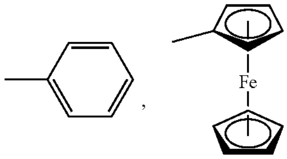

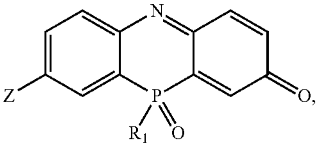

$R_1$ = 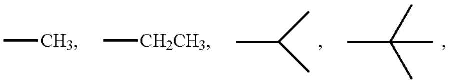

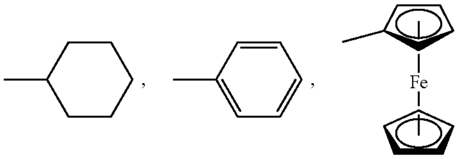

Z = 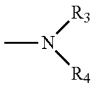 ($R_3$, $R_4$ = alkyl, aryl derivatives),

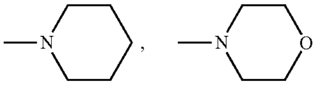

-continued

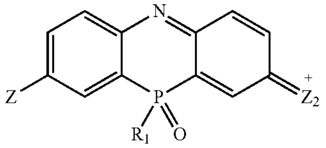

$R_1$ = —$CH_3$,

—$CH_2CH_3$,

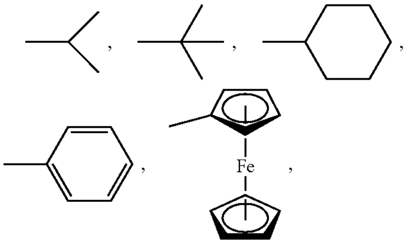

$Z_1$ =

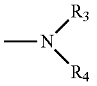

($R_3$, $R_4$ = alkyl, aryl derivatives),

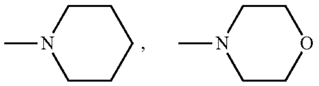

$Z_2$ =

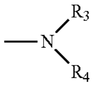

($R_3$, $R_4$ = alkyl, aryl derivatives),

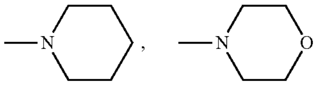

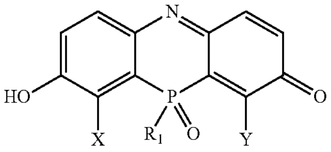

$R_1$ = —$CH_3$,

—$CH_2CH_3$,

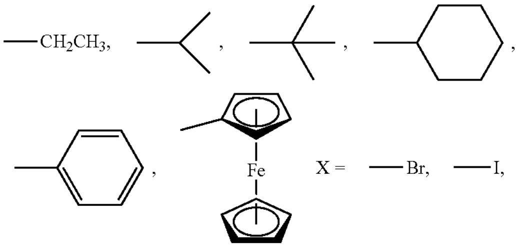

X = —Br, —I,

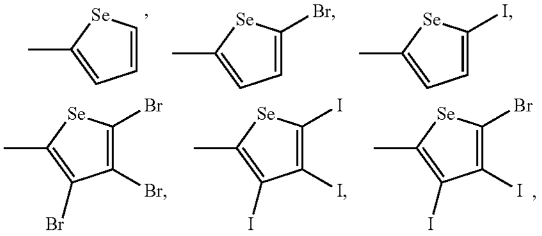

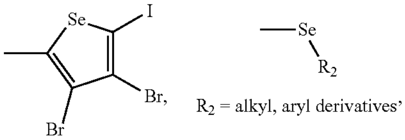

$R_2$ = alkyl, aryl derivatives'

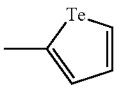

-continued

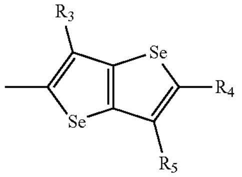

$R_3$ = H, Br, I alkyl and aryl derivatives
$R_4$ = H, Br, I alkyl and aryl derivatives
$R_5$ = H, Br, I alkyl and aryl derivatives

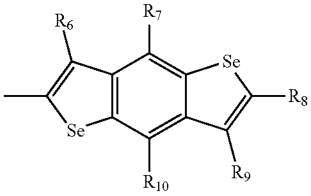

$R_6$ = H, Br, I alkyl and aryl derivatives
$R_7$ = H, Br, I alkyl and aryl derivatives
$R_8$ = H, Br, I alkyl and aryl derivatives
$R_9$ = H, Br, I alkyl and aryl derivatives
$R_{10}$ = H, Br, I alkyl and aryl derivatives

Y =

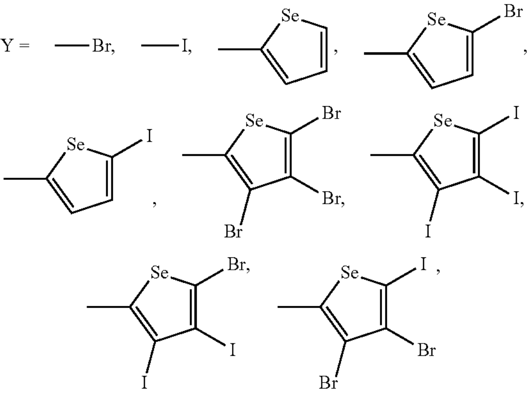

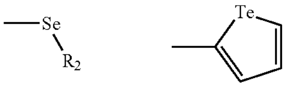

$R_2$ = alkyl, aryl derivatives,

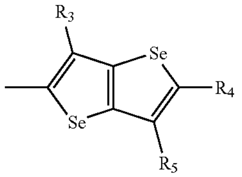

$R_3$ = H, Br, I alkyl and aryl derivatives
$R_4$ = H, Br, I alkyl and aryl derivatives
$R_5$ = H, Br, I alkyl and aryl derivatives

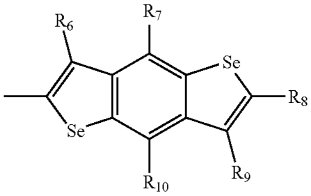

$R_6$ = H, Br, I alkyl and aryl derivatives
$R_7$ = H, Br, I alkyl and aryl derivatives
$R_8$ = H, Br, I alkyl and aryl derivatives
$R_9$ = H, Br, I alkyl and aryl derivatives
$R_{10}$ = H, Br, I alkyl and aryl derivatives -continued

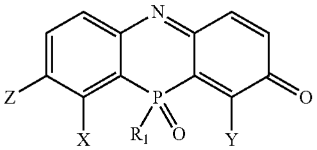

$R_1$ = —$CH_3$,

—$CH_2CH_3$, 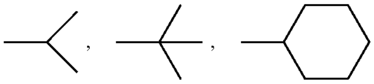

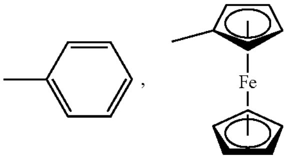

$Z_1$ = 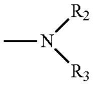 ($R_2$, $R_3$ = alkyl, aryl derivatives),

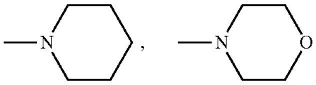

X = —Br, —I, 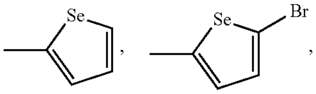

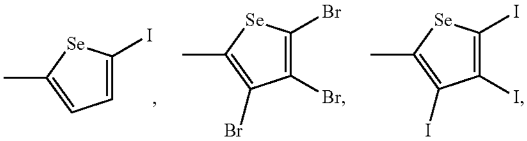

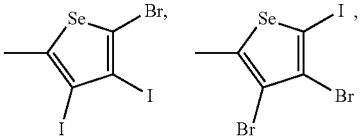

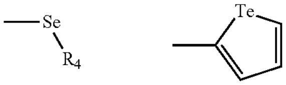

$R_4$ = alkyl, aryl derivatives,

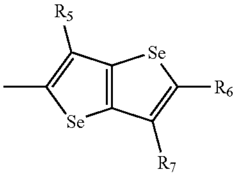

$R_5$ = H, Br, I alkyl and aryl derivatives
$R_6$ = H, Br, I alkyl and aryl derivatives
$R_7$ = H, Br, I alkyl and aryl derivatives

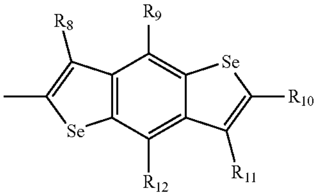

$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives
$R_{12}$ = H, Br, I alkyl and aryl derivatives Y = —Br, —I, 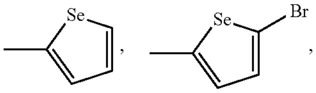

-continued

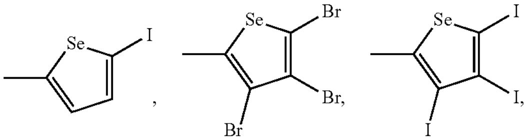

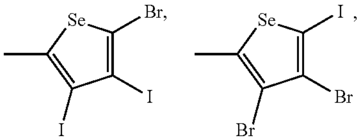

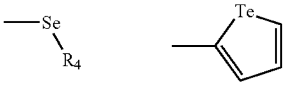

$R_4$ = alkyl, aryl derivatives,

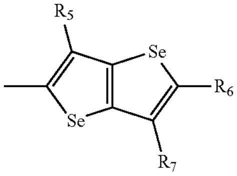

$R_5$ = H, Br, I alkyl and aryl derivatives
$R_6$ = H, Br, I alkyl and aryl derivatives
$R_7$ = H, Br, I alkyl and aryl derivatives

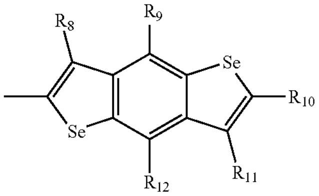

$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives
$R_{12}$ = H, Br, I alkyl and aryl derivatives

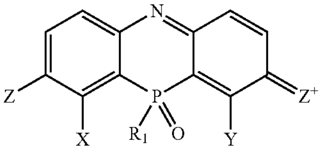

$R_1$ = —$CH_3$,

—$CH_2CH_3$, 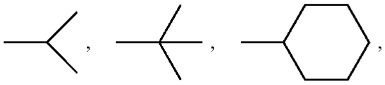

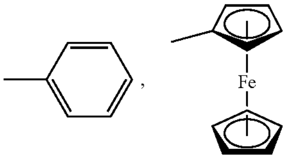

$Z_1$ = 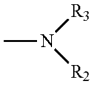 ($R_2$, $R_3$ = alkyl, aryl derivatives),

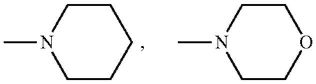

$Z_2$ = 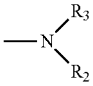 ($R_2$, $R_3$ = alkyl, aryl derivatives),

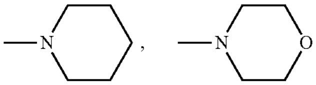

-continued

X = 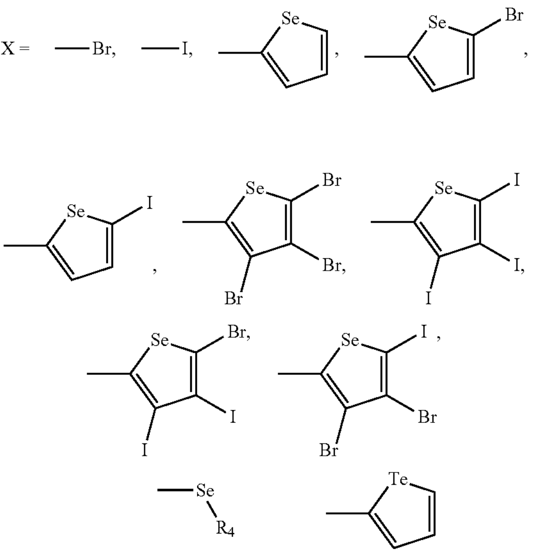

$R_4$ = alkyl, aryl derivatives,

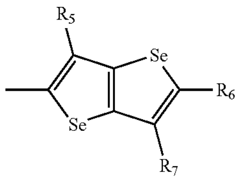

$R_5$ = H, Br, I alkyl and aryl derivatives
$R_6$ = H, Br, I alkyl and aryl derivatives
$R_7$ = H, Br, I alkyl and aryl derivatives

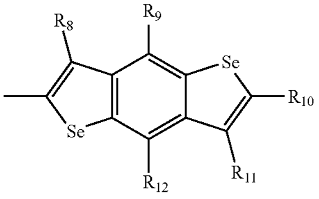

$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives
$R_{12}$ = H, Br, I alkyl and aryl derivatives Y = 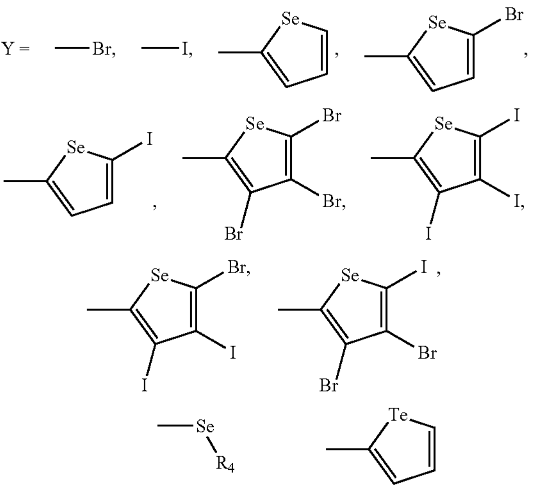

$R_4$ = alkyl, aryl derivatives,

-continued

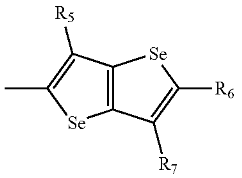

$R_5$ = H, Br, I alkyl and aryl derivatives
$R_6$ = H, Br, I alkyl and aryl derivatives
$R_7$ = H, Br, I alkyl and aryl derivatives

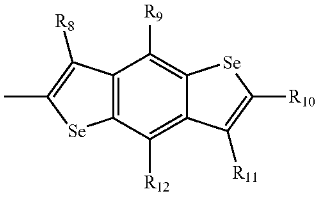

$R_8$ = H, Br, I alkyl and aryl derivatives
$R_9$ = H, Br, I alkyl and aryl derivatives
$R_{10}$ = H, Br, I alkyl and aryl derivatives
$R_{11}$ = H, Br, I alkyl and aryl derivatives
$R_{12}$ = H, Br, I alkyl and aryl derivatives Synthesized Compounds for Use in Photodynamic Therapy of Cancer:

Compound 1

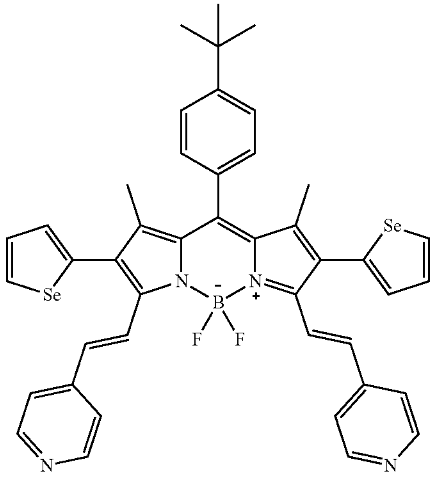

-continued
Compound 2
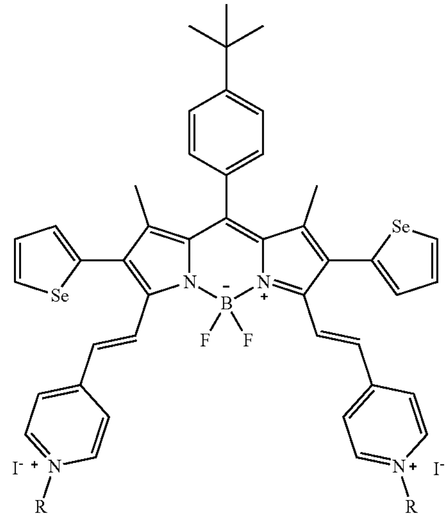
R = $CH_3$, $(CH_2)_nCH_3$ n = 1 to 10
Compound 3
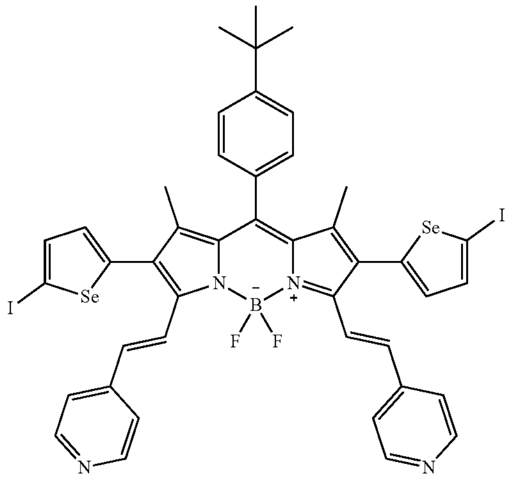
Compound 4
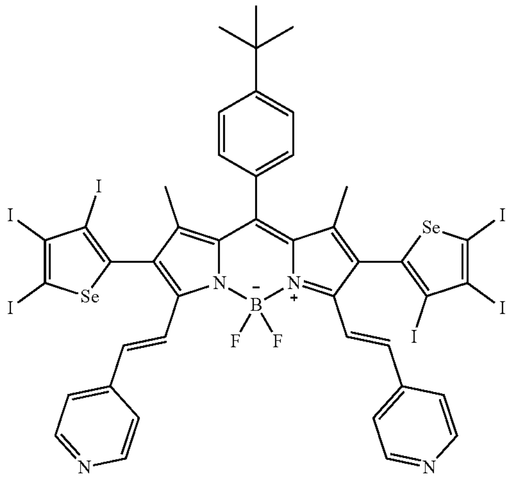
-continued
Compound 5
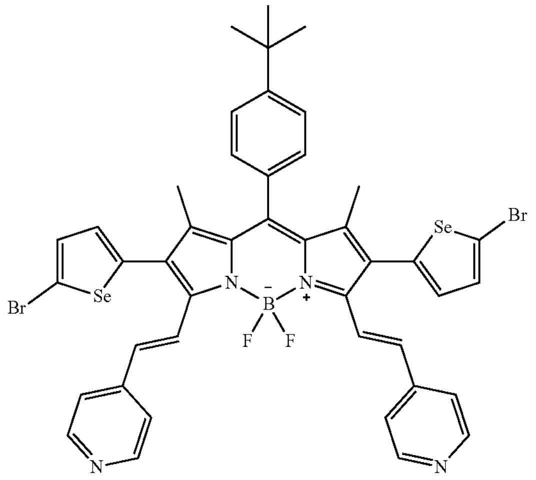
Compound 6
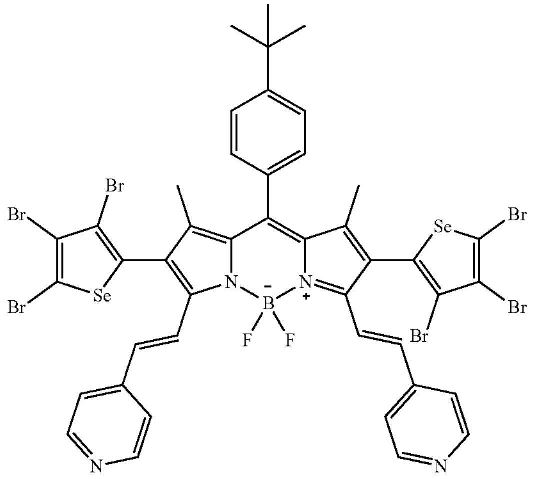
Compound 7
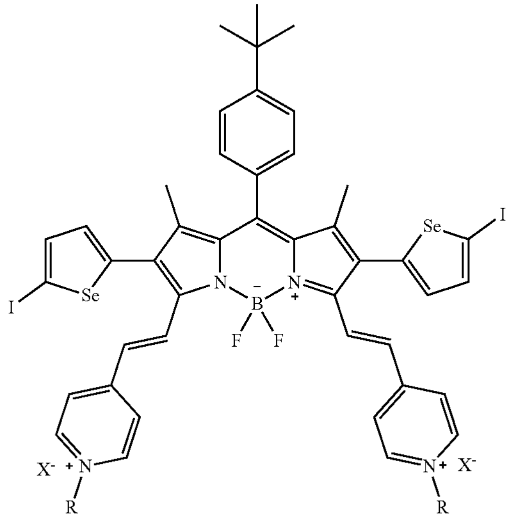
R = $CH_3$, $(CH_2)_nCH_3$ n = 1 to 10
X = I, Br -continued
Compound 8
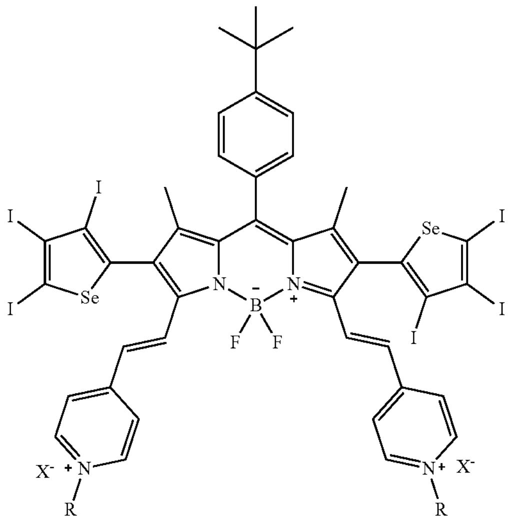
R = $CH_3$, $(CH_2)_nCH_3$ n = 1 to 10
X = I, Br
Compound 9
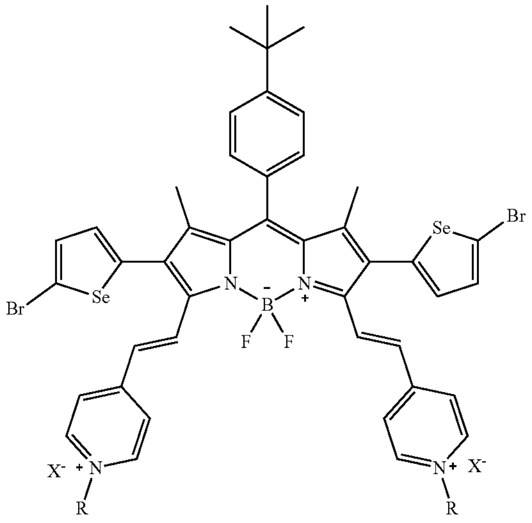
R = $CH_3$, $(CH_2)_nCH_3$ n = 1 to 10
X = I, Br
-continued
Compound 10
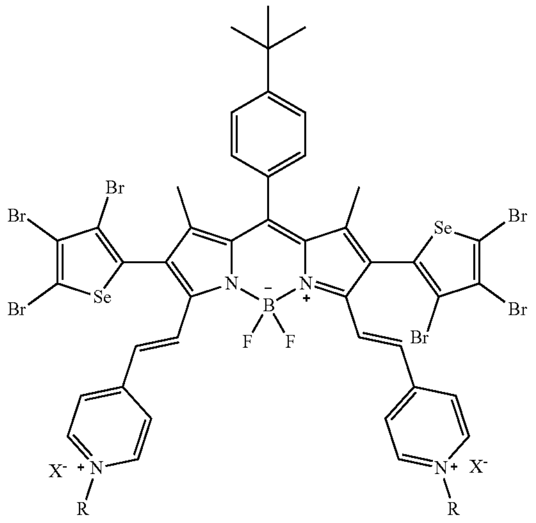
R = $CH_3$, $(CH_2)_nCH_3$ n = 1 to 10
X = I, Br
Compound 11
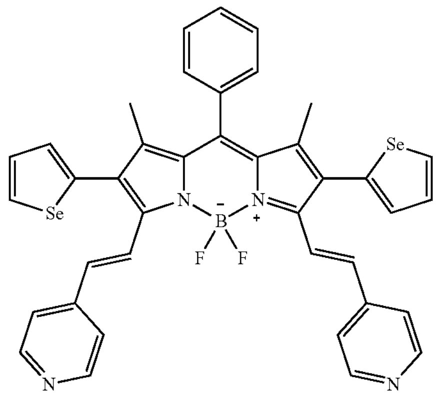
Compound 12
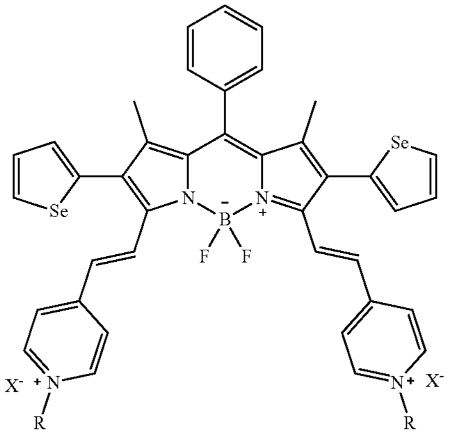
R = $CH_3$, $(CH_2)_nCH_3$ n = 1 to 10
X = I, Br -continued
Compound 13
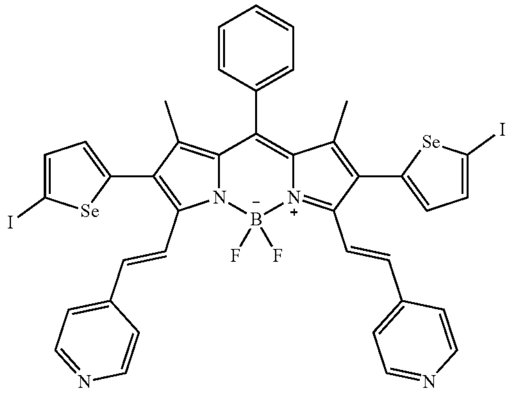
Compound 14
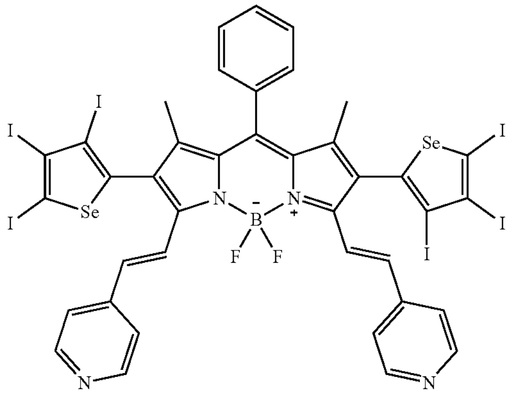
Compound 15
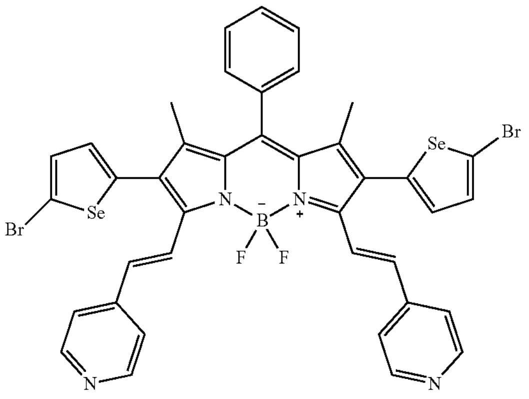
-continued
Compound 16
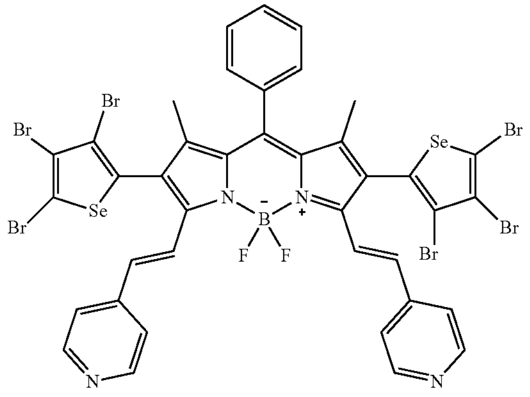
Compound 17
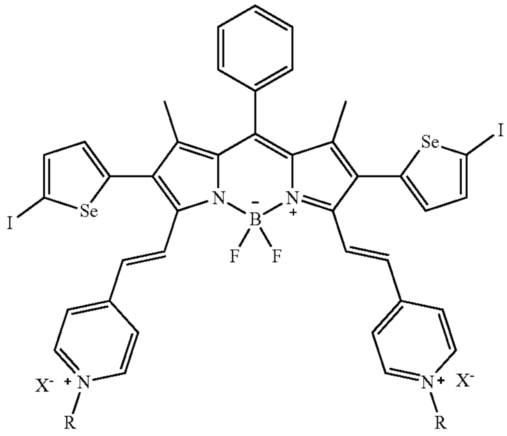
R = $CH_3$, $(CH_2)_nCH_3$ n = 1 to 10
X = I, Br
Compound 18
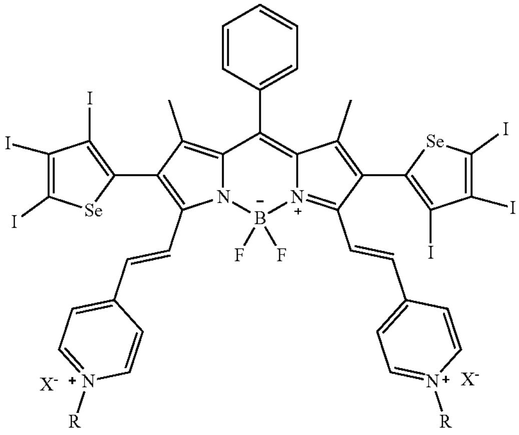
R = $CH_3$, $(CH_2)_nCH_3$ n = 1 to 10
X = I, Br -continued
Compound 19
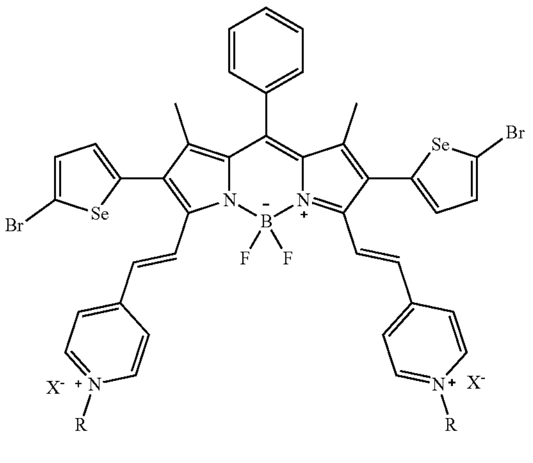
R = $CH_3$, $(CH_2)_nCH_3$ n = 1 to 10
X = I, Br
Compound 20
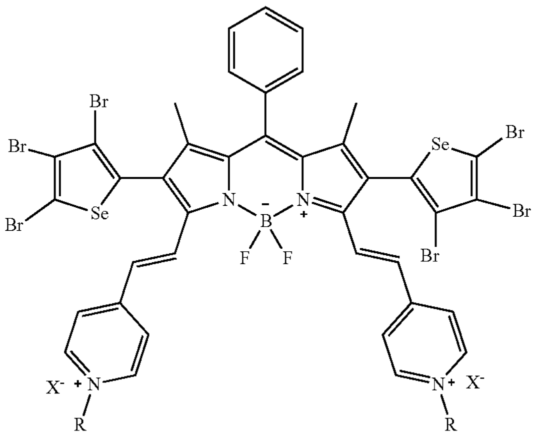
R = $CH_3$, $(CH_2)_nCH_3$ n = 1 to 10
X = I, Br
Compound 21
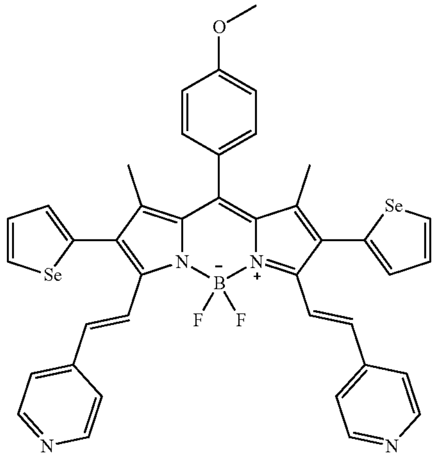
-continued
Compound 22
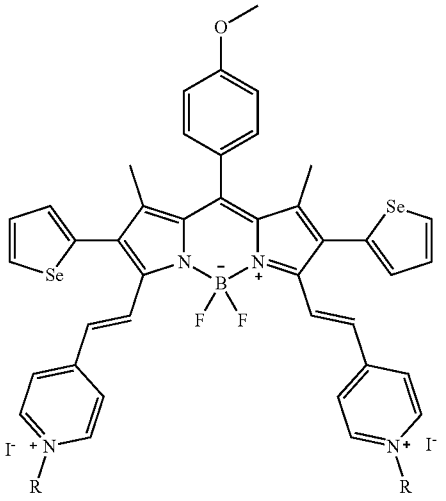
R = $CH_3$, $(CH_2)_nCH_3$ n = 1 to 10
X = I, Br
Compound 23
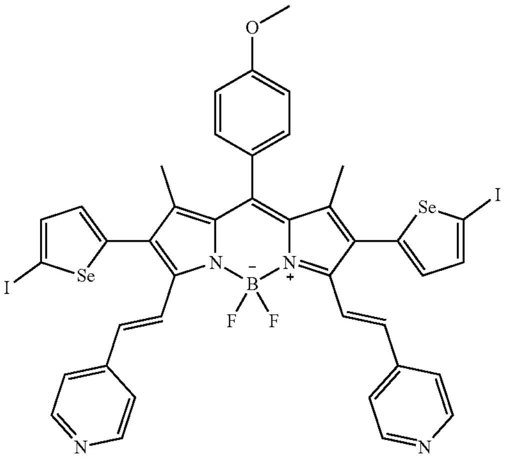
Compound 24
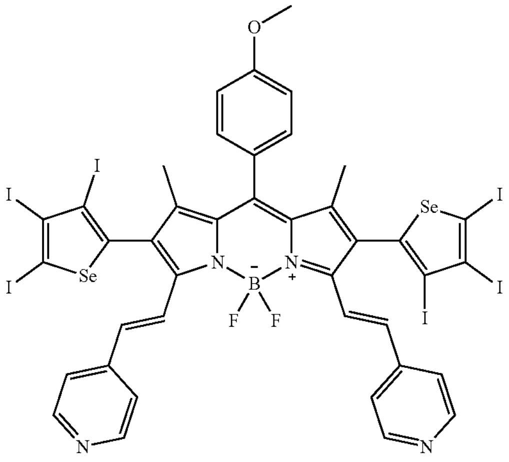

-continued
Compound 25
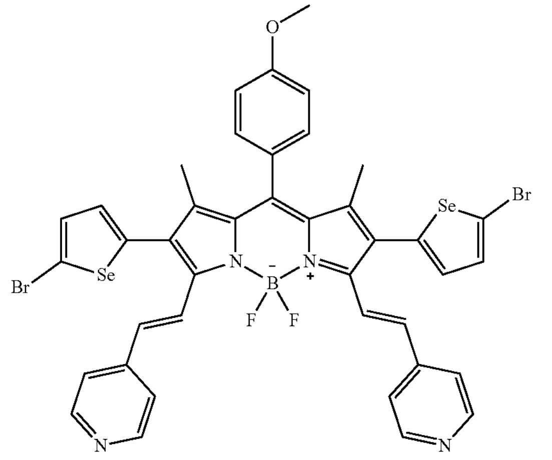
Compound 26
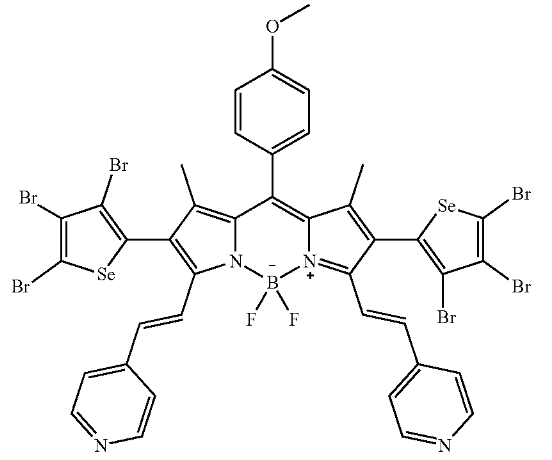
Compound 27
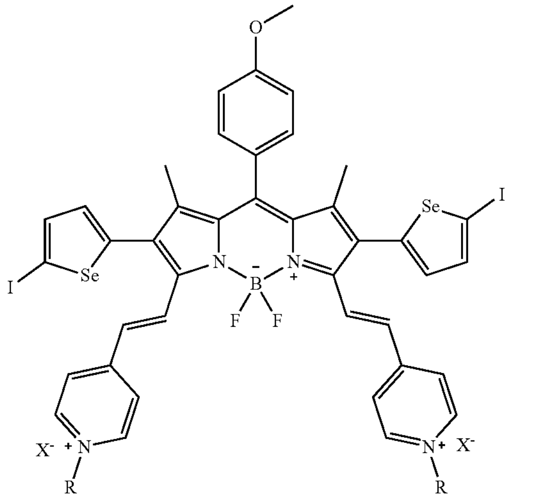
R = $CH_3$, $(CH_2)_nCH_3$ n = 1 to 10
X = I, Br
-continued
Compound 28
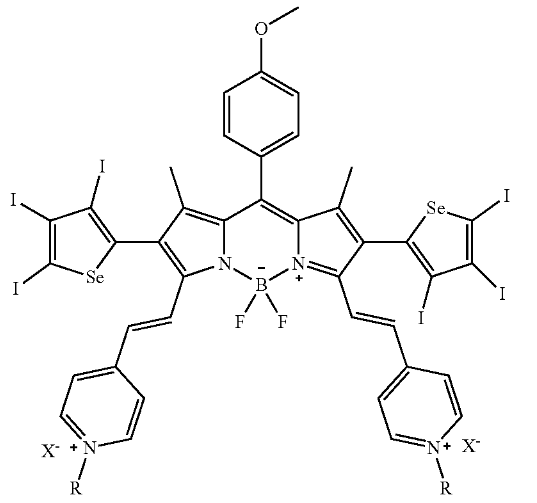
R = $CH_3$, $(CH_2)_nCH_3$ n = 1 to 10
X = I, Br
Compound 29
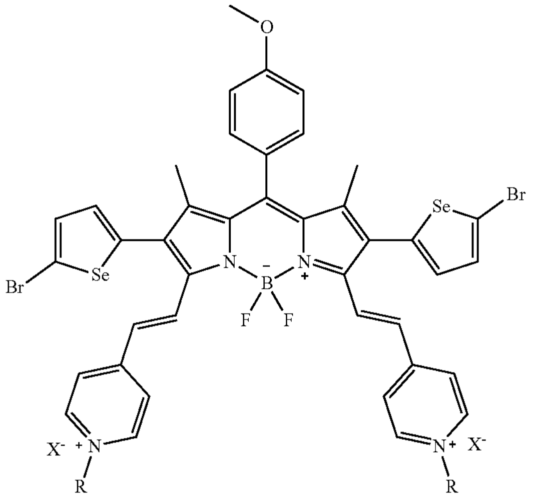
R = $CH_3$, $(CH_2)_nCH_3$ n = 1 to 10
X = I, Br -continued
Compound 30
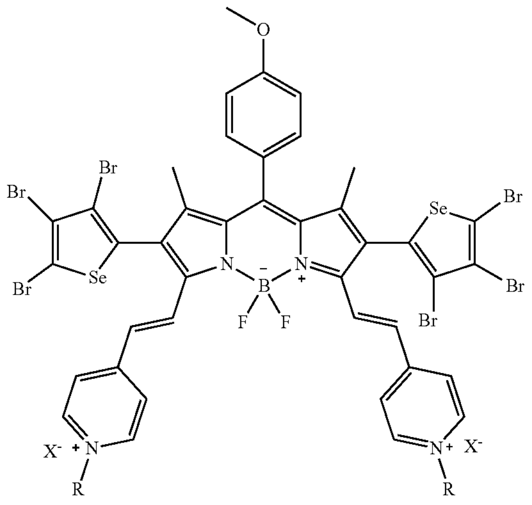
R = $CH_3$, $(CH_2)_nCH_3$ n = 1 to 10
X = I, Br
Compound 31
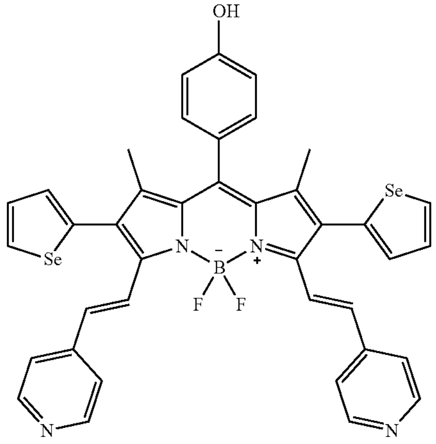
Compound 32
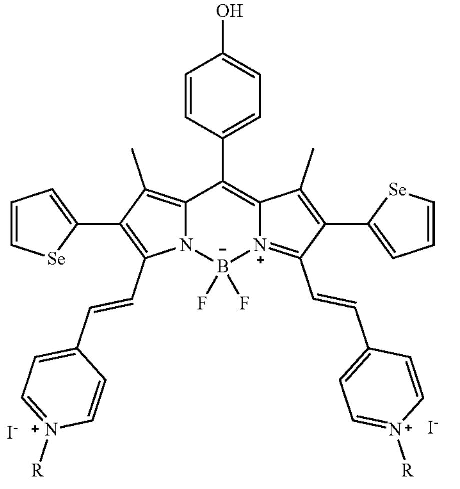
R = $CH_3$, $(CH_2)_nCH_3$ n = 1 to 10
X = I, Br
-continued
Compound 33
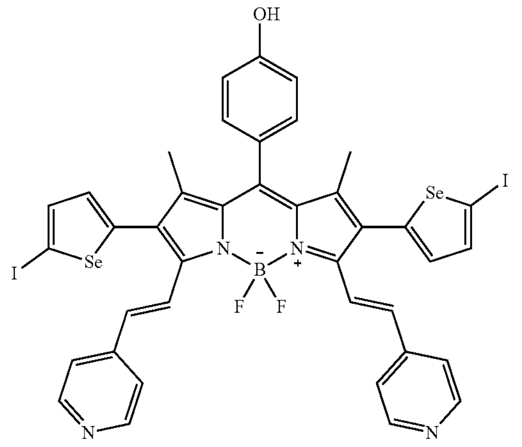
Compound 34
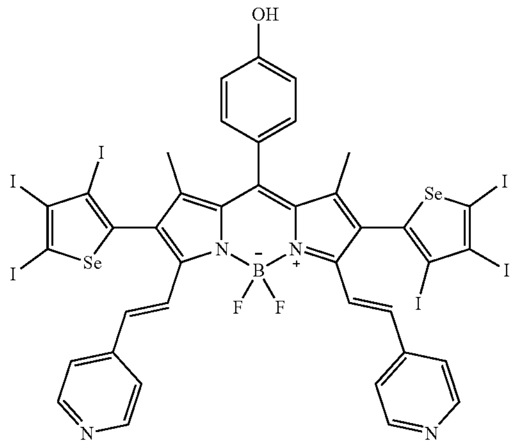
Compound 35
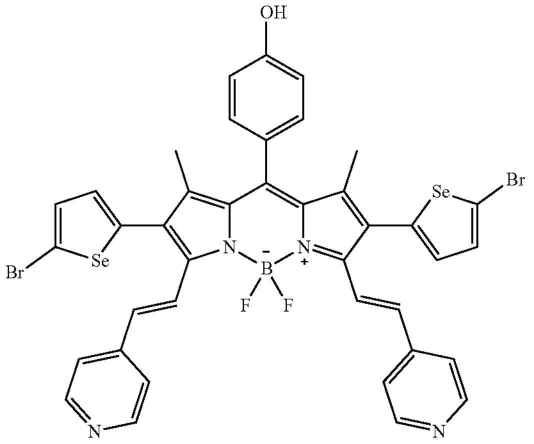

-continued
Compound 36
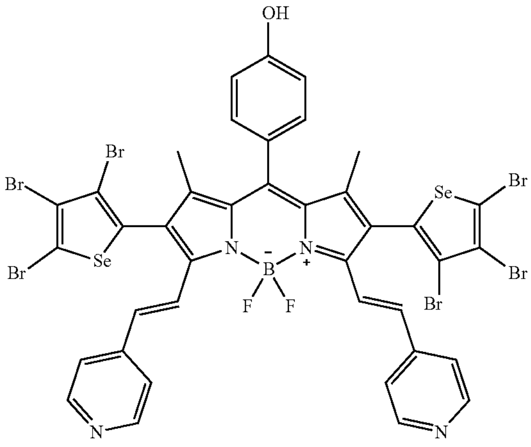
Compound 37
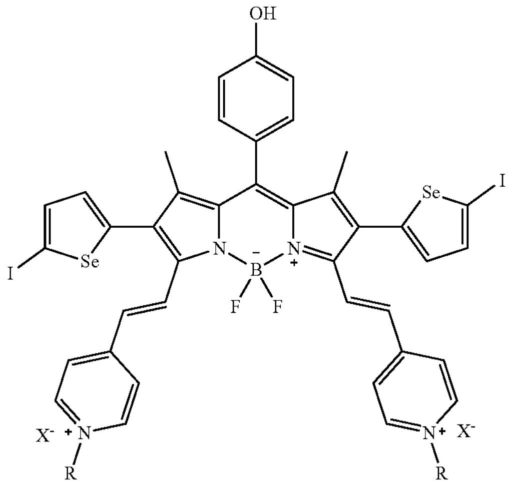
R = $CH_3$, $(CH_2)_nCH_3$ n = 1 to 10
X = I, Br
Compound 38
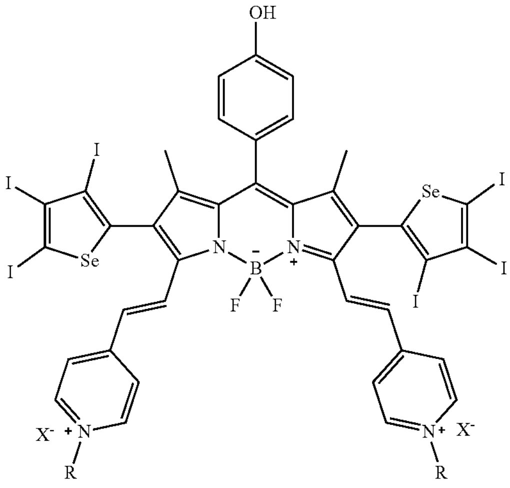
R = $CH_3$, $(CH_2)_nCH_3$ n = 1 to 10
X = I, Br
-continued
Compound 39
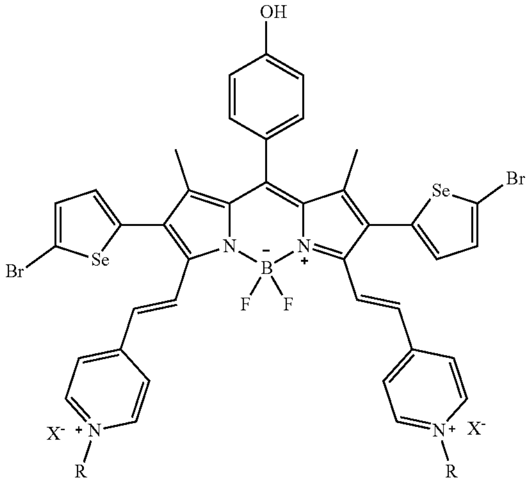
R = $CH_3$, $(CH_2)_nCH_3$ n = 1 to 10
X = I, Br
Compound 40
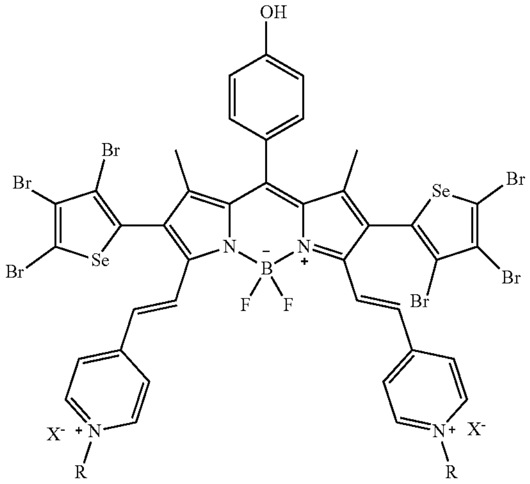
R = $CH_3$, $(CH_2)_nCH_3$ n = 1 to 10
X = I, Br
Compound 41
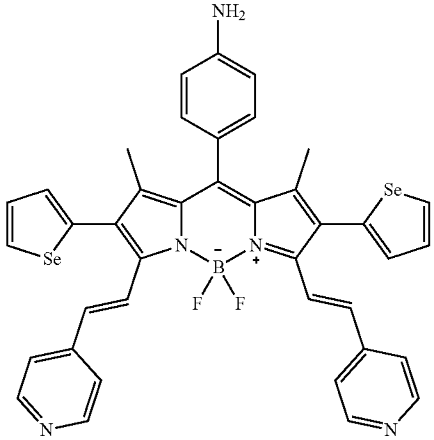

-continued
Compound 42
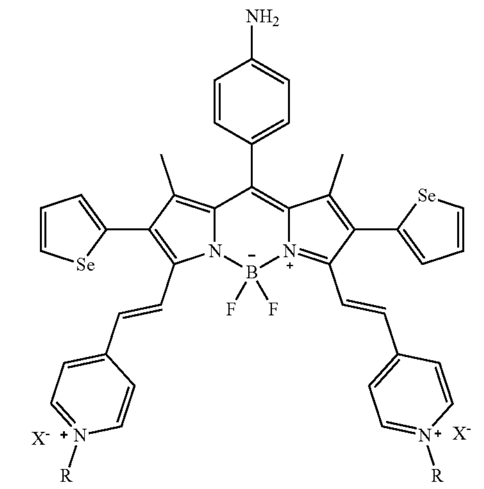
R = $CH_3$, $(CH_2)_nCH_3$ n = 1 to 10
X = I, Br
Compound 43
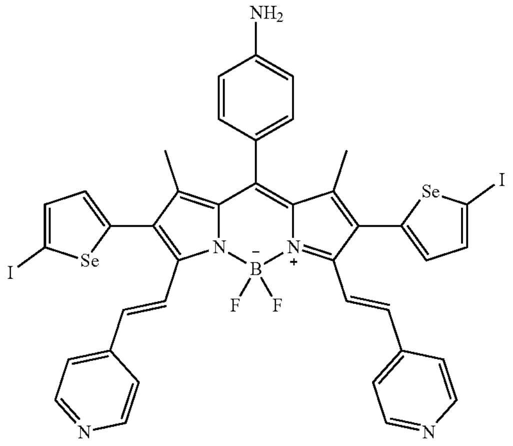
Compound 44
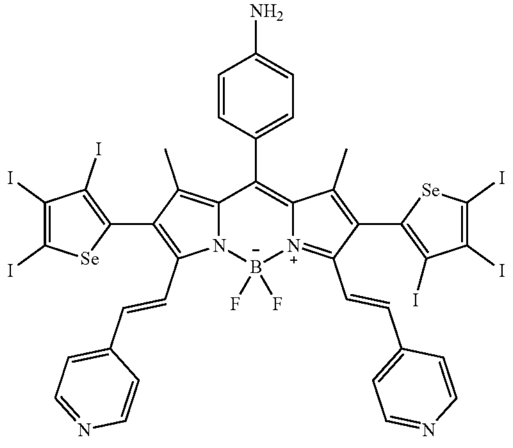
-continued
Compound 45
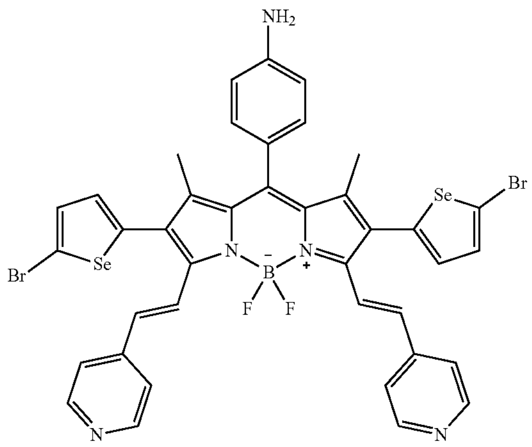
Compound 46
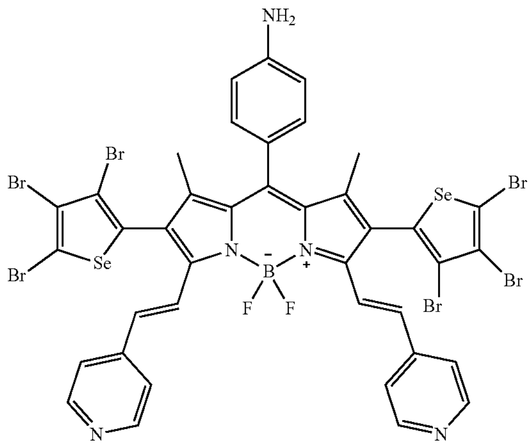
Compound 47
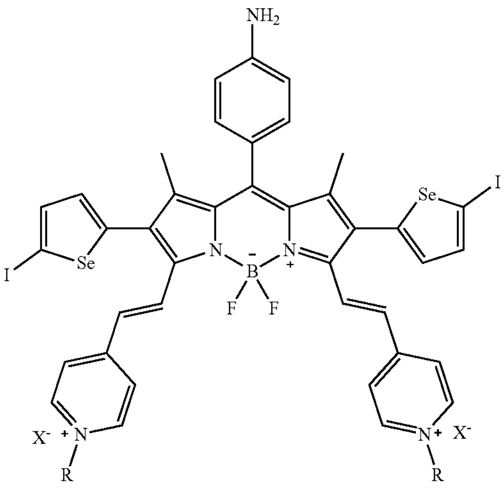
R = $CH_3$, $(CH_2)_nCH_3$ n = 1 to 10
X = I, Br -continued
Compound 48
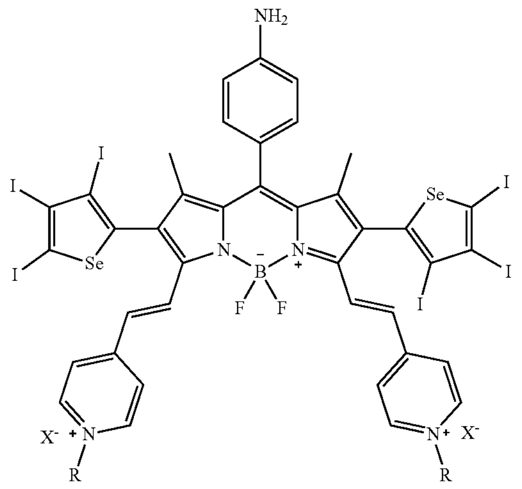
R = $CH_3$, $(CH_2)_nCH_3$ n = 1 to 10
X = I, Br
Compound 49
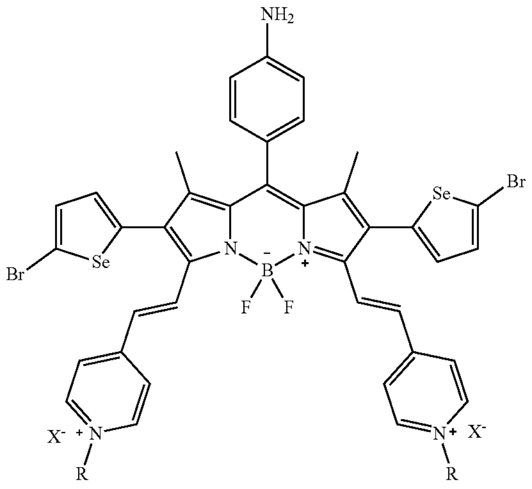
R = $CH_3$, $(CH_2)_nCH_3$ n = 1 to 10
X = I, Br
-continued
Compound 50
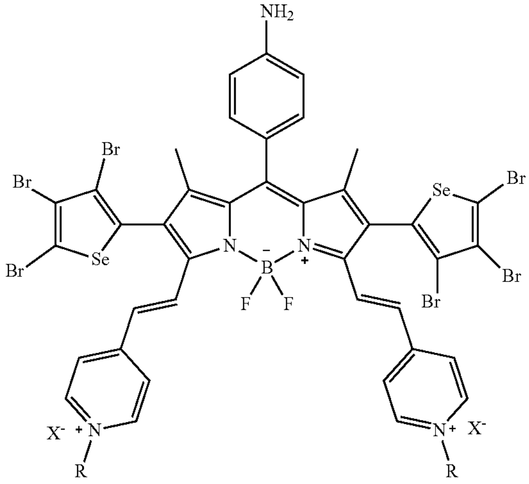
R = $CH_3$, $(CH_2)_nCH_3$ n = 1 to 10
X = I, Br
Compound 51
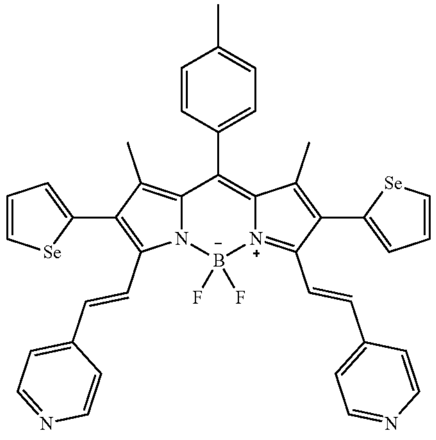
Compound 52
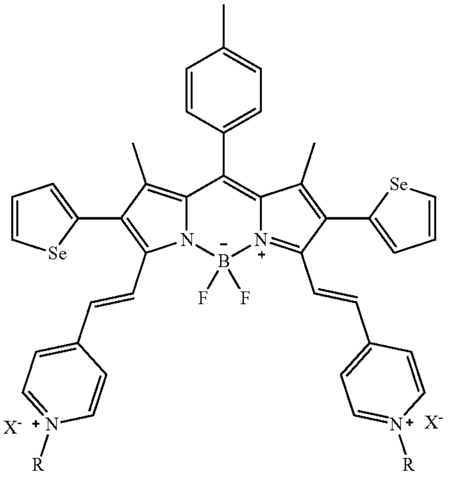
R = $CH_3$, $(CH_2)_nCH_3$ n = 1 to 10
X = I, Br -continued
Compound 53
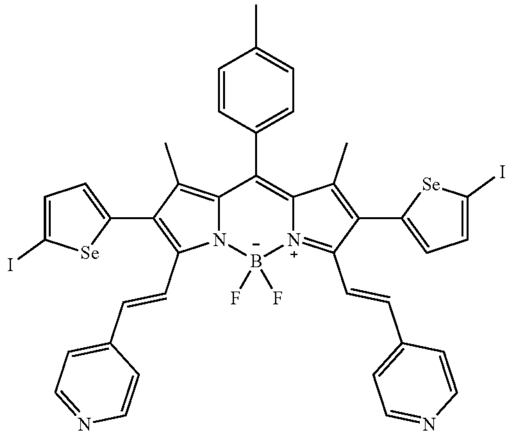
Compound 54
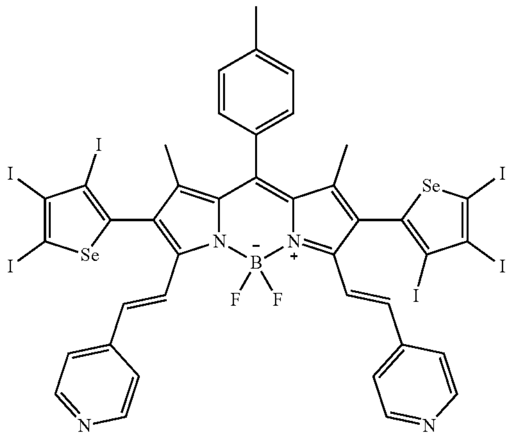
Compound 55
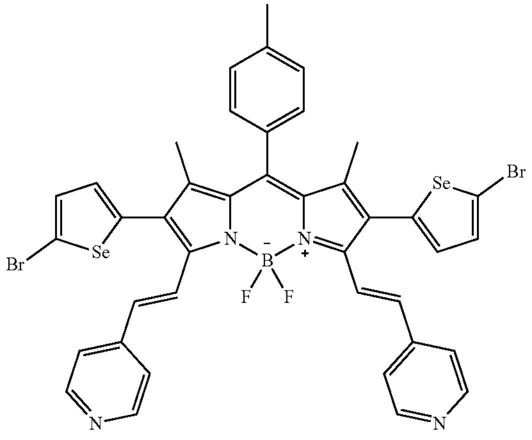
-continued
Compound 56
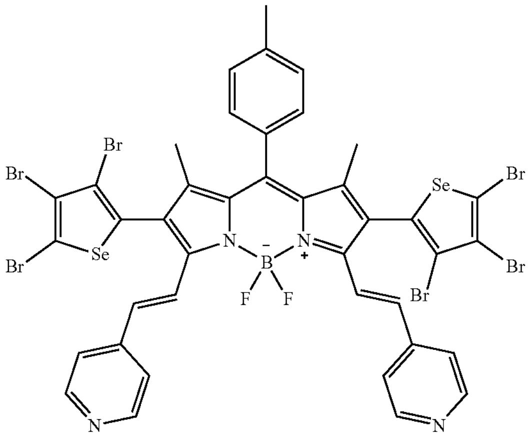
Compound 57
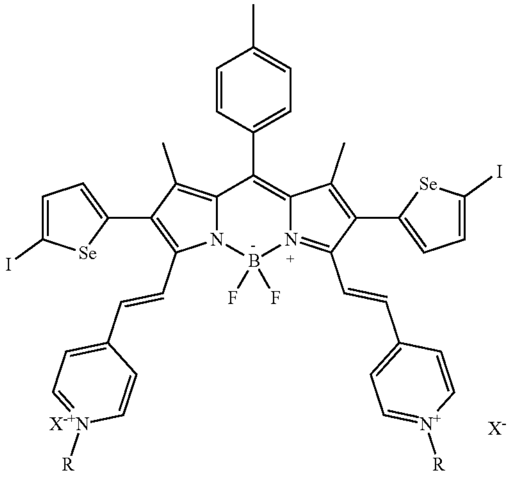
R = $CH_3$, $(CH_2)_nCH_3$
n = 1 to 10
X = I, Br Compound 58
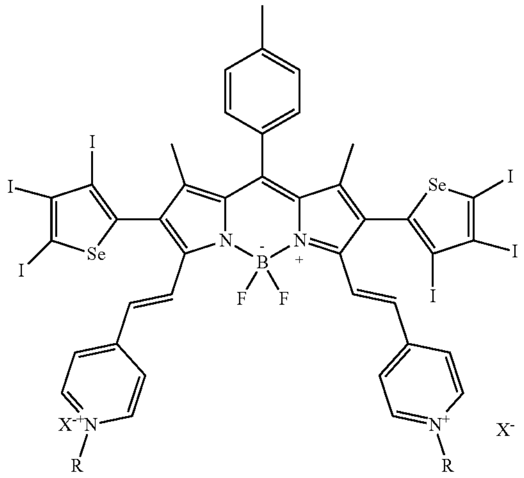
R = $CH_3$, $(CH_2)_nCH_3$
n = 1 to 10
X = I, Br
Compound 59
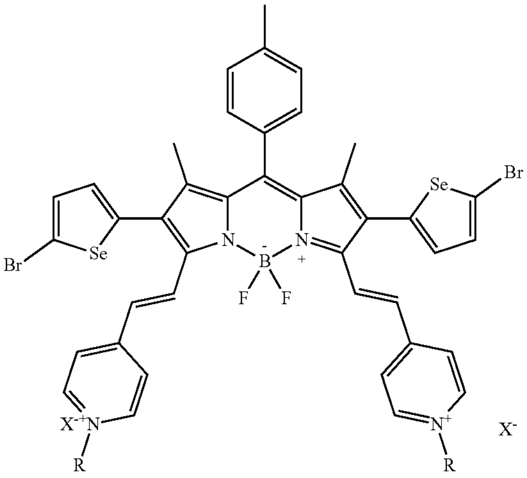
R = $CH_3$,
$(CH_2)_nCH_3$
n = 1 to 10
X = I, Br
Compound 60
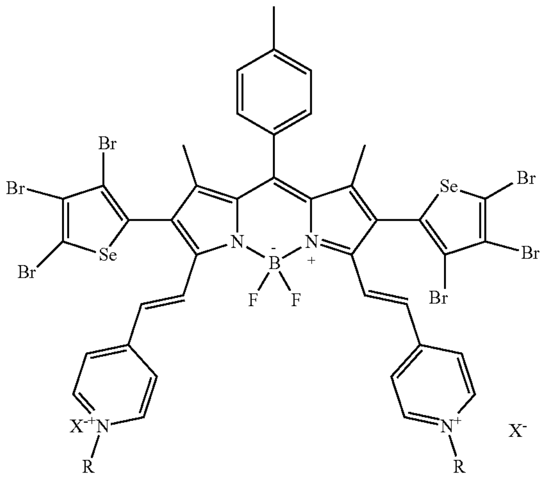
R = $CH_3$,
$(CH_2)_nCH_3$
n = 1 to 10
X = I, Br
Compound 61
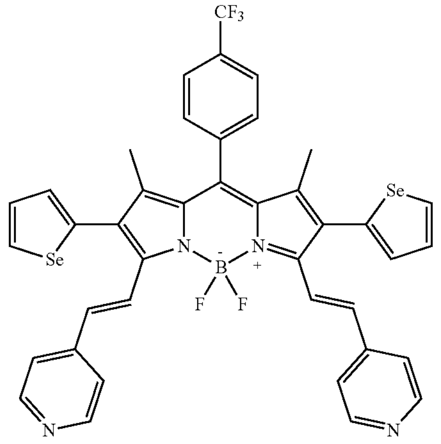
Compound 62
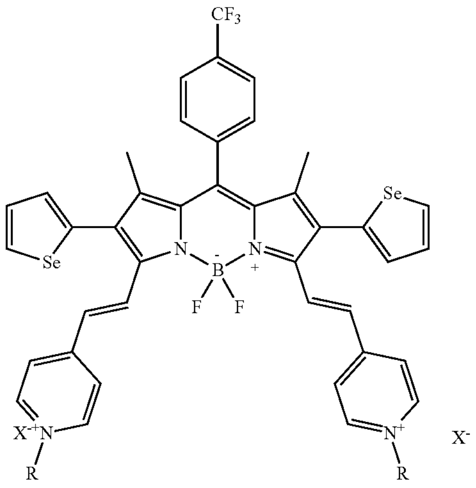
R = $CH_3$, $(CH_2)_nCH_3$
n = 1 to 10
X = I, Br -continued
Compound 63
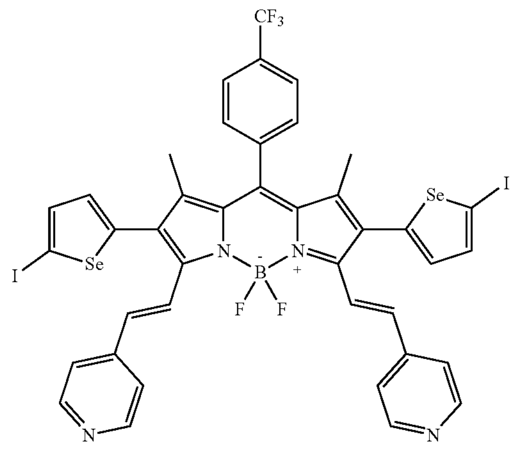
Compound 64
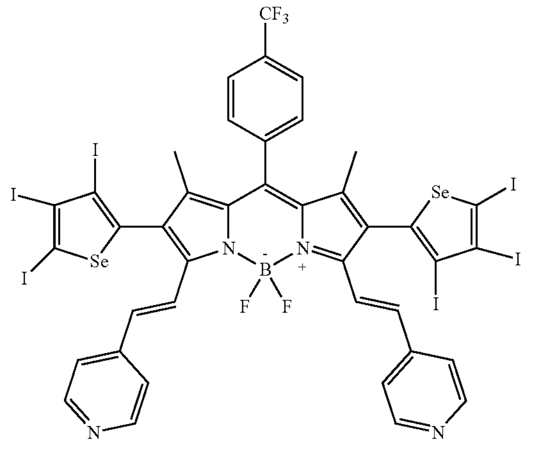
Compound 65
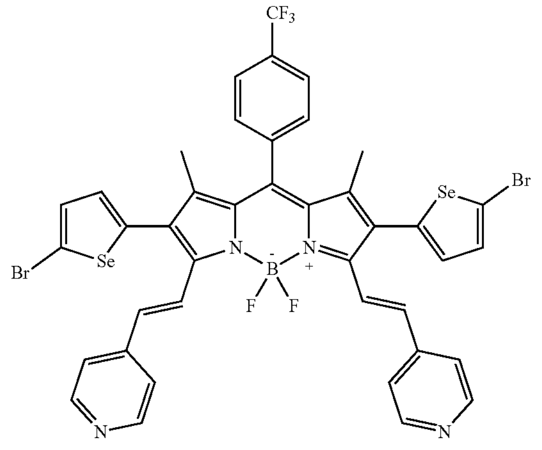
-continued
Compound 66
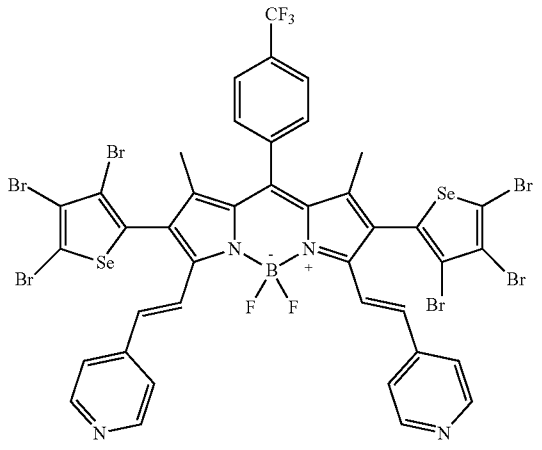
Compound 67
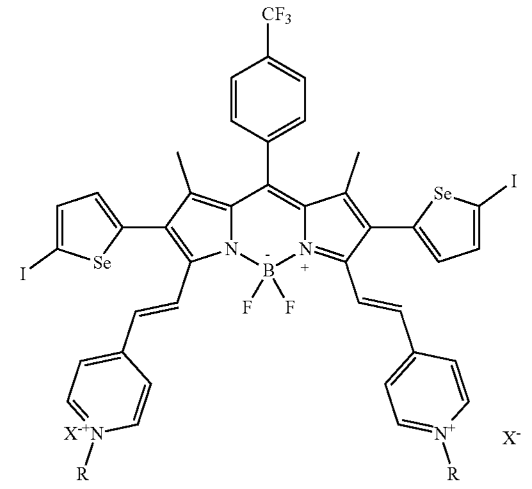
R = $CH_3$, $(CH_2)_nCH_3$
n = 1 to 10
X = I, Br
Compound 68
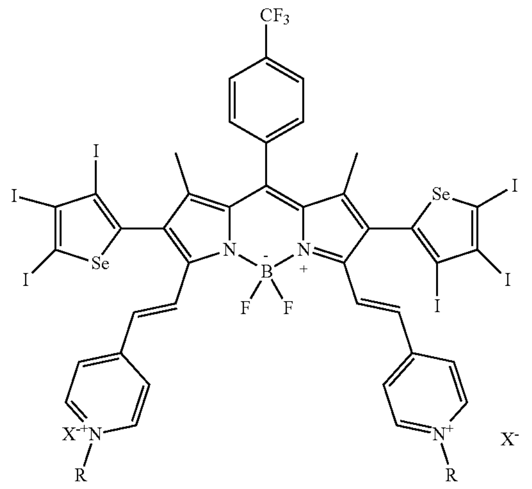
$R_5$ = $CH_3$, $(CH_2)n$
n = 2 to 10
X = I, Br -continued
Compound 69
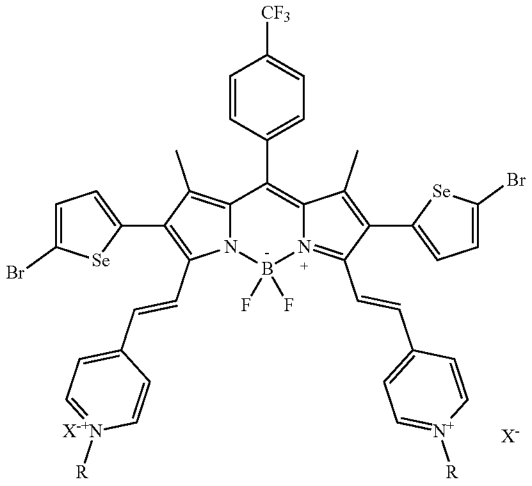
$R = CH_3, (CH_2)_nCH_3$
n = 1 to 10
X = I, Br
Compound 70
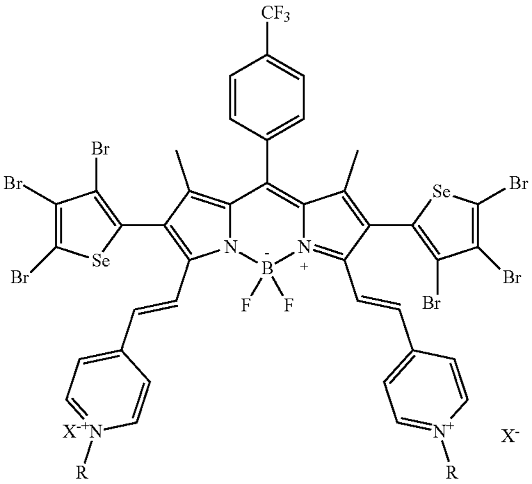
$R = CH_3, (CH_2)_nCH_3$
n = 1 to 10
X = I, Br
Compound 71
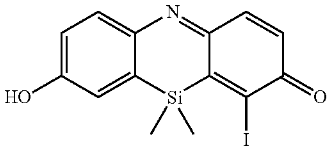
Compound 72
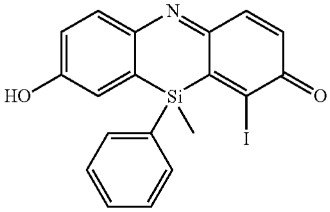
-continued
Compound 73
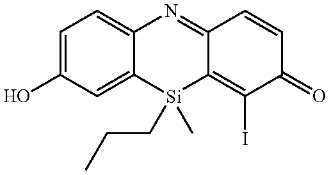
Compound 74
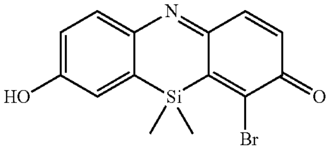
Compound 75
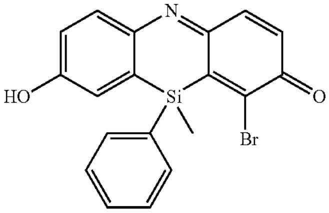
Compound 76
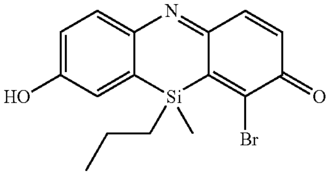
Compound 77
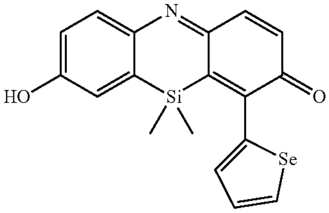
Compound 78
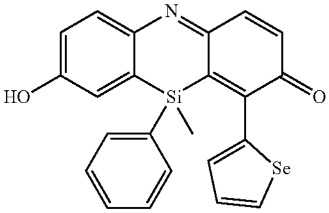
Compound 79
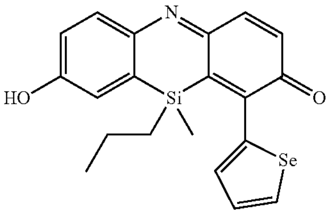
Compound 80
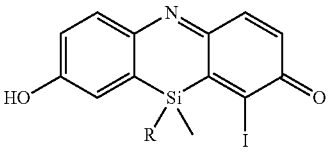
$R = -CH_2(CH_2)_{16}CH_3$ -continued
Compound 81
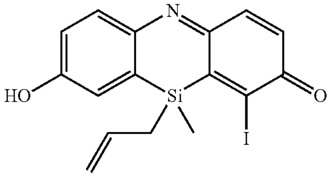
Compound 82
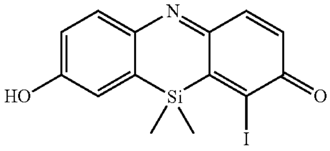
Compound 83
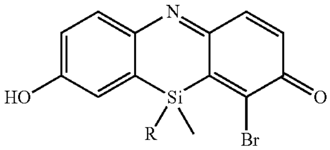
R = $-CH_2(CH_2)_{16}CH_3$
Compound 84
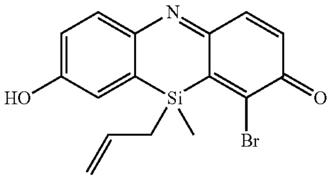
Compound 85
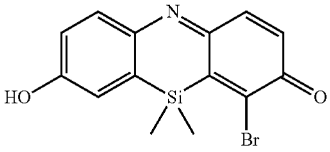
Compound 86
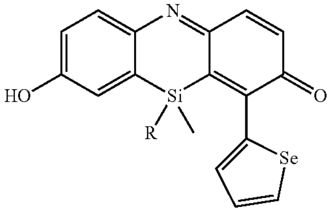
R = $-CH_2(CH_2)_{16}CH_3$
Compound 87
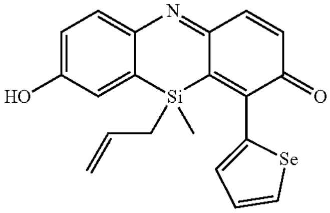
Compound 88
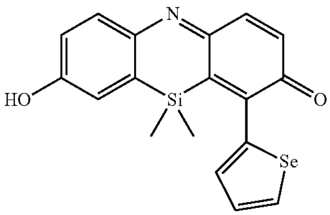
-continued
Compound 89
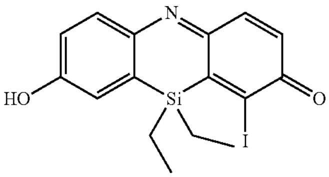
Compound 90
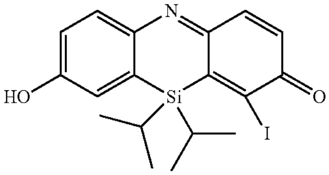
Compound 91
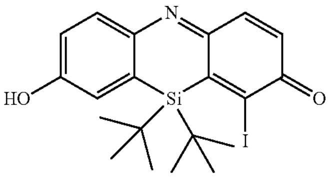
Compound 92
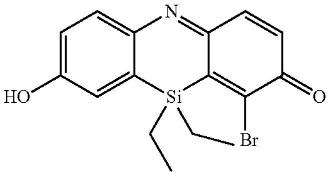
Compound 93
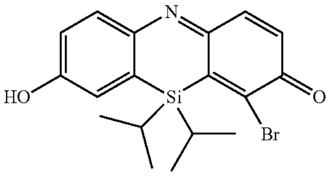
Compound 94
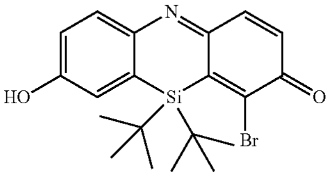
Compound 95
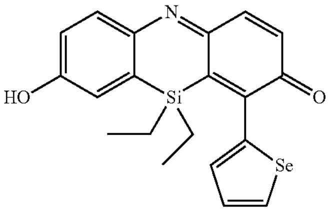
Compound 96
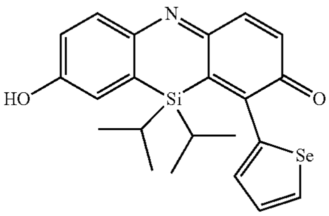

-continued
Compound 97
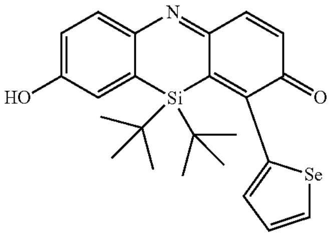
Compound 98
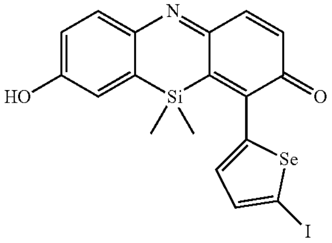
Compound 99
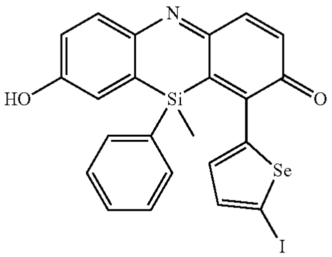
Compound 100
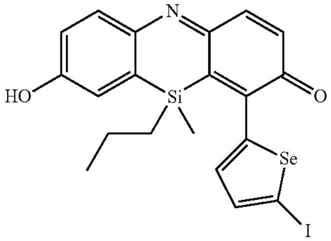
Compound 101
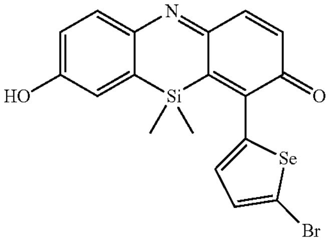
Compound 102
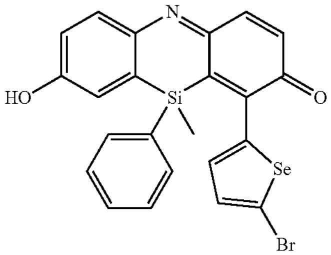
-continued
Compound 103
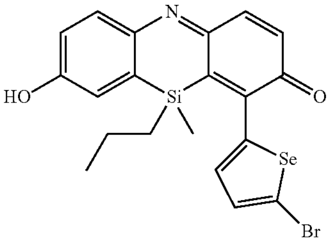
Compound 104
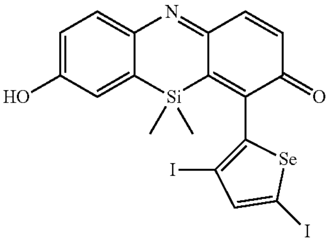
Compound 105
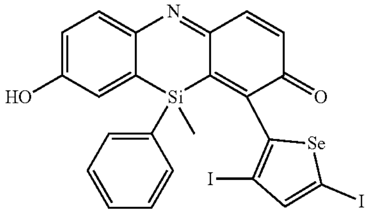
Compound 106
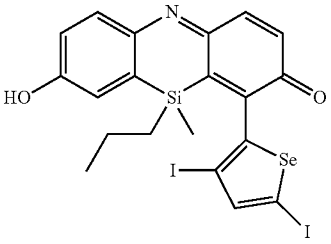
Compound 107
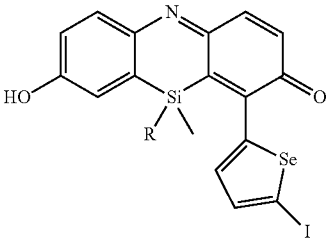
R = —$CH_2(CH_2)_{16}CH_3$
Compound 108
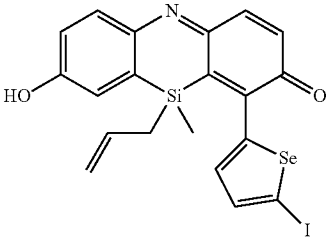

-continued
Compound 109
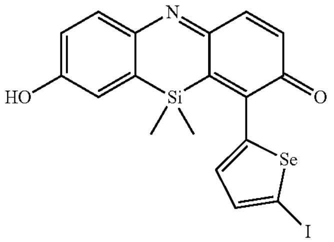
Compound 110
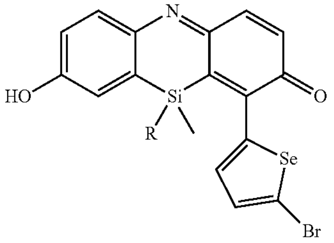
R = —$CH_2(CH_2)_{16}CH_3$
Compound 111
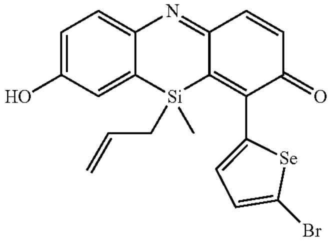
Compound 112
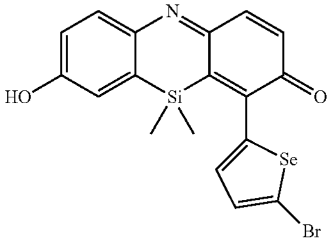
Compound 113
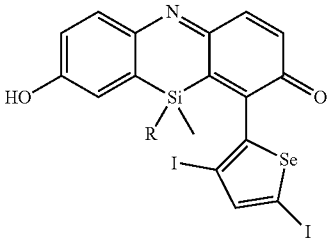
R = —$CH_2(CH_2)_{16}CH_3$
Compound 114
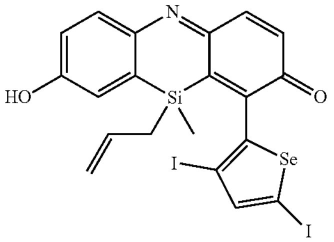
-continued
Compound 115
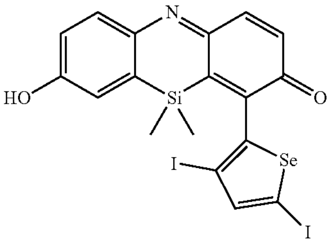
Compound 116
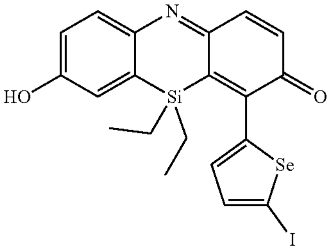
Compound 117
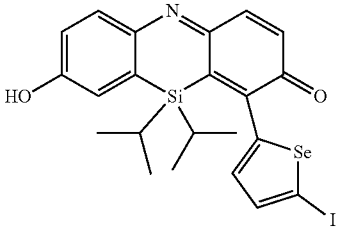
Compound 118
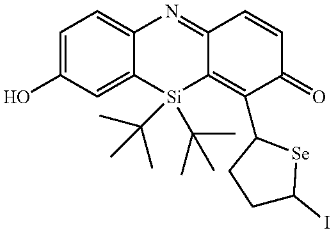
Compound 119
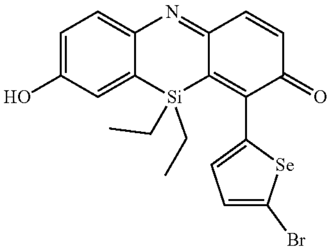
Compound 120
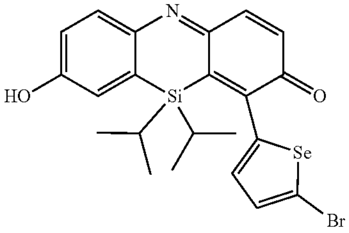

Compound 121
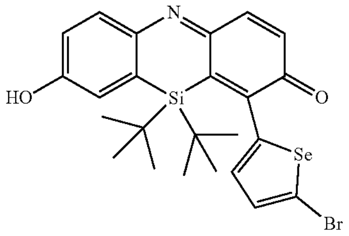
Compound 122
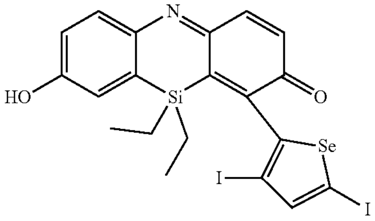
Compound 123
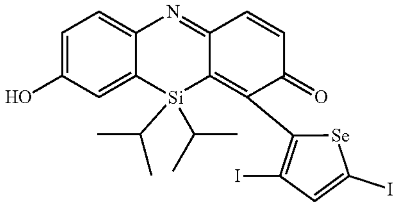
Compound 124
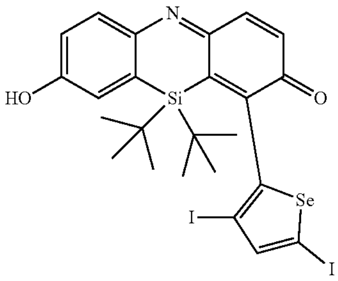
Compound 125
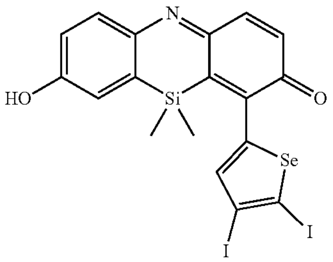
Compound 126
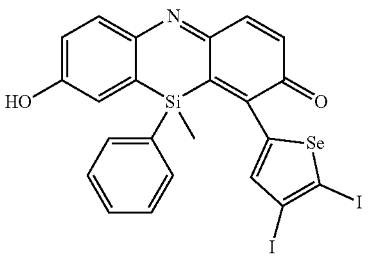
Compound 127
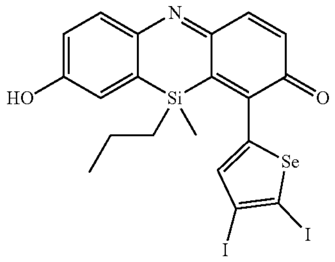
Compound 128
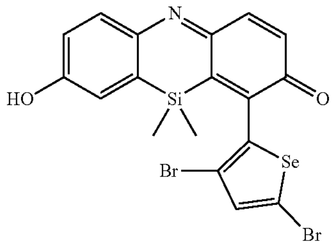
Compound 129
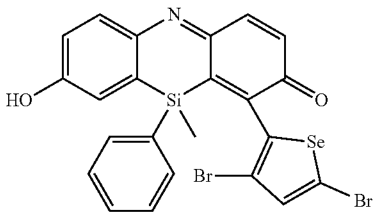
Compound 130
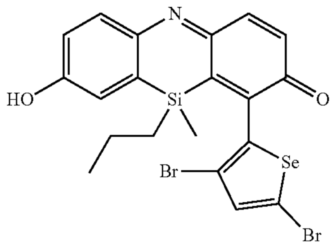
Compound 131
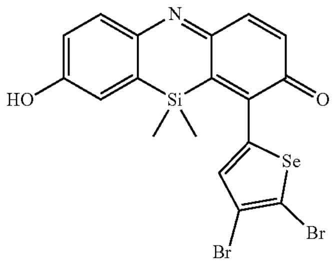
Compound 132
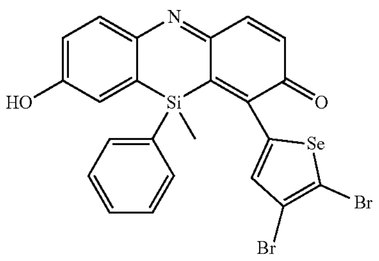

-continued
Compound 133
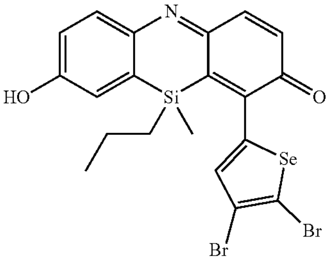
Compound 134
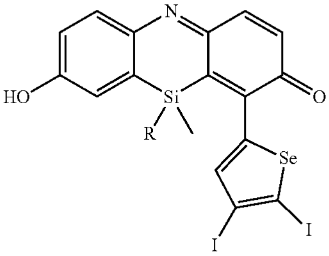
R = —$CH_2(CH_2)_{16}CH_3$
Compound 135
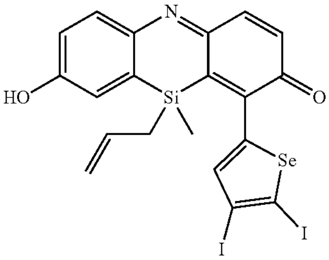
Compound 136
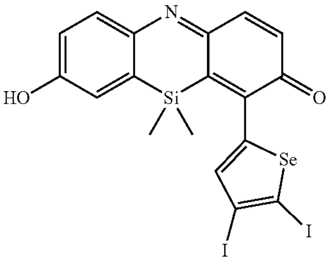
Compound 137
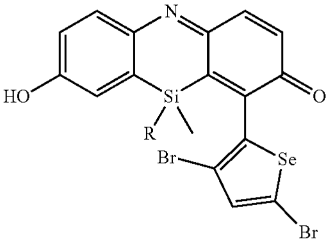
R = —$CH_2(CH_2)_{16}CH_3$
Compound 138
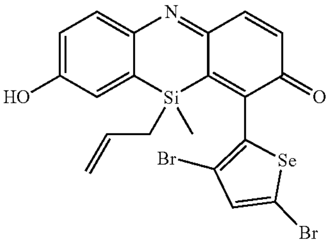
-continued
Compound 139
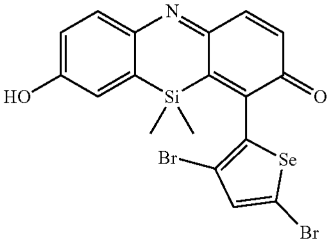
Compound 140
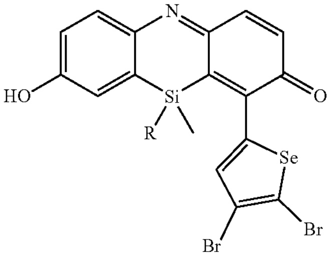
R = —$CH_2(CH_2)_{16}CH_3$
Compound 141
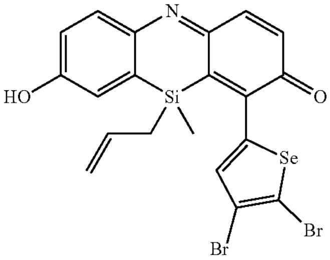
Compound 142
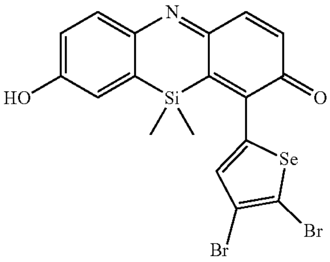
Compound 143
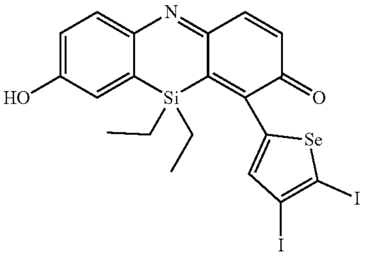
Compound 144
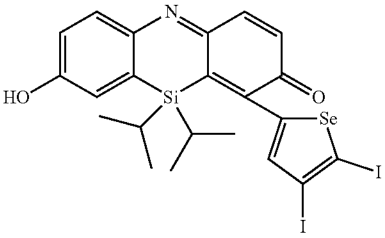

-continued
Compound 145
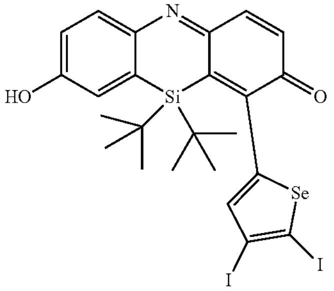
Compound 146
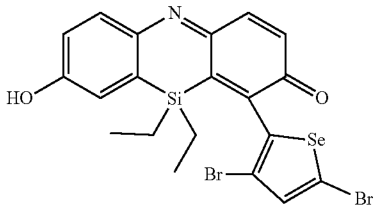
Compound 147
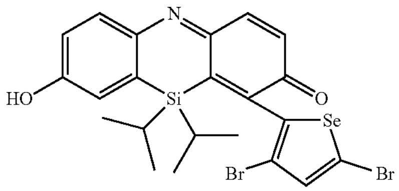
Compound 148
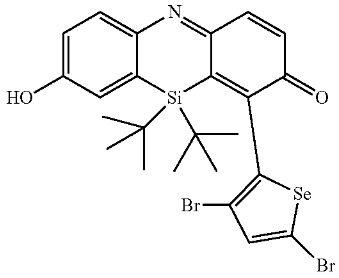
Compound 149
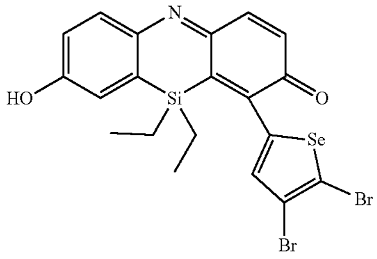
Compound 150
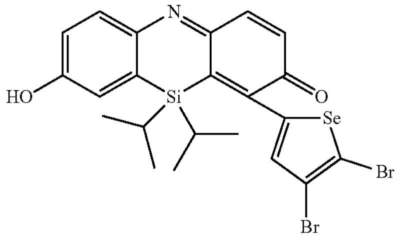
-continued
Compound 151
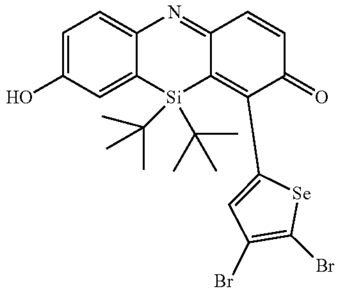
Compound 152
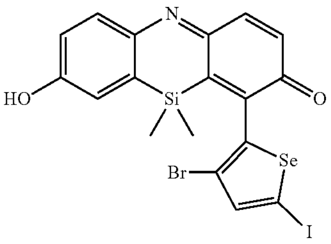
Compound 153
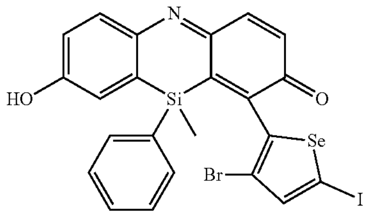
Compound 154
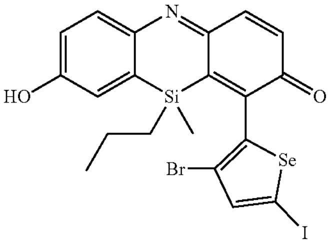
Compound 155
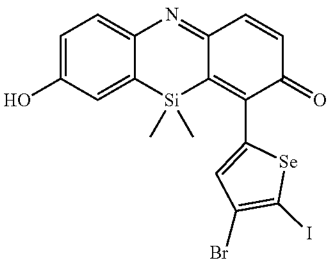
Compound 156
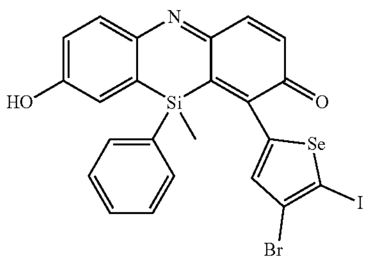

-continued
Compound 157
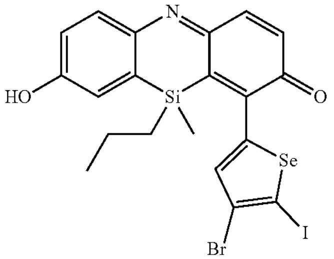
Compound 158
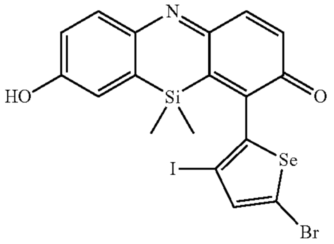
Compound 159
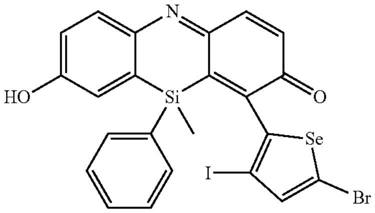
Compound 160
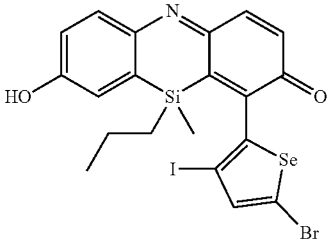
Compound 161
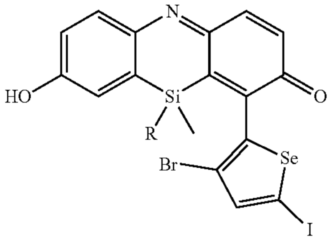
R = $-CH_2(CH_2)_{16}CH_3$
Compound 162
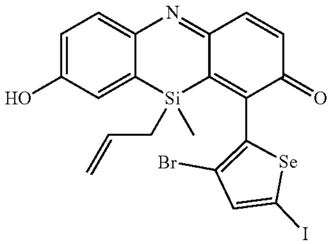
-continued
Compound 163
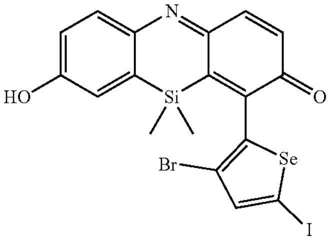
Compound 164
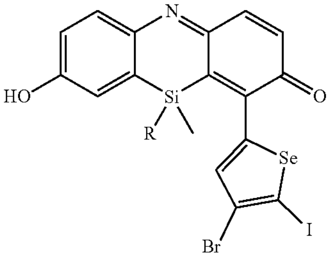
R = $-CH_2(CH_2)_{16}CH_3$
Compound 165
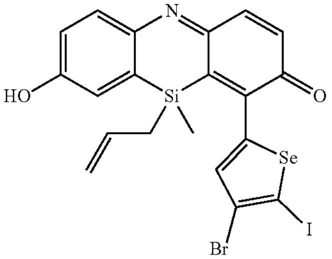
Compound 166
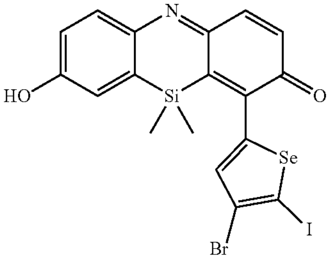
Compound 167
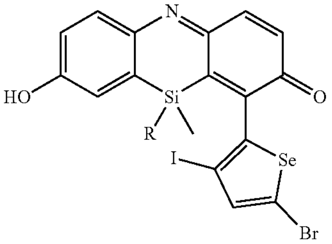
R = $-CH_2(CH_2)_{16}CH_3$
Compound 168
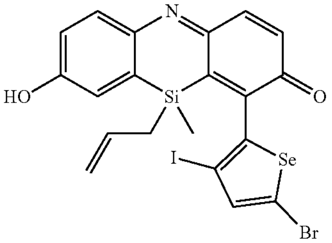

Compound 169
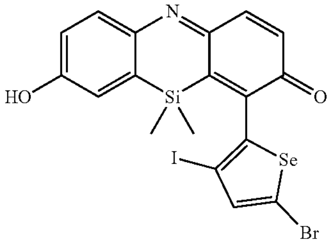
Compound 170
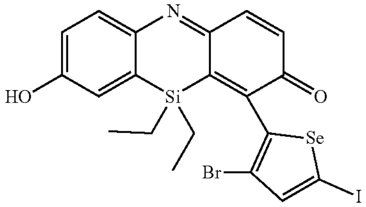
Compound 171
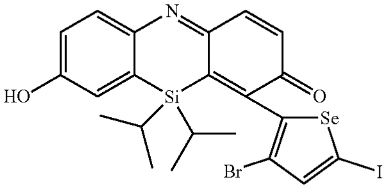
Compound 172
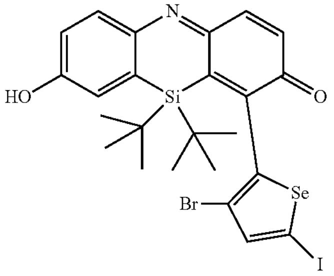
Compound 173
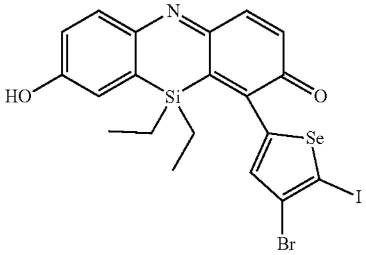
Compound 174
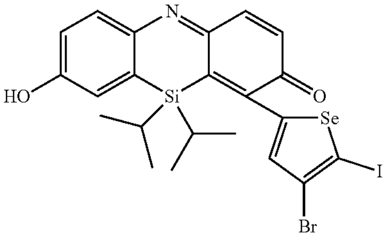
Compound 175
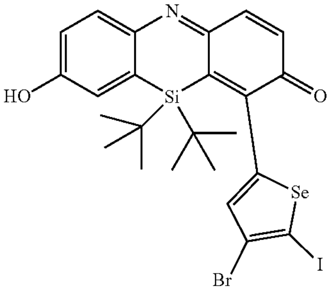
Compound 176
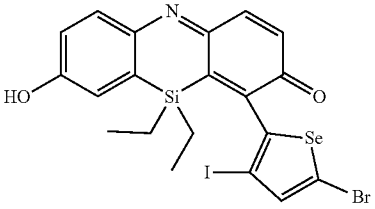
Compound 177
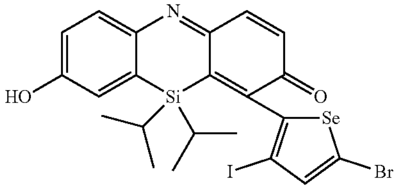
Compound 178
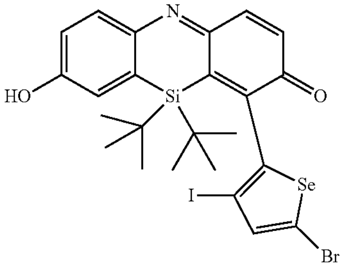
Compound 179
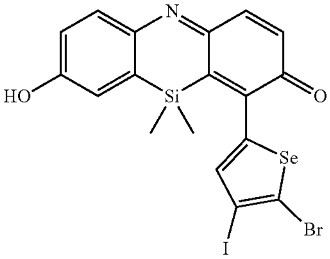
Compound 180
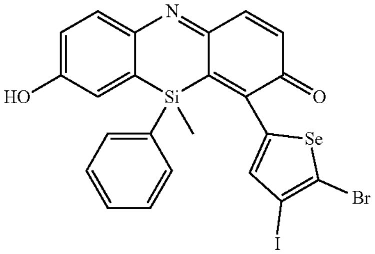

-continued
Compound 181
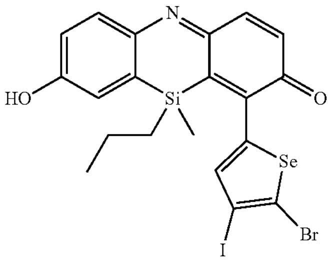
Compound 182
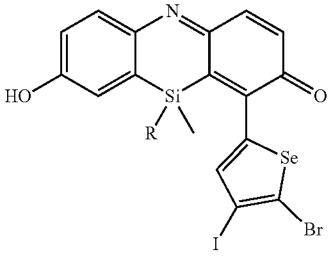
$R = —CH_2(CH_2)_{16}CH_3$
Compound 183
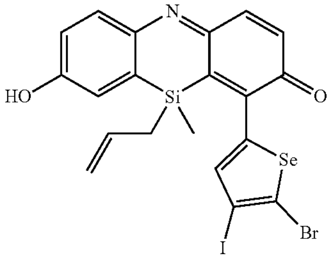
Compound 184
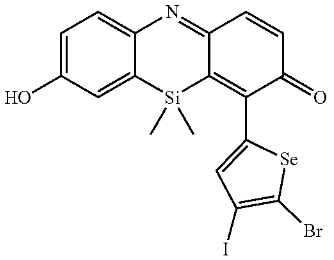
Compound 185
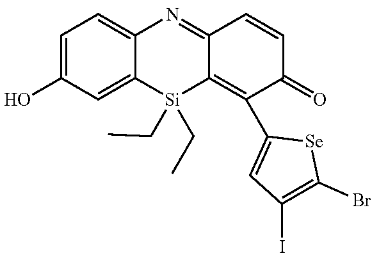
Compound 186
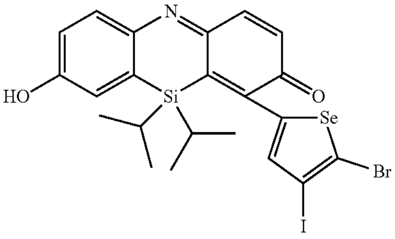
-continued
Compound 187
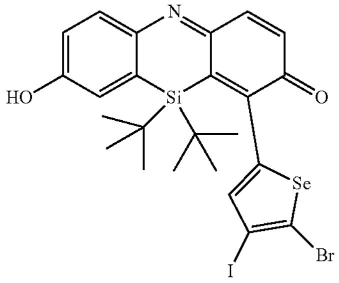
Compound 188
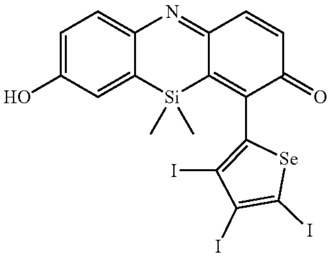
Compound 189
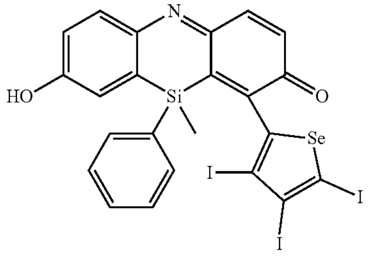
Compound 190
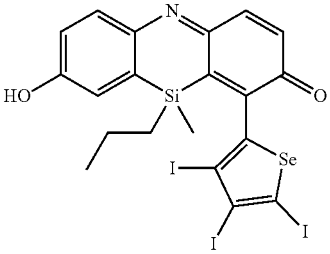
Compound 191
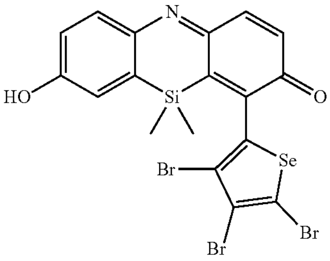
Compound 192
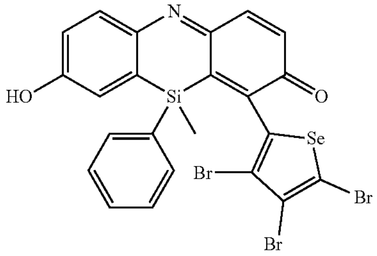

-continued
Compound 193
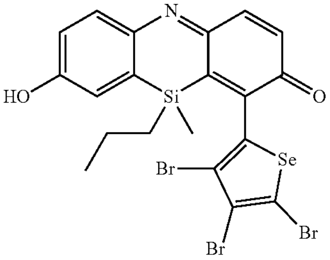
Compound 194
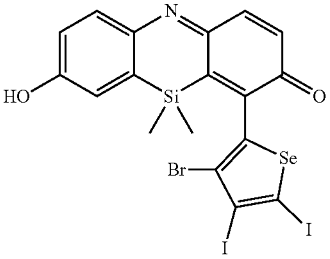
Compound 195
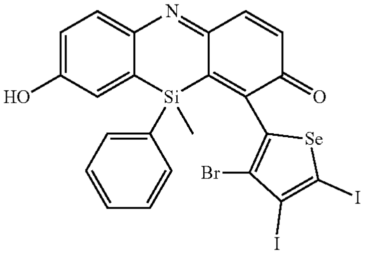
Compound 196
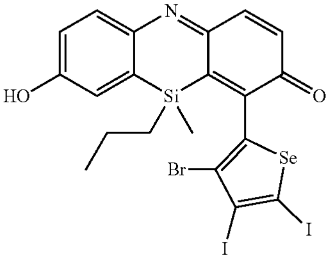
Compound 197
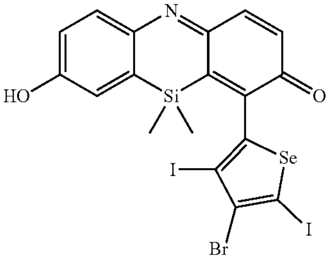
Compound 198
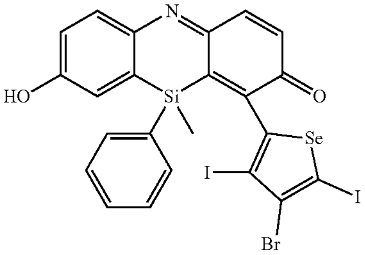
-continued
Compound 199
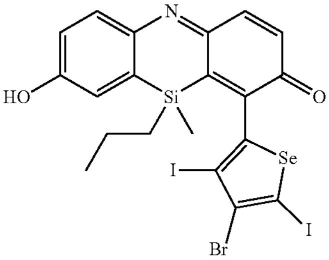
Compound 200
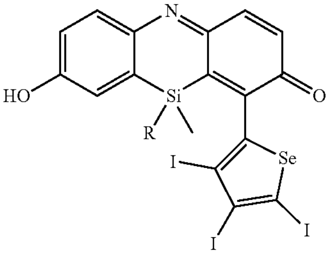
R = —$CH_2(CH_2)_{16}CH_3$
Compound 201
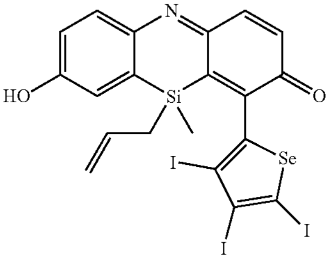
Compound 202
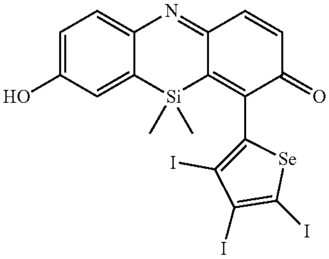
Compound 203
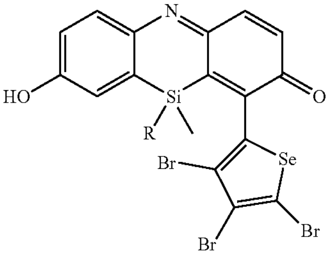
R = —$CH_2(CH_2)_{16}CH_3$ -continued
Compound 204
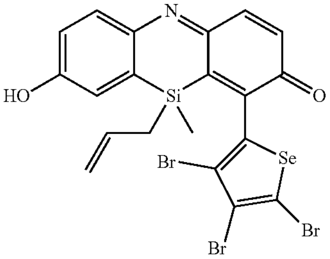
Compound 205
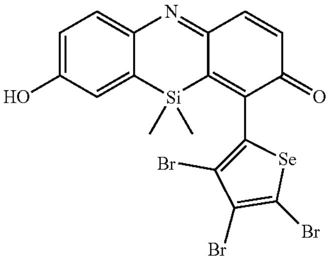
Compound 206
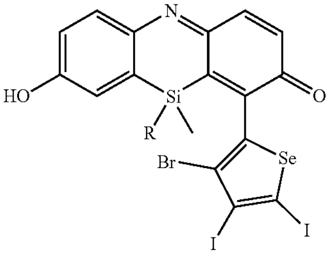
R = $-CH_2(CH_2)_{16}CH_3$
Compound 207
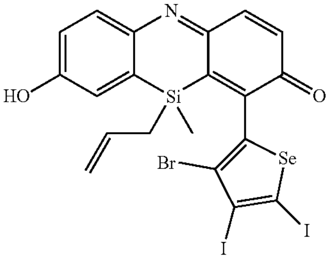
Compound 208
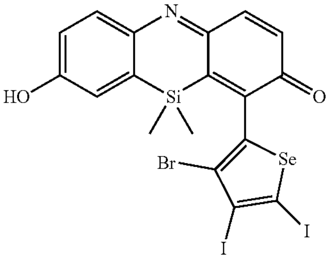
-continued
Compound 209
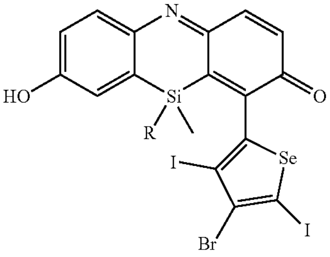
R = $-CH_2(CH_2)_{16}CH_3$
Compound 210
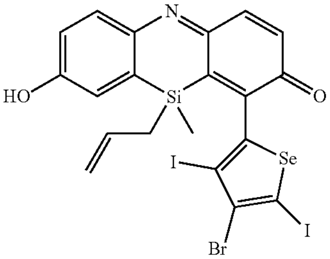
Compound 212
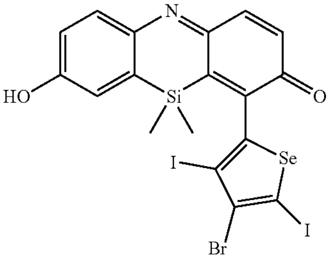
Compound 213
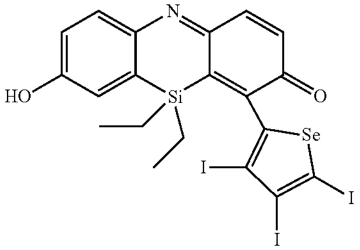
Compound 214
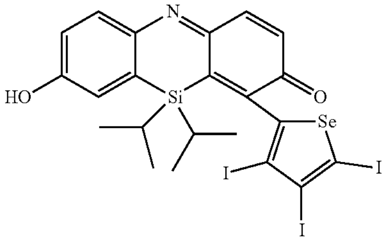
Compound 215
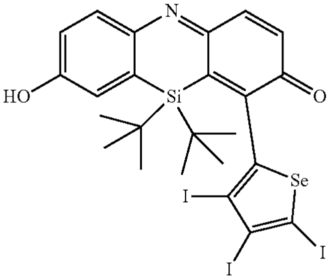

-continued
Compound 216
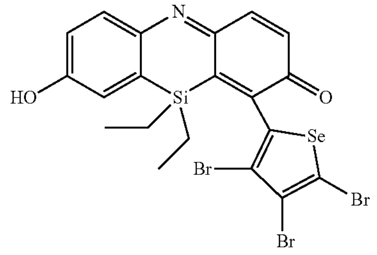
Compound 217
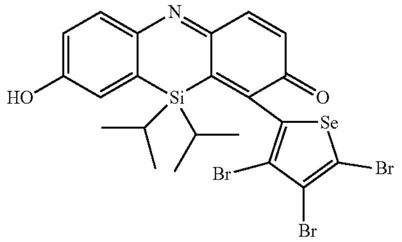
Compound 218
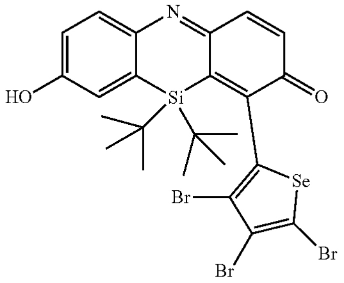
Compound 219
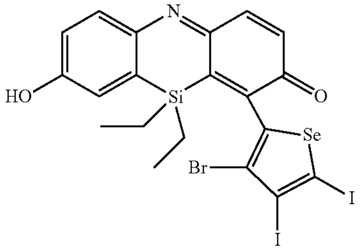
Compound 220
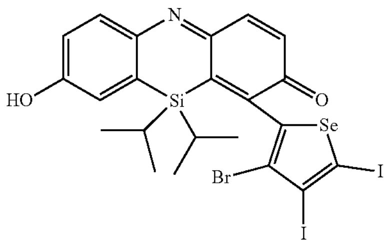
Compound 221
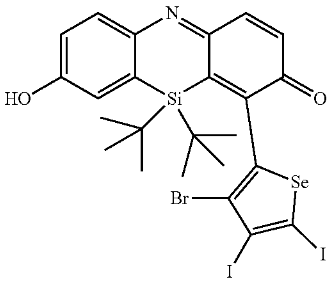
-continued
Compound 222
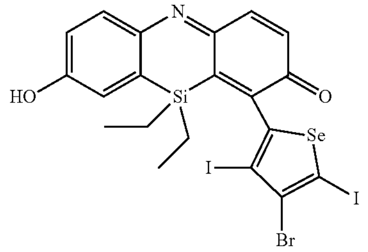
Compound 223
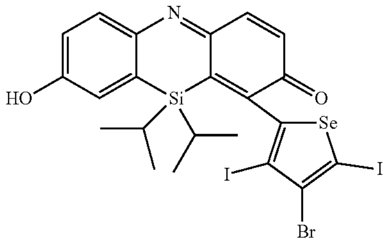
Compound 224
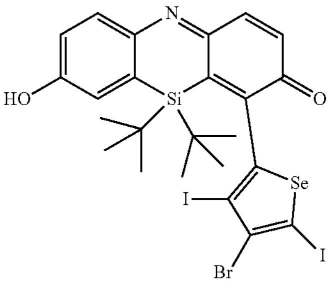
Compound 225
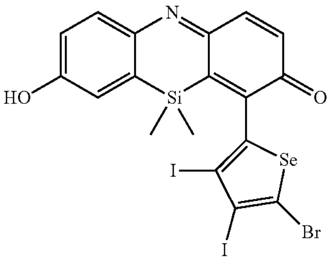
Compound 226
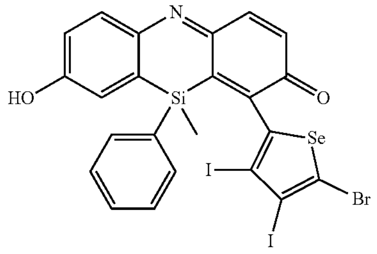
Compound 227
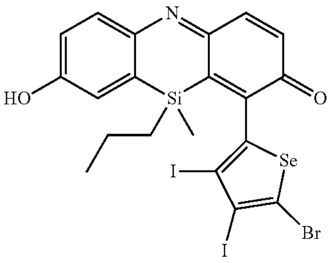

-continued
Compound 228
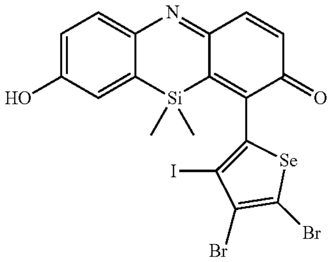
Compound 229
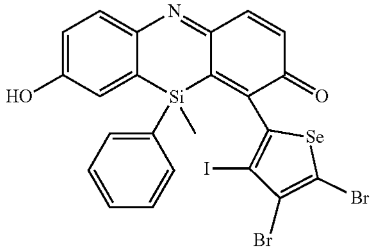
Compound 230
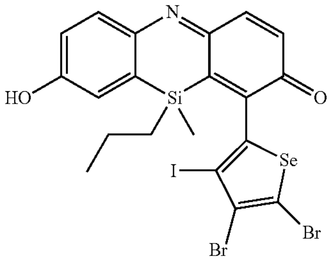
Compound 231
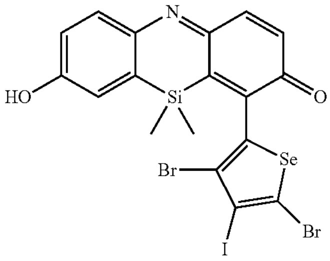
Compound 232
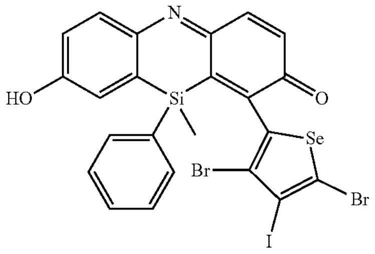
Compound 233
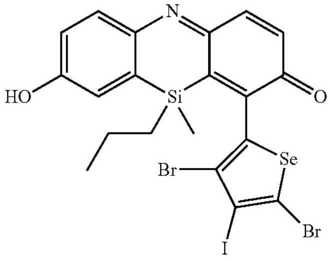
-continued
Compound 234
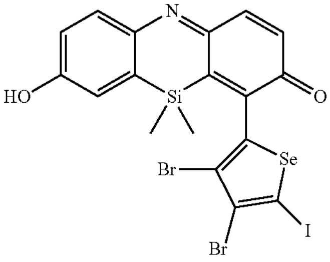
Compound 235
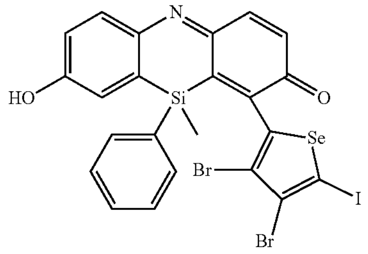
Compound 236
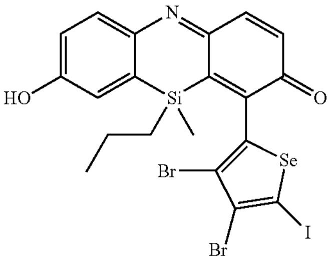
Compound 237
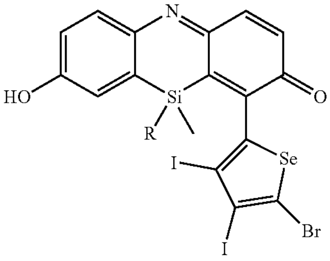
R = $—CH_2(CH_2)_{16}CH_3$
Compound 238
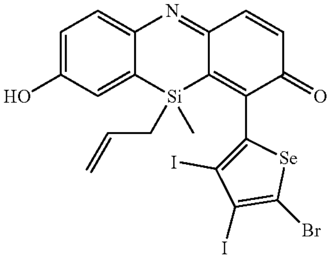
Compound 239
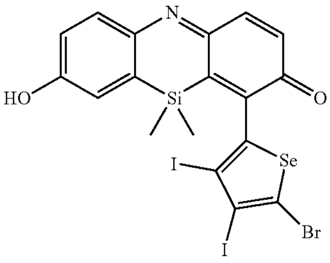

-continued
Compound 240
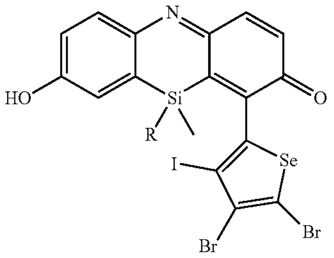
R = $-CH_2(CH_2)_{16}CH_3$
Compound 241
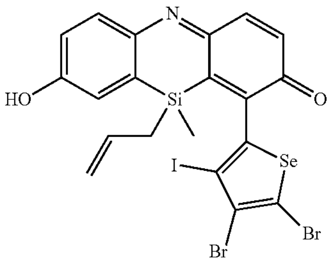
Compound 242
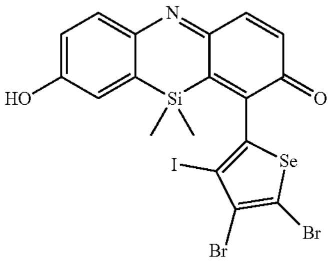
Compound 243
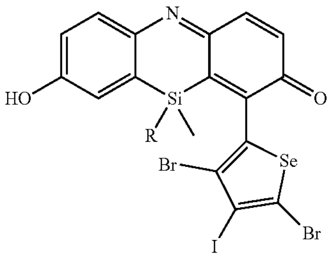
R = $-CH_2(CH_2)_{16}CH_3$
Compound 244
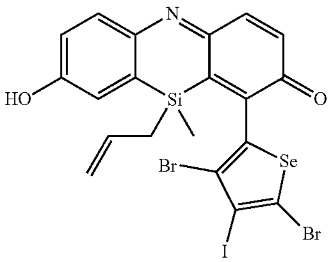
-continued
Compound 245
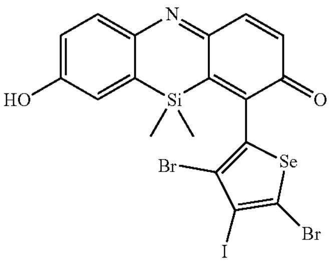
Compound 246
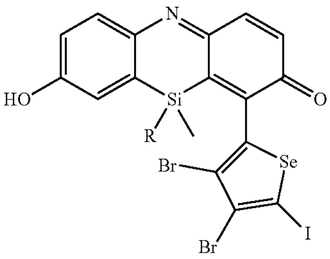
R = $-CH_2(CH_2)_{16}CH_3$
Compound 247
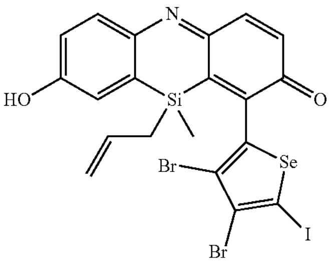
Compound 248
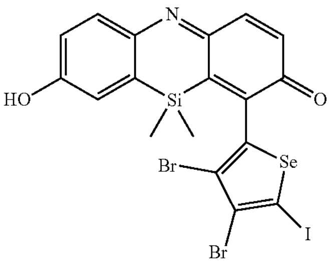
Compound 249
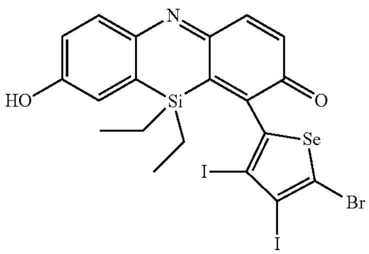
Compound 250
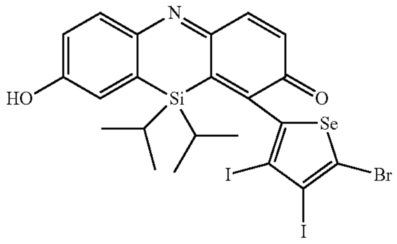

-continued
Compound 251
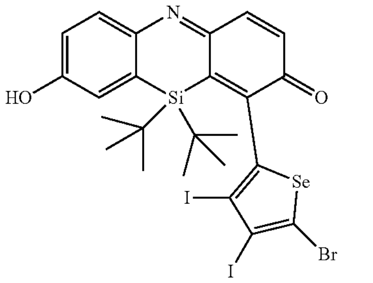
Compound 252
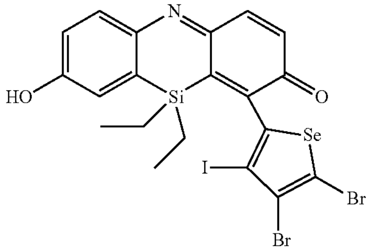
Compound 253
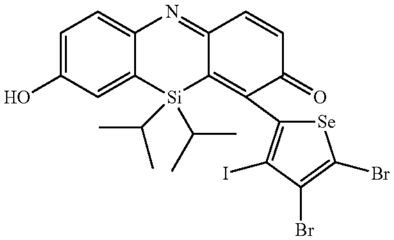
Compound 254
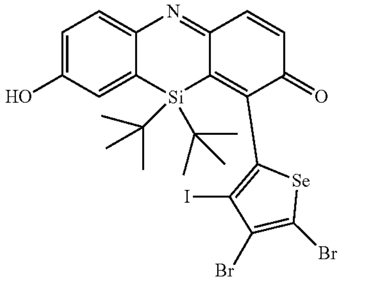
Compound 255
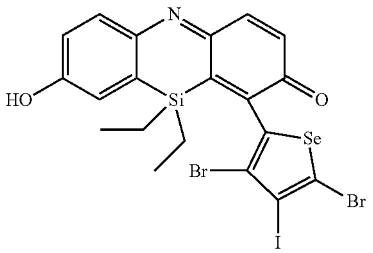
Compound 256
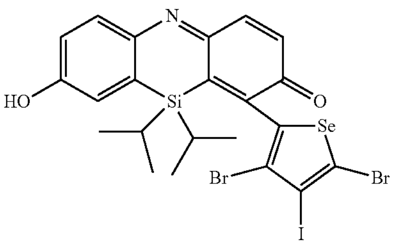
-continued
Compound 257
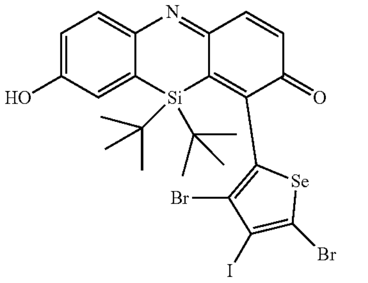
Compound 258
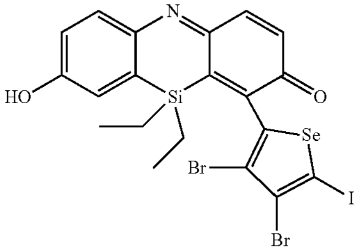
Compound 259
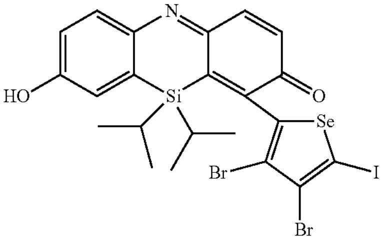
Compound 260
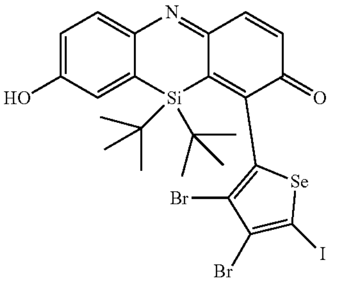
Compound 261
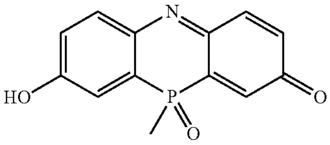
Compound 262
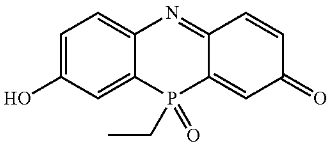
Compound 263
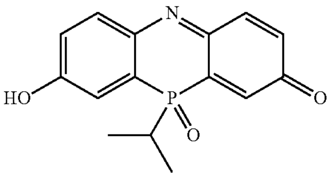

-continued
Compound 264
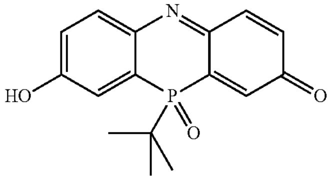
Compound 265
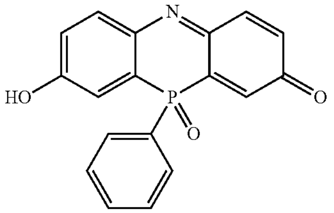
Compound 266
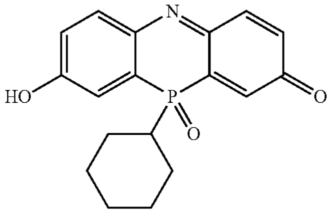
Compound 461
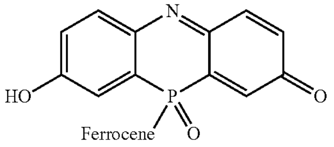
Synthesized Compounds for Use in Imaging of Cancer Cells:
Compound 267
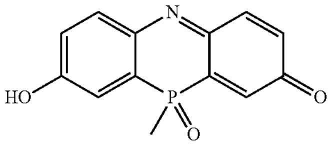
Compound 268
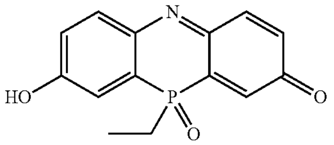
Compound 269
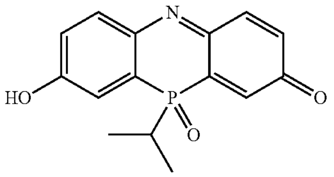
Compound 270
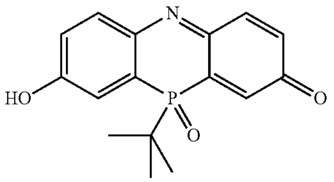
-continued
Compound 271
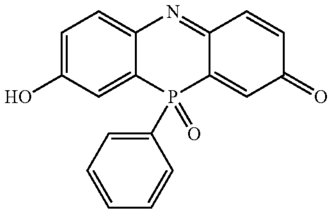
Compound 272
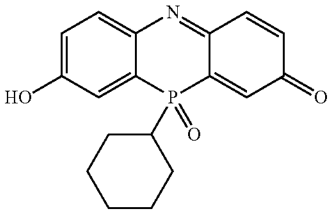
Compound 273
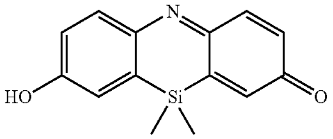
Compound 274
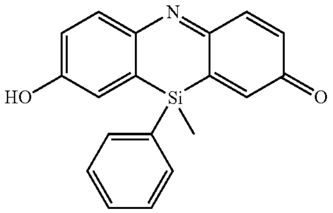
Compound 275
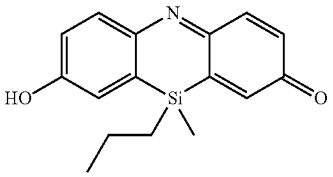
Compound 276
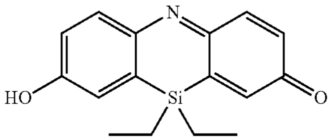
Compound 277
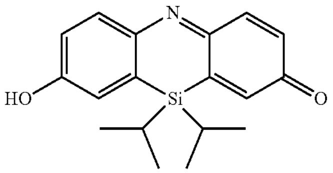
Compound 278
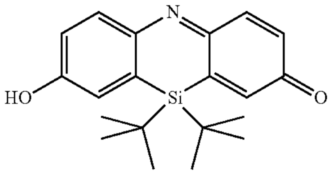

-continued
Compound 279
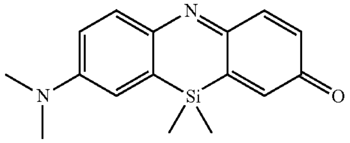
Compound 280
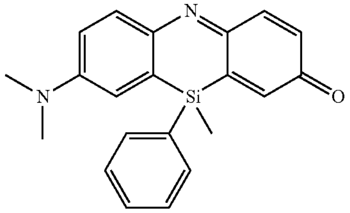
Compound 281
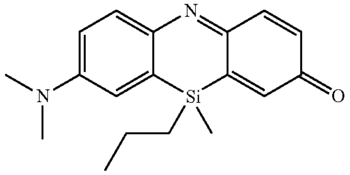
Compound 282
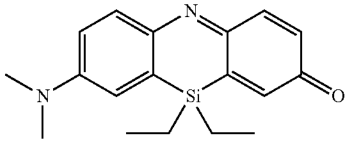
Compound 283
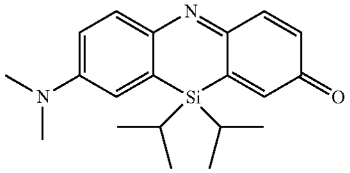
Compound 284
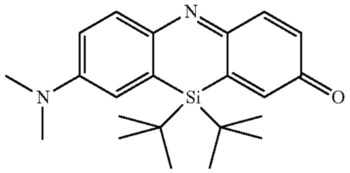
Compound 285
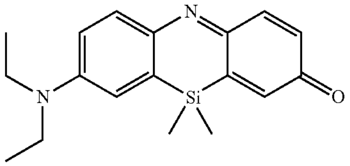
Compound 286
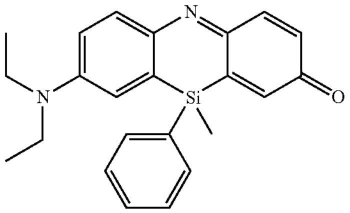
-continued
Compound 287
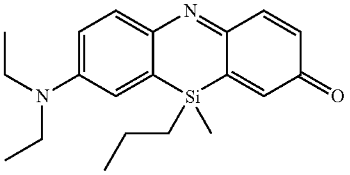
Compound 288
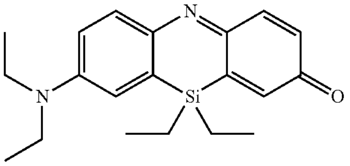
Compound 289
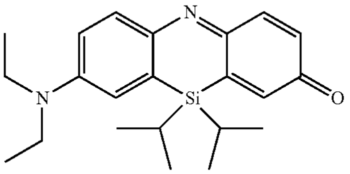
Compound 290
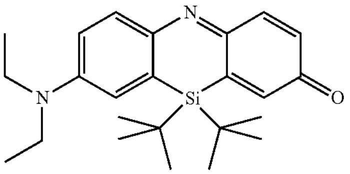
Compound 291
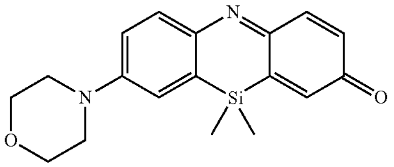
Compound 292
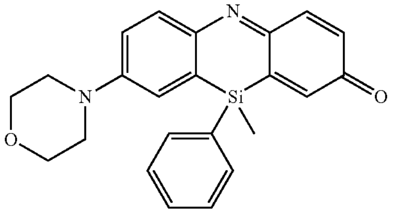
Compound 293
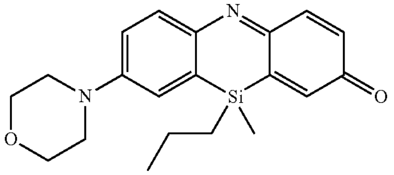
Compound 294
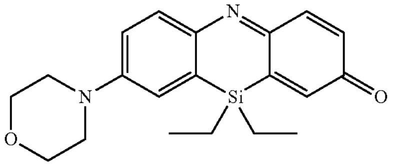

-continued
Compound 295
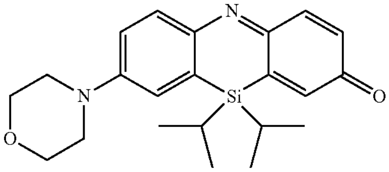
Compound 296
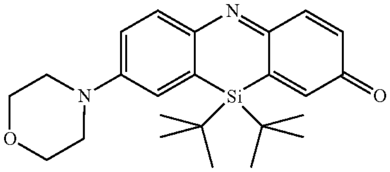
Compound 297
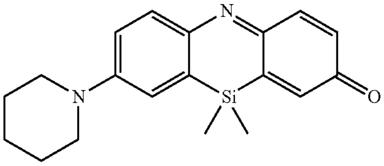
Compound 298
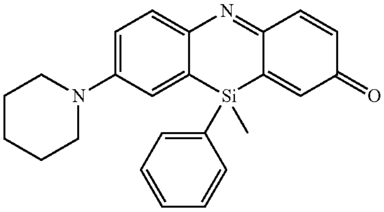
Compound 299
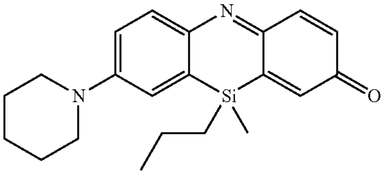
Compound 300
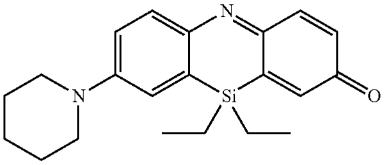
Compound 301
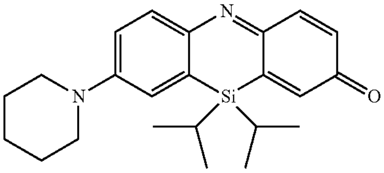
Compound 302
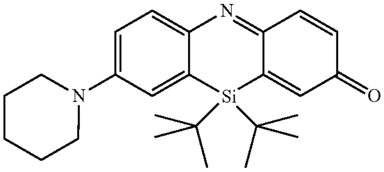
-continued
Compound 303
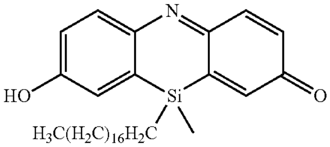
Compound 304
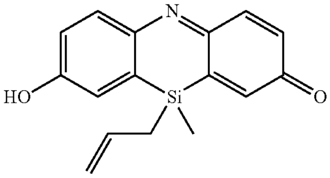
Compound 305
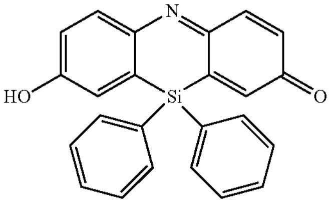
Compound 306
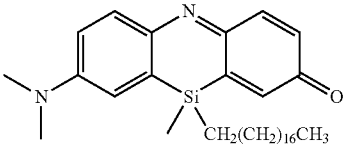
Compound 307
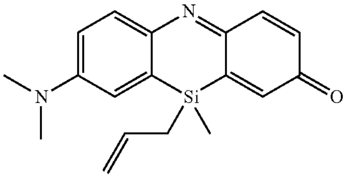
Compound 308
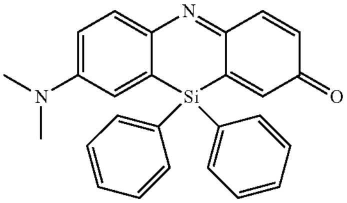
Compound 309
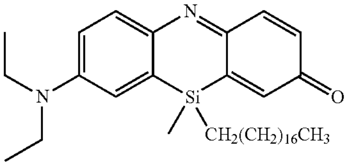
Compound 310
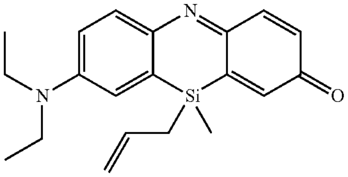

-continued
Compound 311
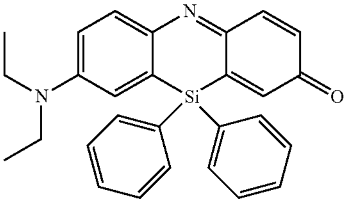
Compound 312
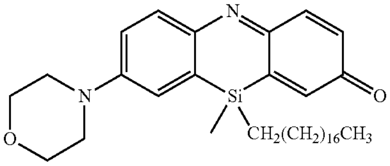
Compound 313
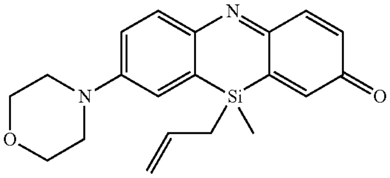
Compound 314
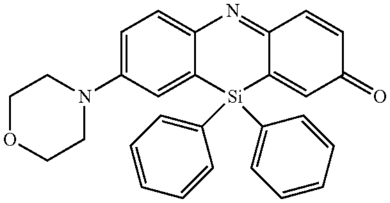
Compound 315
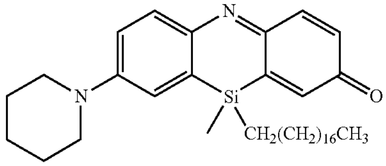
Compound 316
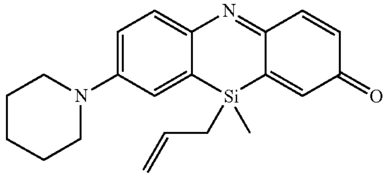
Compound 317
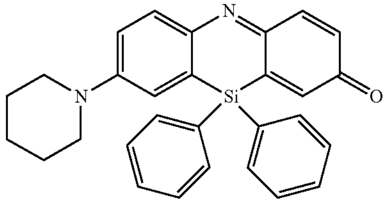
Compound 318
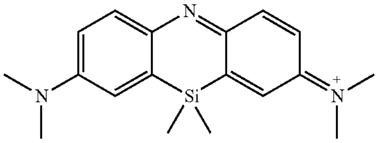
-continued
Compound 319
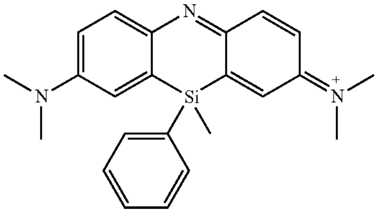
Compound 320
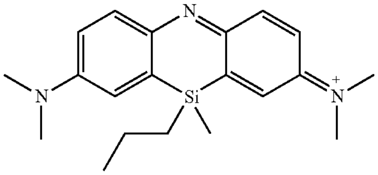
Compound 321
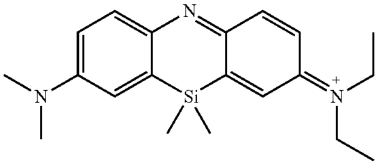
Compound 322
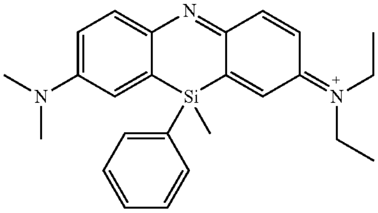
Compound 323
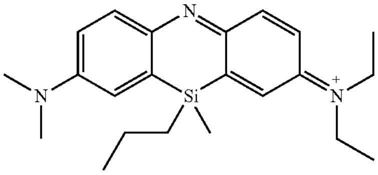
Compound 324
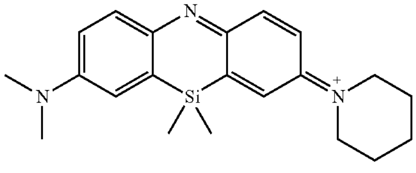
Compound 325
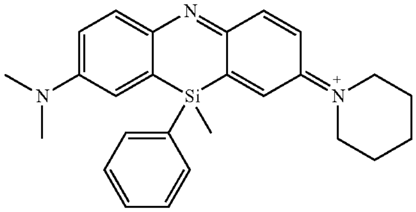

-continued
Compound 326
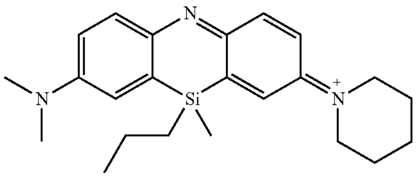
Compound 327
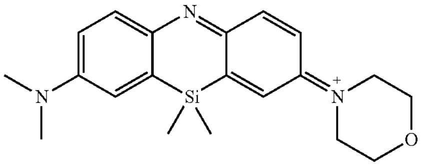
Compound 328
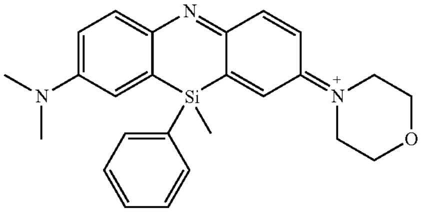
Compound 329
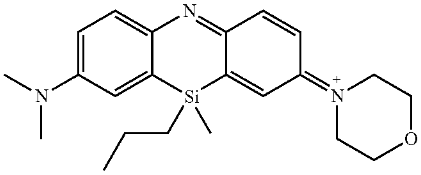
Compound 330
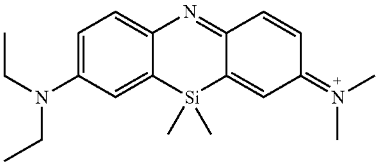
Compound 331
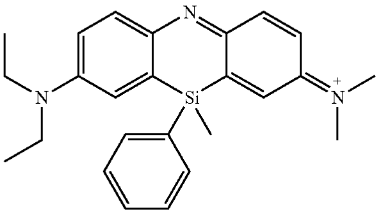
Compound 332
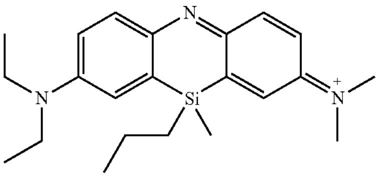
Compound 333
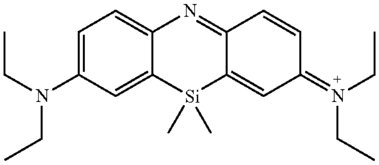
-continued
Compound 334
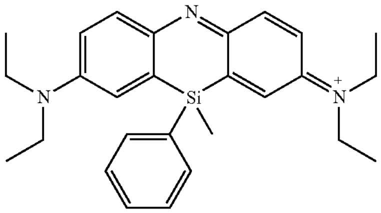
Compound 335
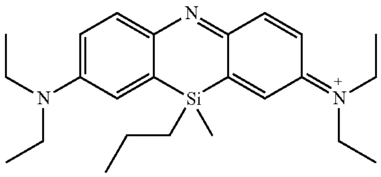
Compound 336
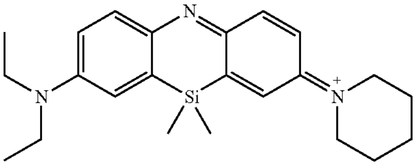
Compound 337
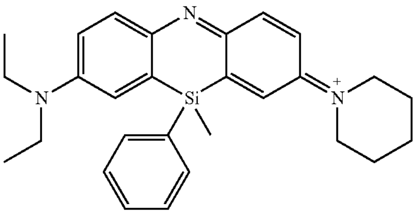
Comppound 338
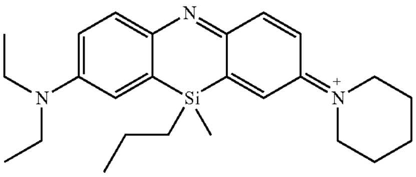
Compound 339
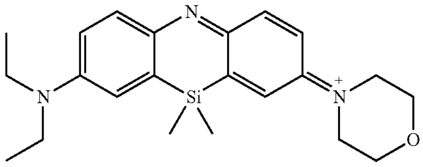
Compound 340
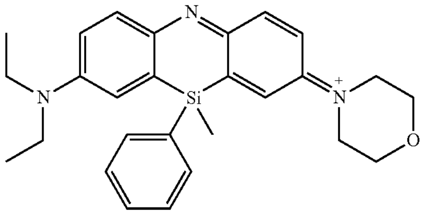

-continued
Compound 341
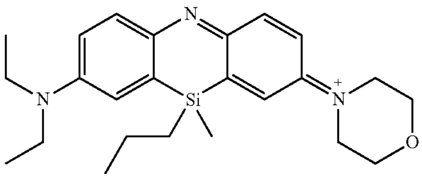
Compound 342
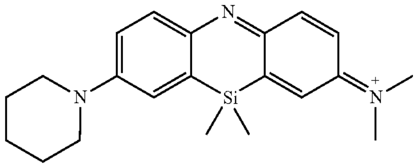
Compound 343
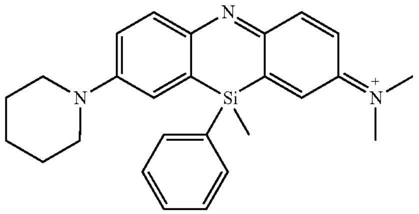
Compound 344
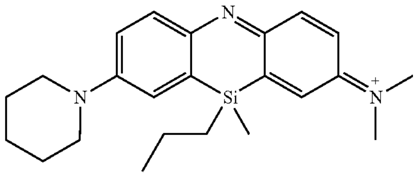
Compound 345
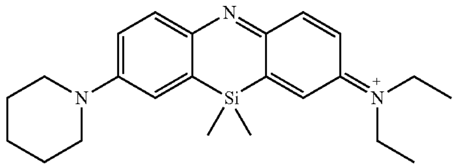
Compound 346
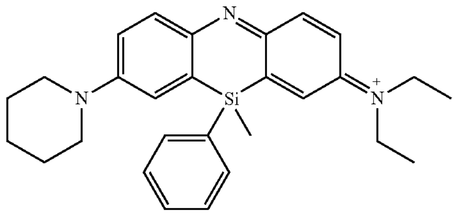
Compound 347
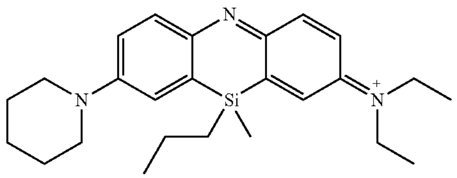
Compound 348
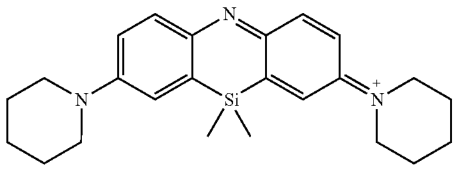
-continued
Compound 349
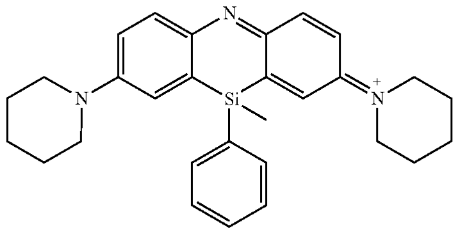
Compound 350
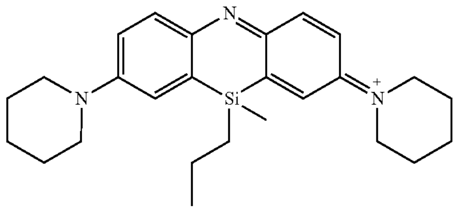
Compound 351
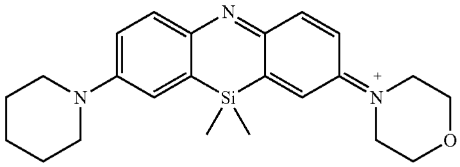
Compound 352
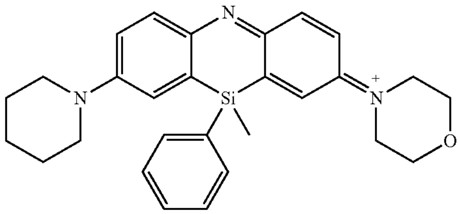
Compound 353
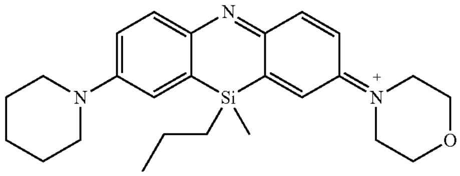
Compound 354
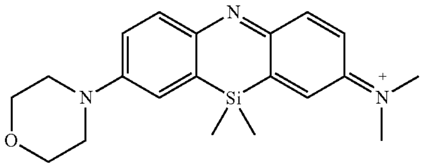
Compound 355
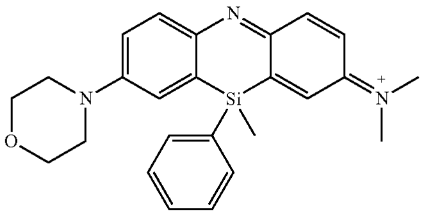

-continued
Compound 356
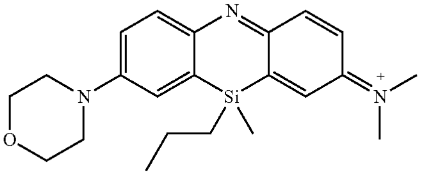
Compound 357
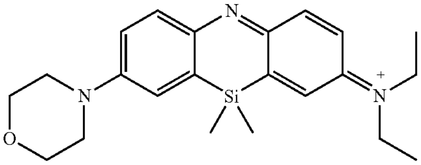
Compound 358
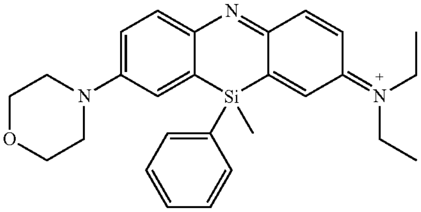
Compound 359
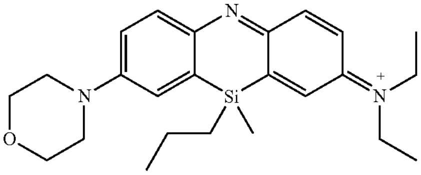
Compound 360
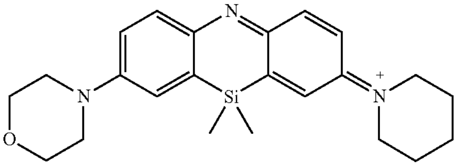
Compound 361
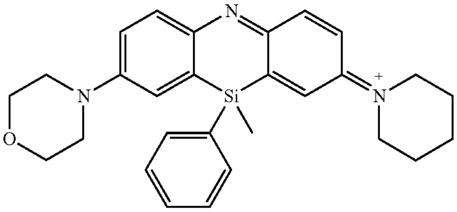
Compound 361
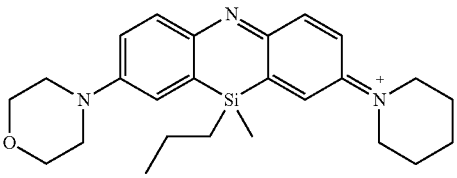
Compound 362
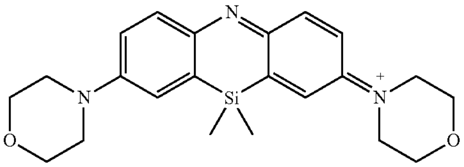
-continued
Compound 363
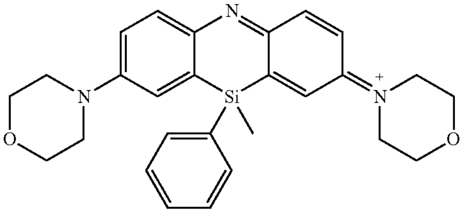
Compound 364
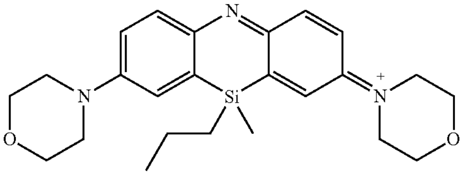
Compound 365
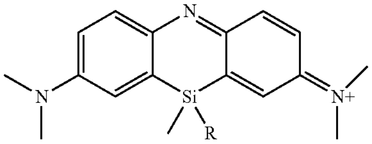
R = $-CH_2(CH_2)_{16}CH_3$
Compound 366
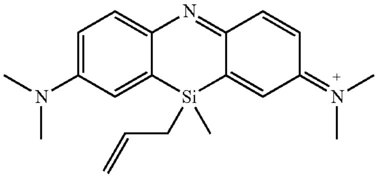
Compound 367
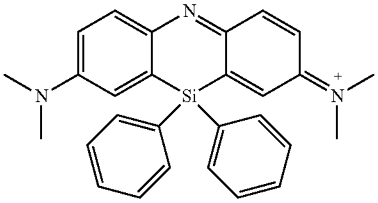
Compound 368
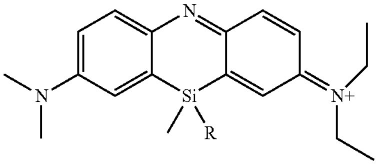
R = $-CH_2(CH_2)_{16}CH_3$
Compound 369
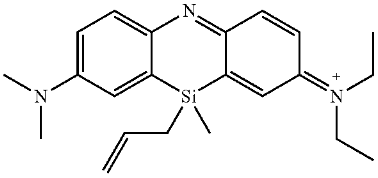

-continued
Compound 370
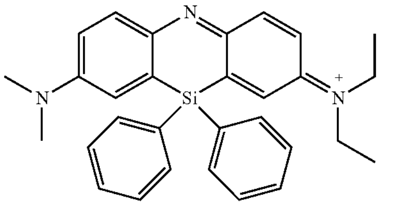
Compound 371
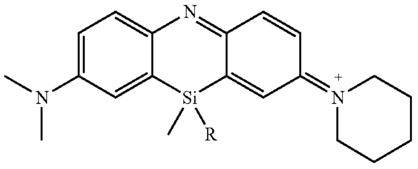
R = —$CH_2(CH_2)_{16}CH_3$
Compound 372
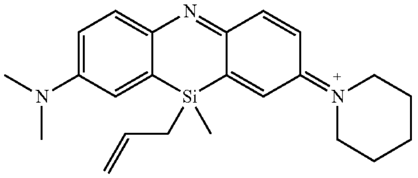
Compound 373
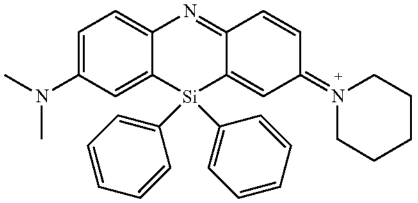
Compound 374
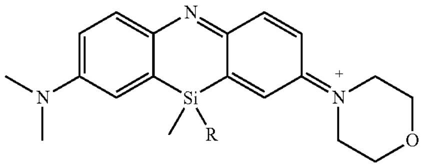
R = —$CH_2(CH_2)_{16}CH_3$
Compound 375
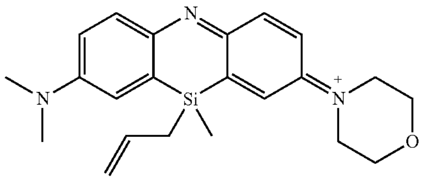
Compound 376
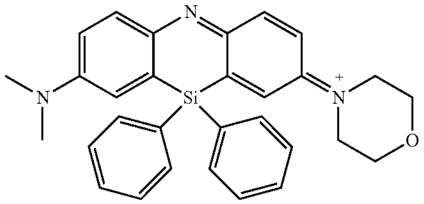
Compound 377
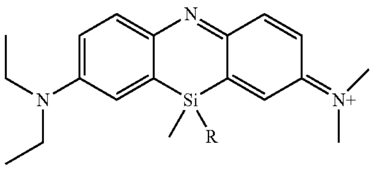
R = —$CH_2(CH_2)_{16}CH_3$
-continued
Compound 378
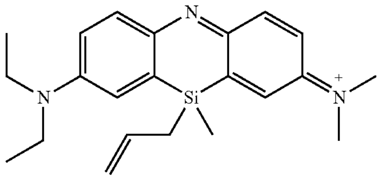
Compound 379
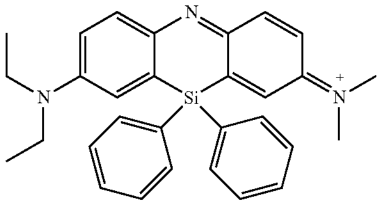
Compound 380
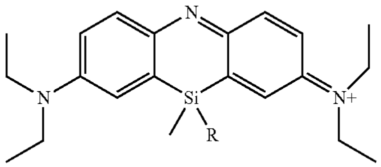
R = —$CH_2(CH_2)_{16}CH_3$
Compound 381
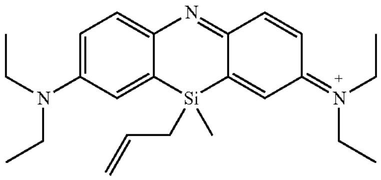
Compound 382
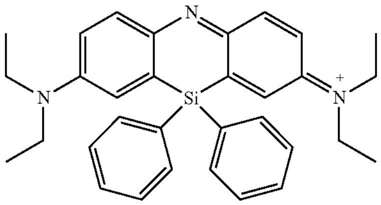
Compound 383
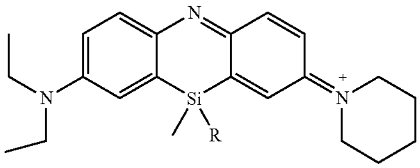
R = —$CH_2(CH_2)_{16}CH_3$
Compound 384
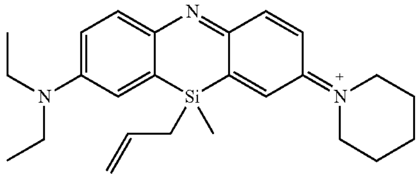
Compound 385
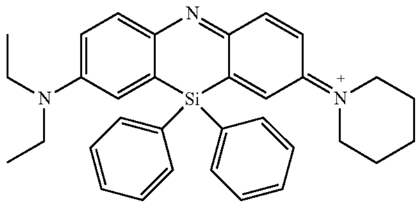

-continued
Compound 386
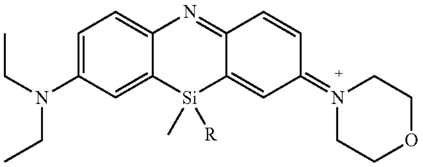
$R = -CH_2(CH_2)_{16}CH_3$
Compound 387
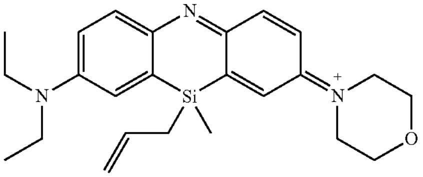
Compound 388
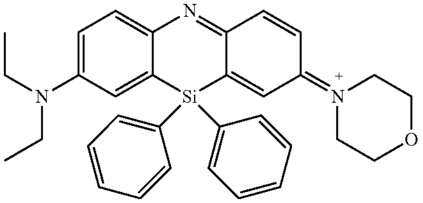
Compound 389
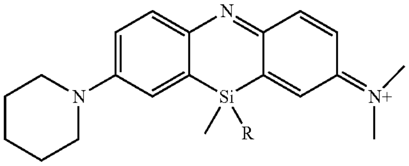
$R = -CH_2(CH_2)_{16}CH_3$
Compound 390
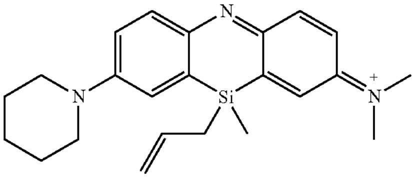
Compound 391
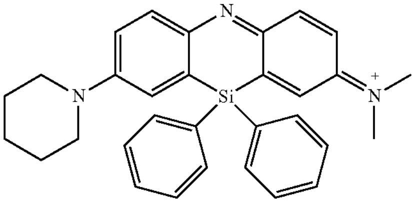
Compound 392
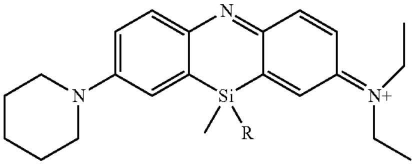
$R = -CH_2(CH_2)_{16}CH_3$
Compound 393
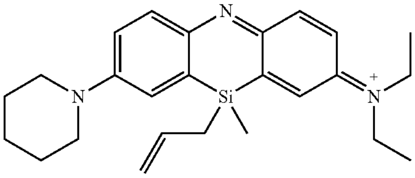
-continued
Compound 394
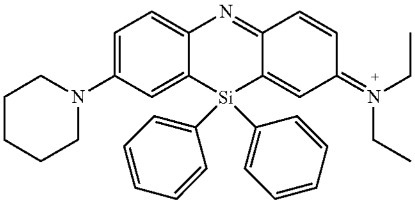
Compound 395
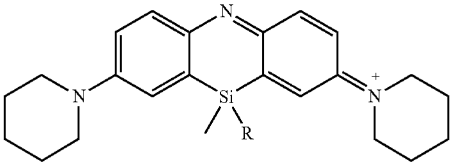
$R = -CH_2(CH_2)_{16}CH_3$
Compound 396
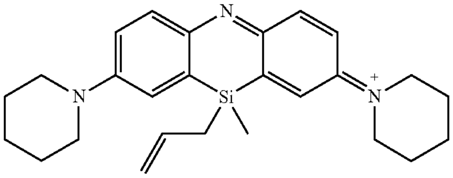
Compound 397
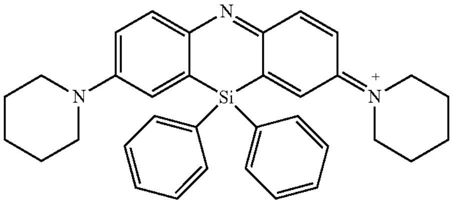
Compound 398
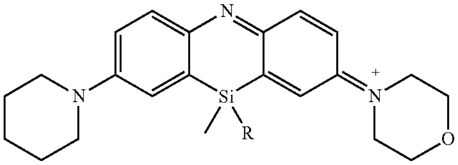
$R = -CH_2(CH_2)_{16}CH_3$
Compound 399
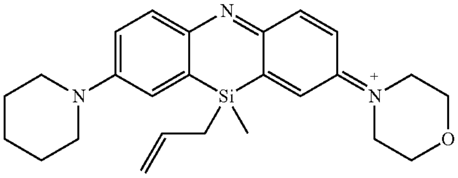
Compound 400
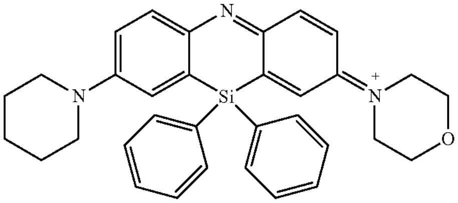

-continued
Compound 401
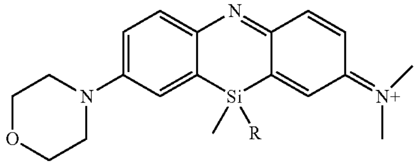
R = —$CH_2(CH_2)_{16}CH_3$
Compound 402
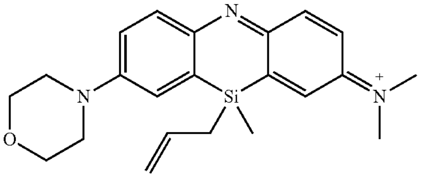
Compound 403
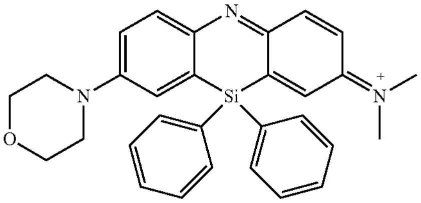
Compound 404
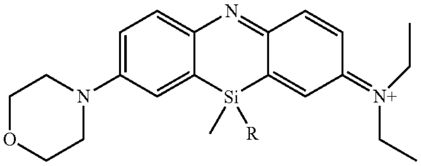
R = —$CH_2(CH_2)_{16}CH_3$
Compound 405
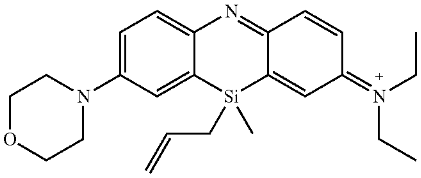
Compound 406
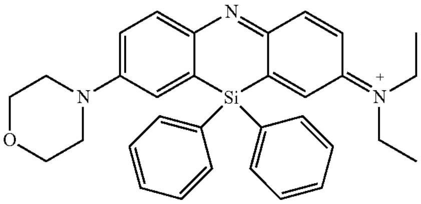
Compound 407
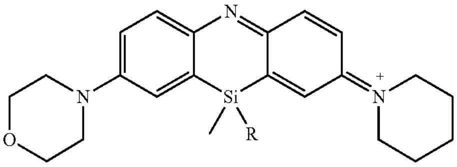
R = —$CH_2(CH_2)_{16}CH_3$
-continued
Compound 408
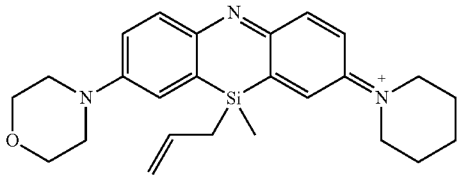
Compound 409
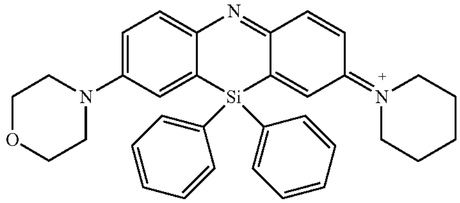
Compound 410
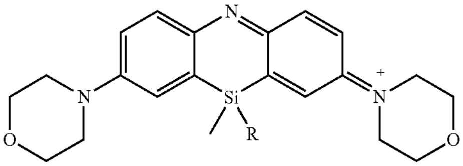
R = —$CH_2(CH_2)_{16}CH_3$
Compound 411
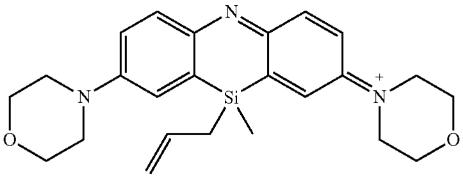
Compound 412
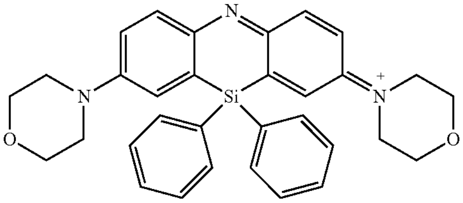
Compound 412
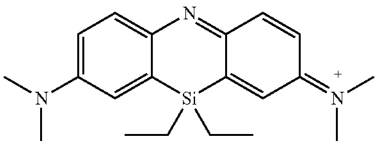
Compound 413
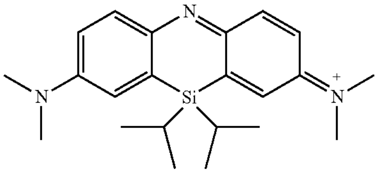
Compound 414
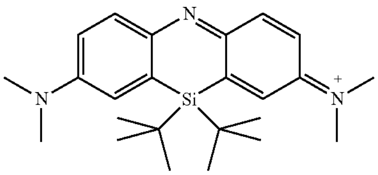

-continued
Compound 415
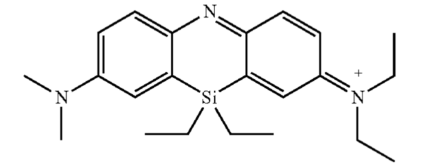
Compound 416
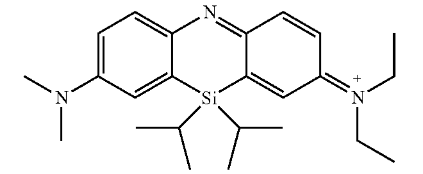
Compound 417
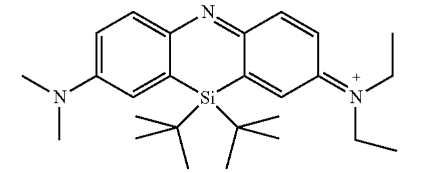
Compound 418
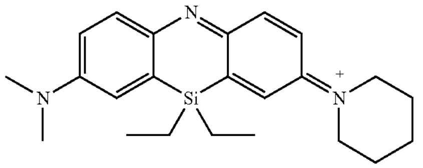
Compound 419
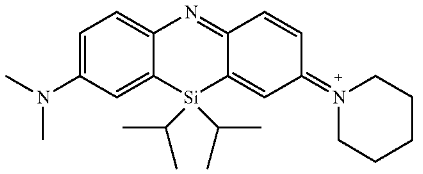
Compound 420
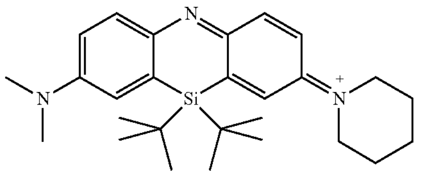
Compound 421
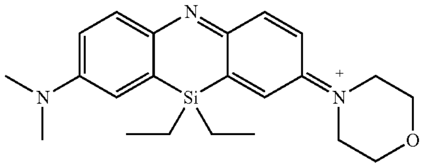
Compound 422
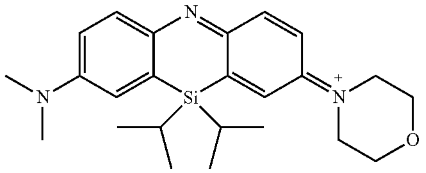
Compound 423
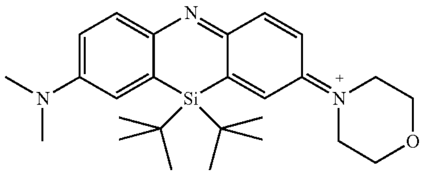
-continued
Compound 424
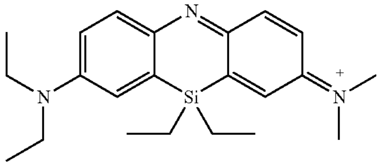
Compound 425
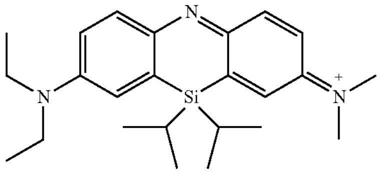
Compound 426
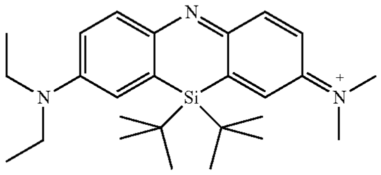
Compound 427
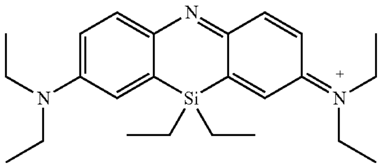
Compound 428
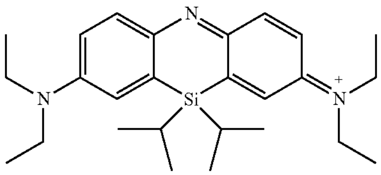
Compound 429
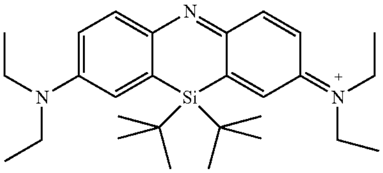
Compound 430
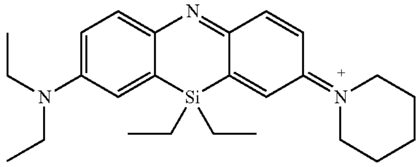
Compound 431
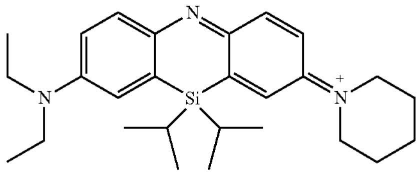
Compound 432
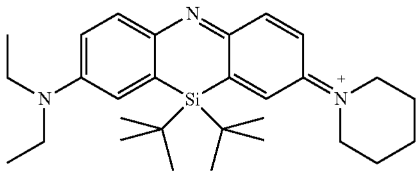

-continued
Compound 433
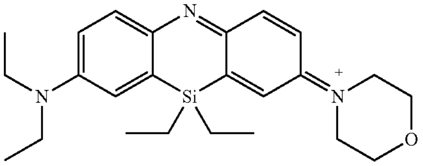
Compound 434
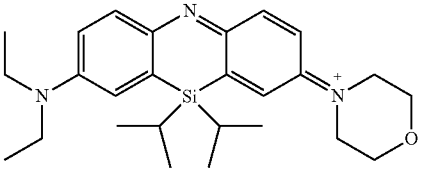
Compound 435
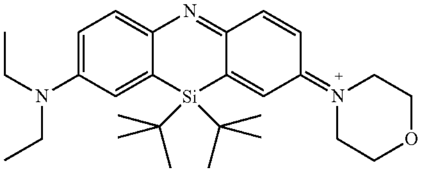
Compound 436
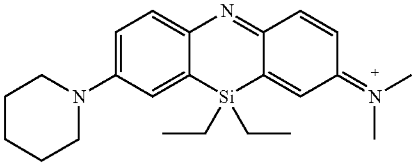
Compound 437
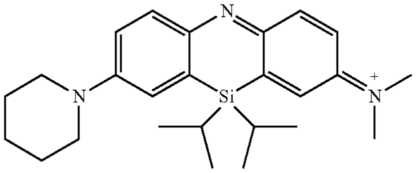
Compound 438
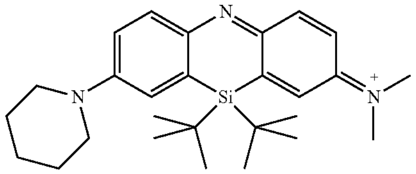
Compound 439
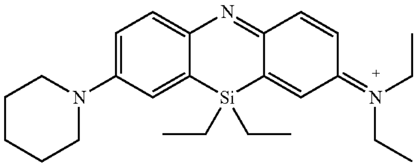
Compound 440
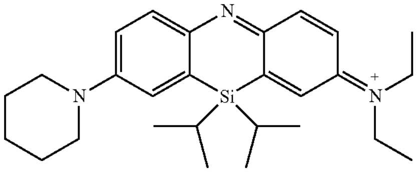
Compound 441
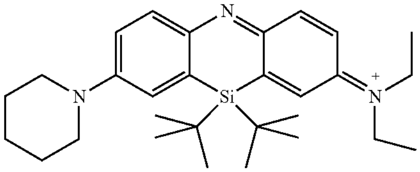
-continued
Compound 442
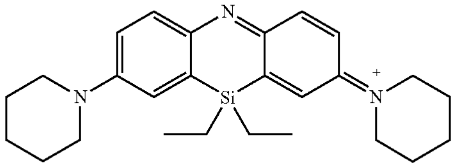
Compound 443
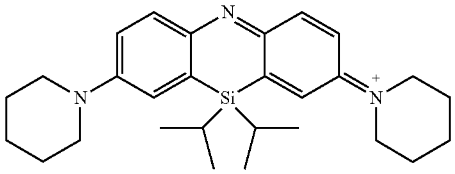
Compound 444
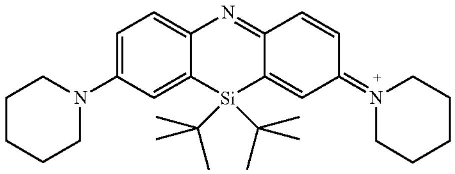
Compound 445
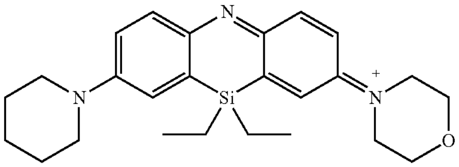
Compound 446
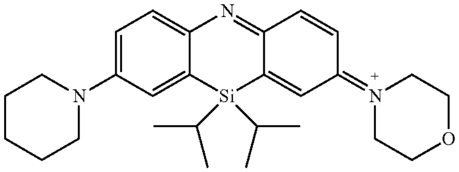
Compound 447
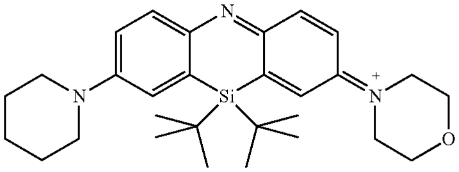
Compound 448
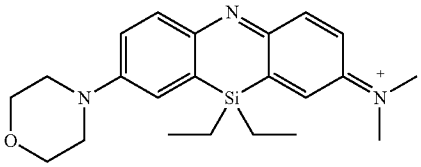
Compound 449
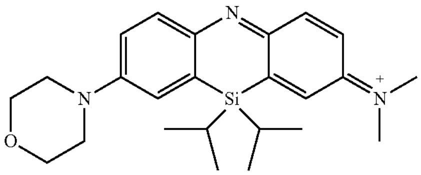

-continued
Compound 450
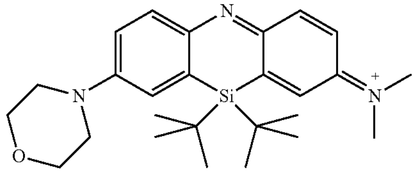
Compound 451
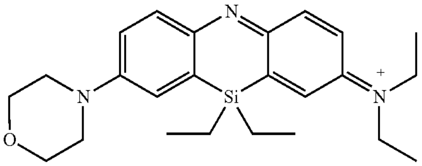
Compound 452
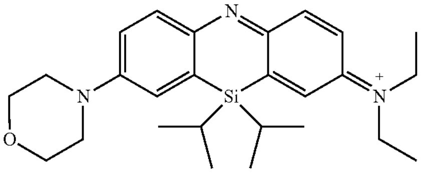
Compound 453
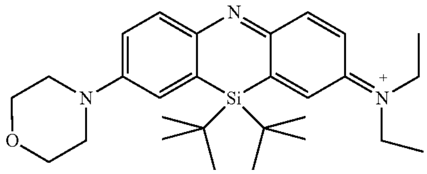
Compound 454
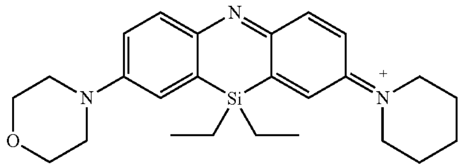
Compound 455
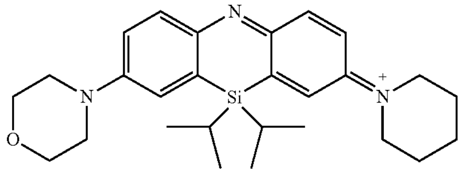
Compound 456
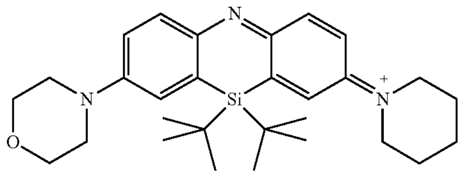
Compound 457
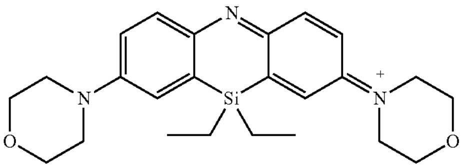
-continued
Compound 458
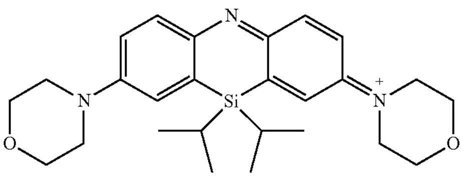
Compound 459
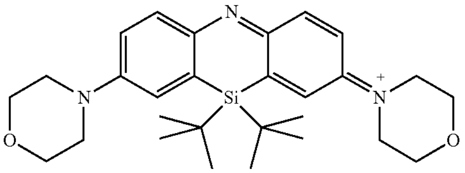
Compound 460
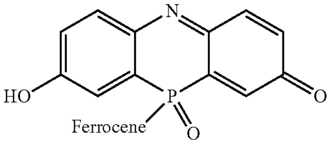
What is claimed is:
1. A NIR absorbing photosensitizer, comprising formula C or D or E or F or G,
formula C
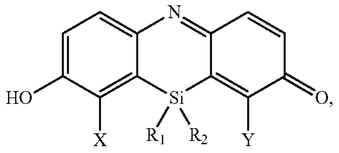
wherein;
R1 = $-CH_3$, $-CH_2CH_3$, $-CH_2CH_2CH_3$, $-CH_2(CH_2)_{16}CH_3$, 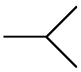, 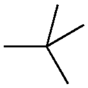, 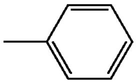;
R2 = $-CH_3$, $-CH_2CH_3$, $-CH_2CH_2CH_3$, $-CH_2(CH_2)_{16}CH_3$, 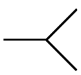, 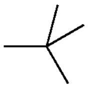, 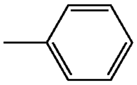;
X = $-Br$, $-I$, 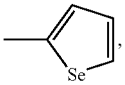, 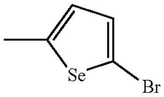, 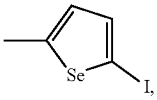 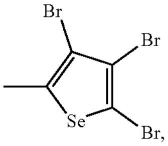 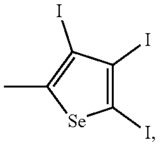 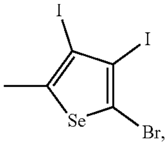 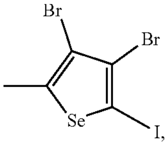 $-Se$ $R_3$, 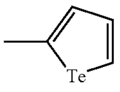, -continued

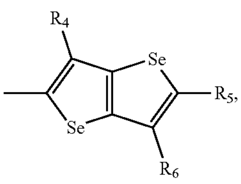, 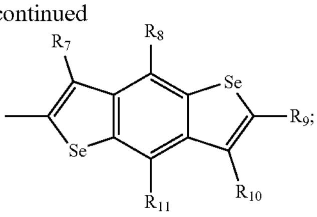;

wherein $R_3$=alkyl;

$R_4$=—H, —Br, —I, alkyl;

$R_5$=—H, —Br, —I, alkyl;

$R_6$=—H, —Br, —I, alkyl;

$R_7$=—H, —Br, —I;

$R_8$=—H, —Br, —I, alkyl;

$R_9$=—H, —Br, —I, alkyl;

$R_{10}$=—H, —Br, —I, alkyl; and $R_{11}$=—H, —Br, —I, alkyl;

Y = —Br, —I,

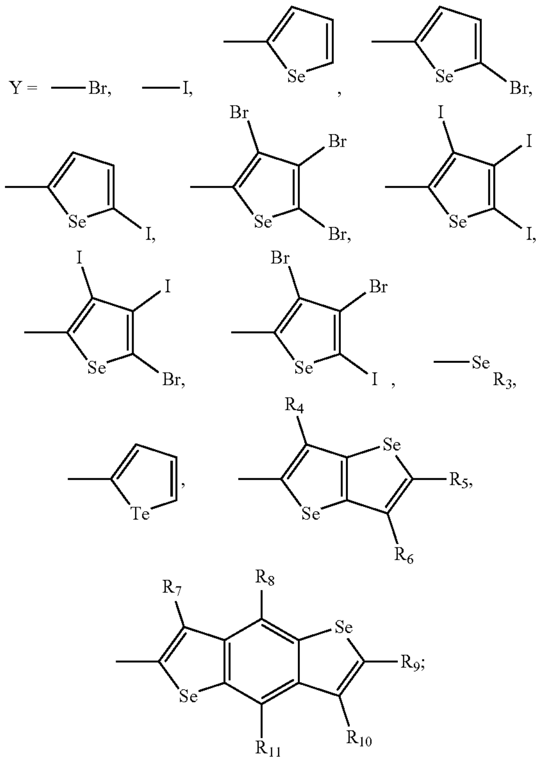

wherein $R_3$=alkyl;

$R_4$=—H, —Br, —I, alkyl;

$R_5$=—H, —Br, —I, alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl;

$R_{10}$=—H, —Br, —I, alkyl; and $R_{11}$=—H, —Br, —I, alkyl;

formula D

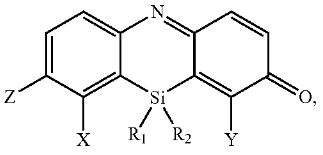

wherein;

R1 = —$CH_3$, —$CH_2CH_3$, —$CH_2CH_2CH_3$, —$CH_2(CH_2)_{16}CH_3$,

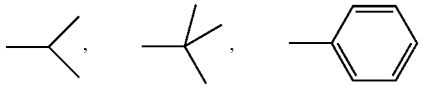

R2 = —$CH_3$, —$CH_2CH_3$, —$CH_2CH_2CH_3$, —$CH_2(CH_2)_{16}CH_3$,

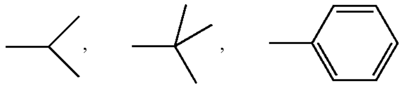

Z = 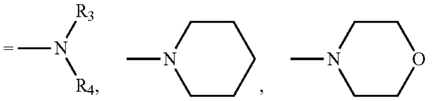

X = —Br, —I,

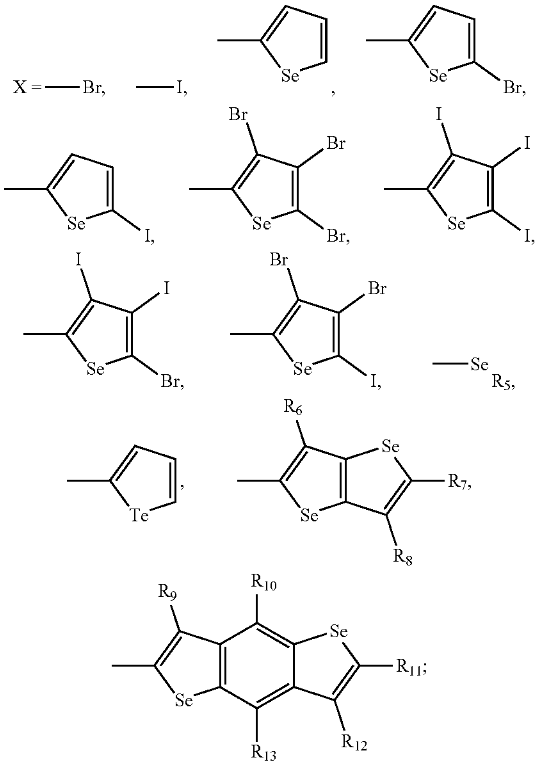

wherein $R_3$=alkyl;

$R_4$=alkyl;

$R_5$=alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl;

$R_{10}$=—H, —Br, —I, alkyl;

$R_{11}$=—H, —Br, —I, alkyl;

$R_{12}$=—H, —Br, —I, alkyl; and $R_{13}$=—H, —Br, —I, alkyl;

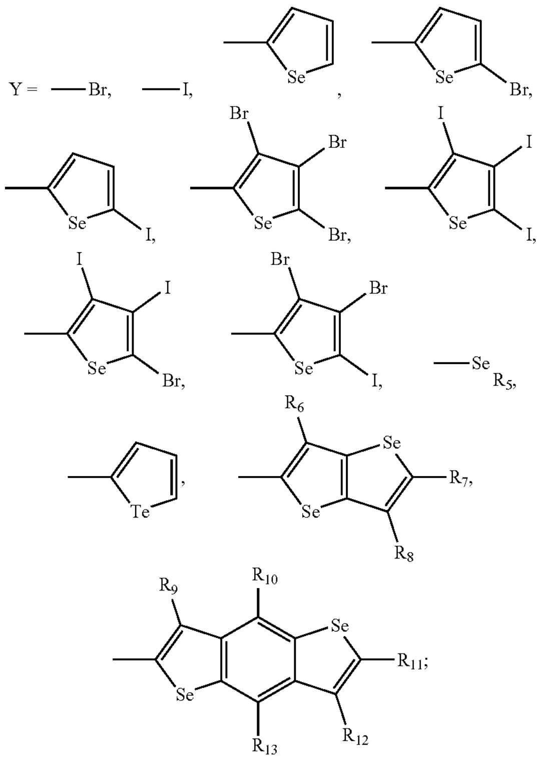

wherein $R_5$=alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl;

$R_{10}$=—H, —Br, —I, alkyl;

$R_{11}$=—H, —Br, —I, alkyl;

$R_{12}$=—H, —Br, —I, alkyl; and $R_{13}$=—H, —Br, —I, alkyl;

formula E

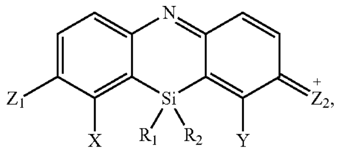

wherein;

R1 is an alkyl (R), R2 is an alkyl (R),

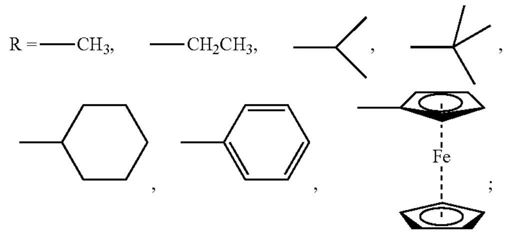

-continued

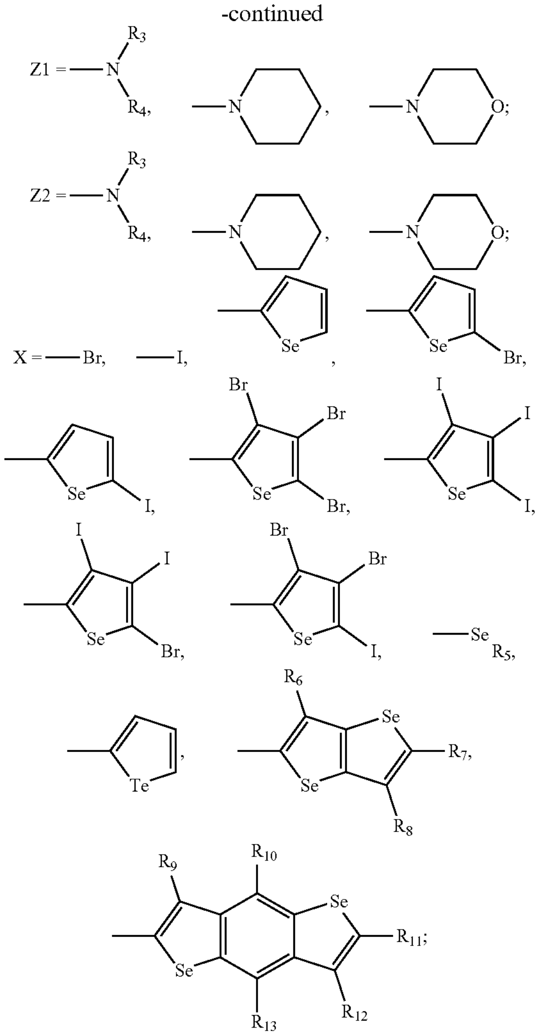

wherein $R_3$=alkyl;

$R_4$=alkyl;

$R_5$=alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl;

$R_{10}$=—H, —Br, —I, alkyl;

$R_{11}$=—H, —Br, —I, alkyl;

$R_{12}$=—H, —Br, —I, alkyl; and $R_{13}$—H, —Br, —I, alkyl;

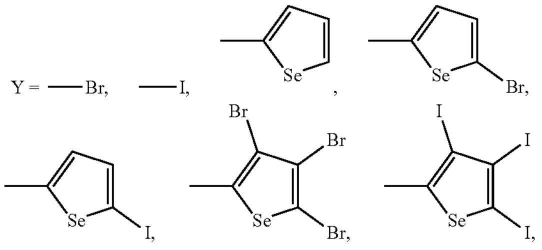

-continued

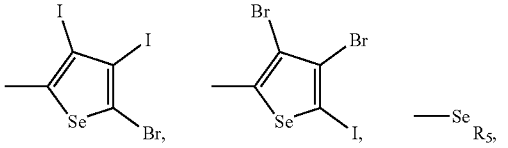
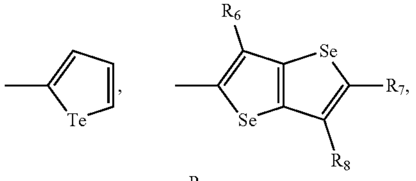
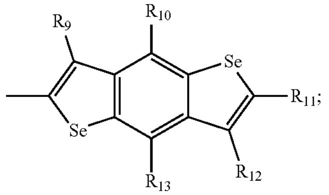

wherein $R_5$=alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl;

$R_{10}$=—H, —Br, —I, alkyl;

$R_{11}$=—H, —Br, —I, alkyl;

$R_{12}$=—H, —Br, —I, alkyl; and $R_{13}$=—H, —Br, —I, alkyl;

formula F

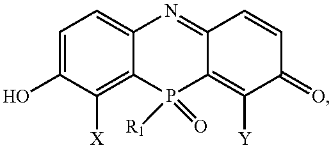

wherein;

R1 = —$CH_3$, —$CH_2CH_3$,

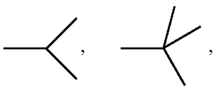
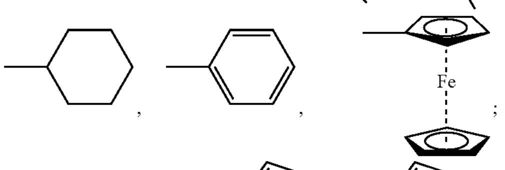

X = —Br, —I,

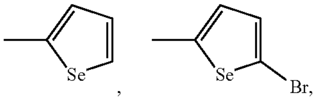
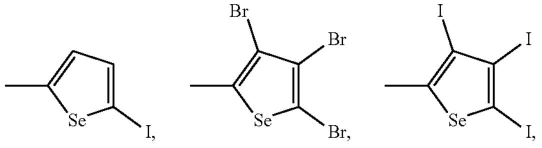

-continued

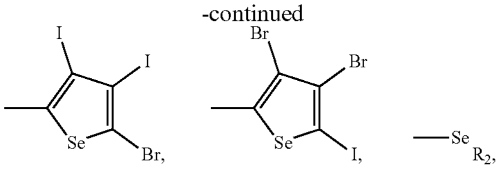
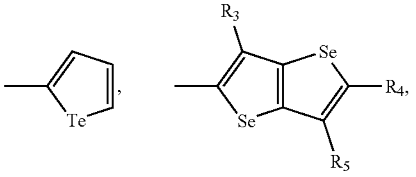
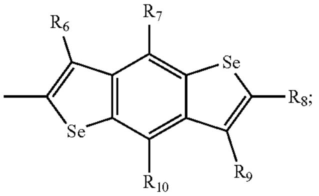

wherein $R_2$=alkyl;

$R_3$=—H, —Br, —I, alkyl;

$R_4$=—H, —Br, —I, alkyl;

$R_5$=—H, —Br, —I, alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl; and $R_{10}$=—H, —Br, —I, alkyl;

Y = —Br, —I,

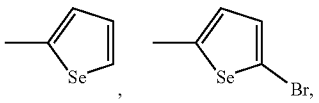
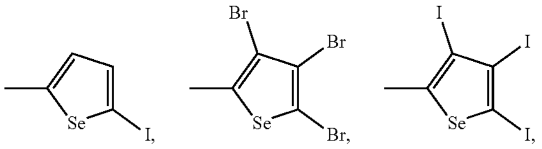
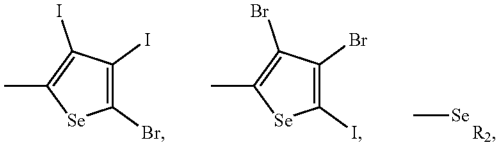
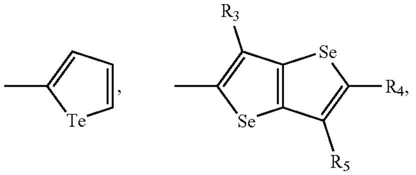
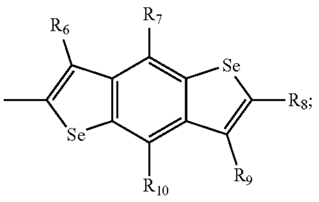

wherein $R_2$=alkyl;

$R_3$=—H, —Br, —I, alkyl;

$R_4$=—H, —Br, —I, alkyl;

$R_5$=—H, —Br, —I, alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl; and $R_{10}$=—H, —Br, —I, alkyl;

formula G

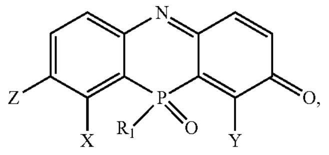

wherein

R1 is an alkyl (R);

R = —CH3, —CH2CH3, 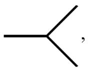, 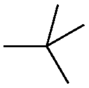, 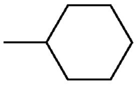, 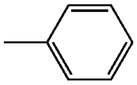, 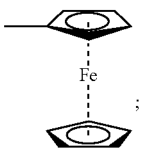;

Z = 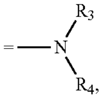, 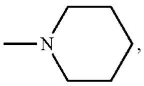, 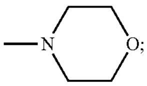;

X = —Br, —I, 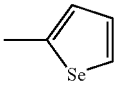, 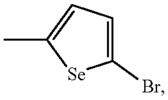 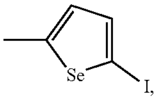 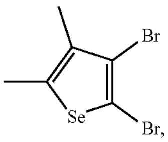 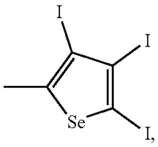 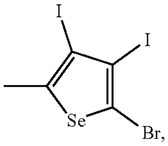 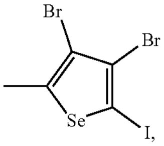 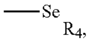 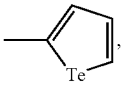, 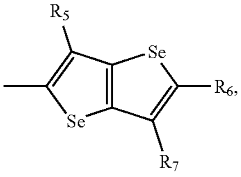

-continued

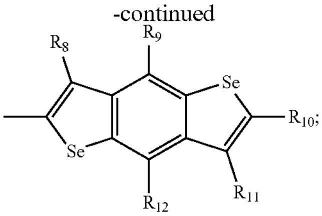

wherein $R_3$=alkyl;

$R_4$=alkyl;

$R_5$—H, —Br, —I, alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl;

$R_{10}$=—H, —Br, —I, alkyl;

$R_{11}$=—H, —Br, —I, alkyl; and $R_{12}$=—H, —Br, —I, alkyl;

Y = —Br, —I, 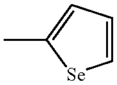, 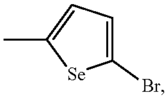 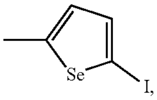 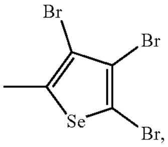 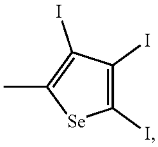 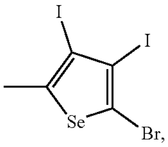 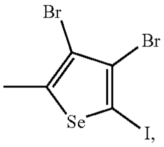 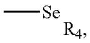 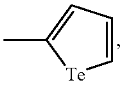, 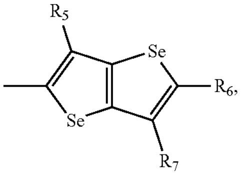 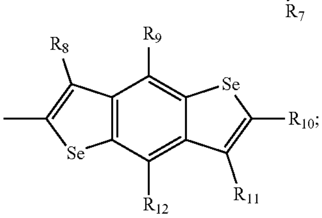

wherein $R_4$=alkyl;

$R_5$=—H, —Br, —I, alkyl;

$R_6$=—H, —Br, —I, alkyl;

$R_7$=—H, —Br, —I, alkyl;

$R_8$=—H, —Br, —I, alkyl;

$R_9$=—H, —Br, —I, alkyl;

$R_{10}$=—H, —Br, —I, alkyl;

$R_{11}$=—H, —Br, —I, alkyl; and $R_{12}$=—H, —Br, —I, alkyl.

2. The NIR absorbing photosensitizer according to claim 1, comprising one selected from the group of:
Compound 71
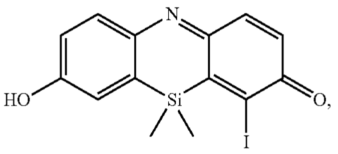
Compound 72
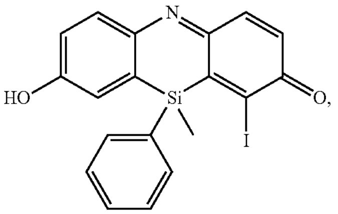
Compound 73
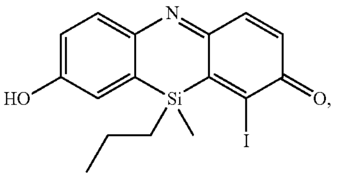
Compound 74
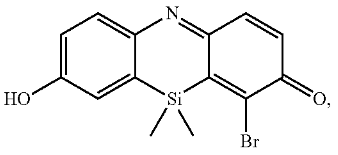
Compound 75
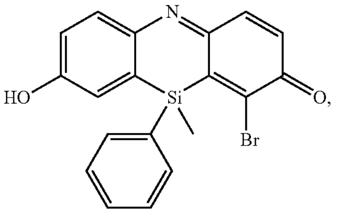
Compound 76
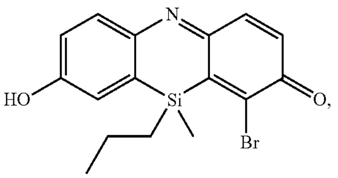
Compound 77
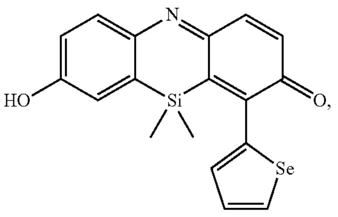
-continued
Compound 78
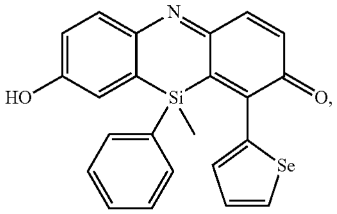
Compound 79
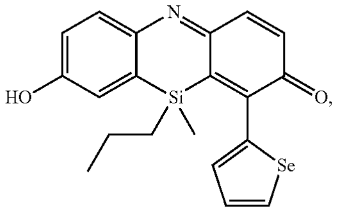
Compound 80
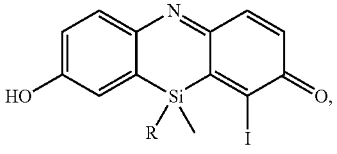
$R = -CH_2(CH_2)_{16}CH_3$
Compound 81
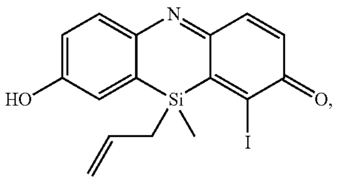
Compound 82
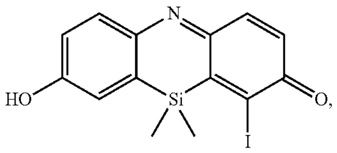
Compound 83
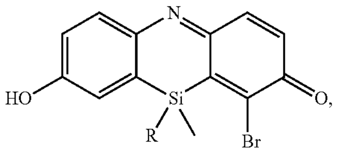
$R = -CH_2(CH_2)_{16}CH_3$
Compound 84
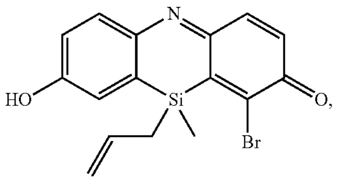
Compound 85
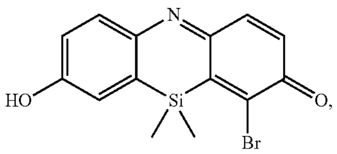

-continued
Compound 86
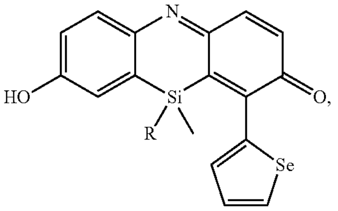
$R = -CH_2(CH_2)_{16}CH_3$
Compound 87
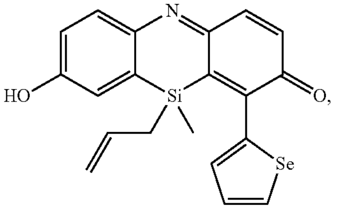
Compound 88
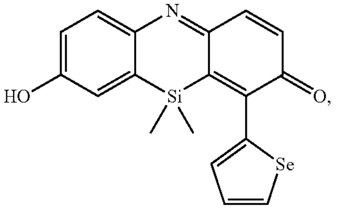
Compound 89
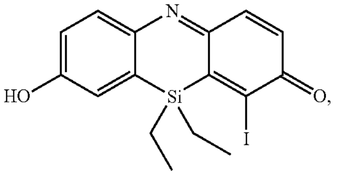
Compound 90
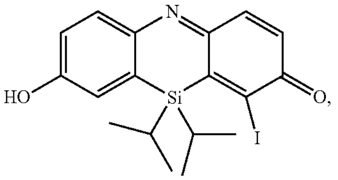
Compound 91
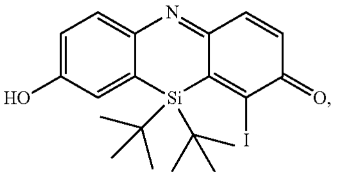
Compound 92
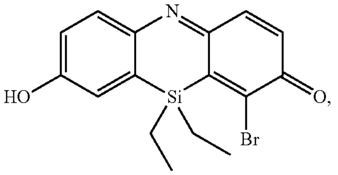
Compound 93
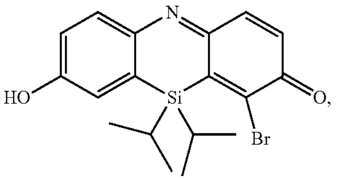
-continued
Compound 94
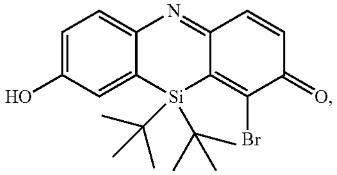
Compound 95
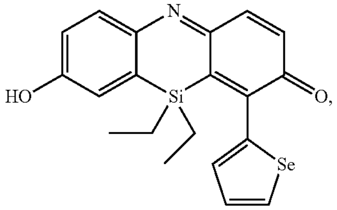
Compound 96
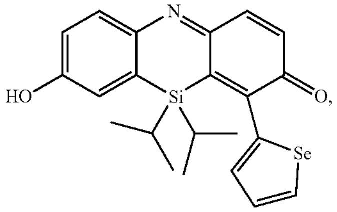
Compound 97
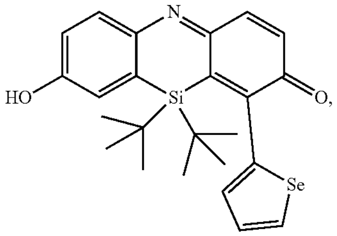
Compound 98
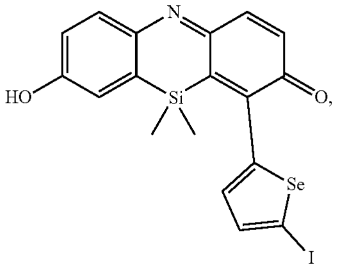
Compound 99
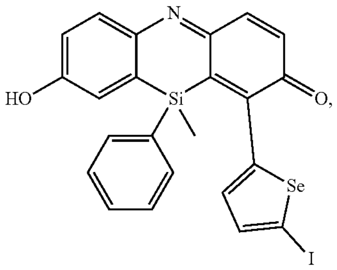

-continued
Compound 100
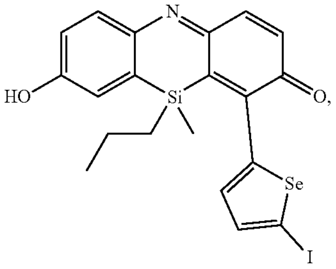
Compound 101
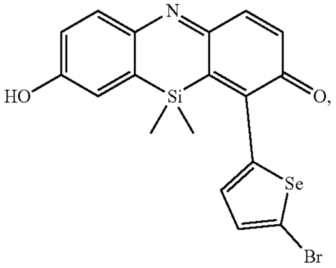
Compound 102
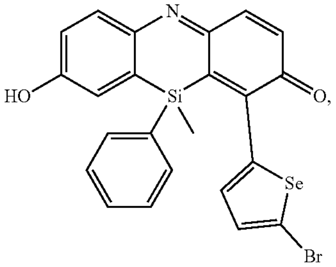
Compound 103
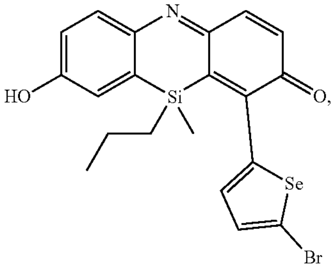
Compound 104
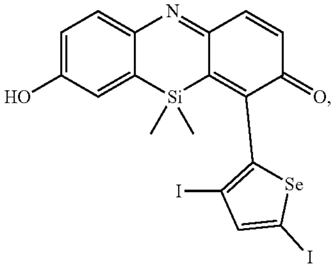
Compound 105
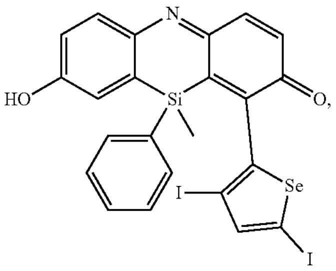
-continued
Compound 106
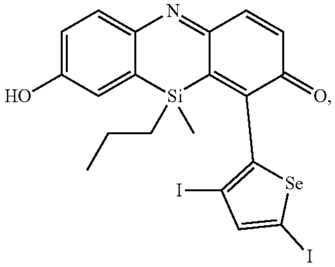
Compound 107
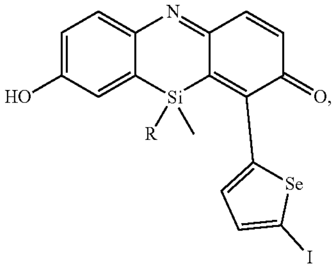
R = —$CH_2(CH_2)_{16}CH_3$
Compound 108
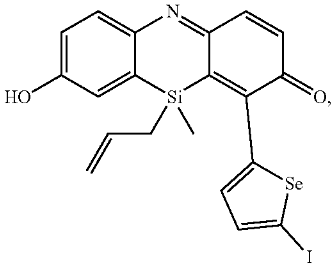
Compound 109
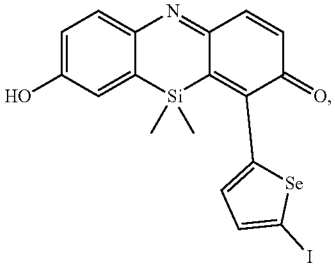
Compound 110
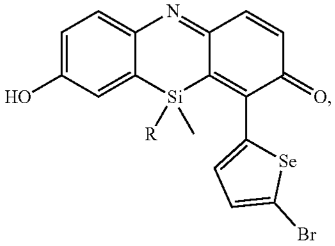
R = —$CH_2(CH_2)_{16}CH_3$ -continued
Compound 111
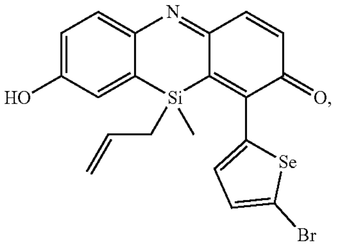
Compound 112
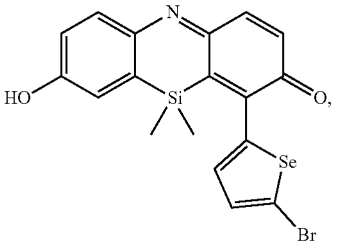
Compound 113
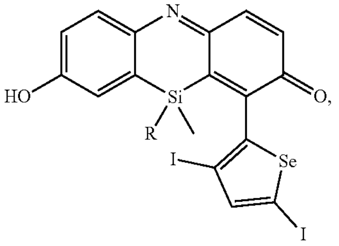
R = —$CH_2(CH_2)_{16}CH_3$
Compound 114
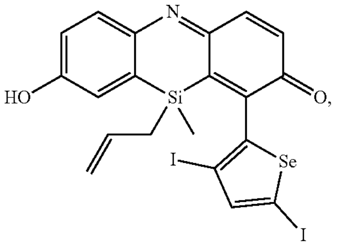
Compound 115
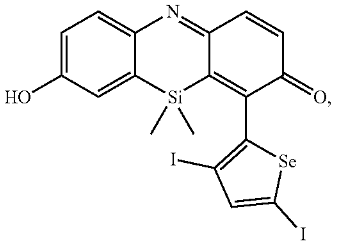
Compound 116
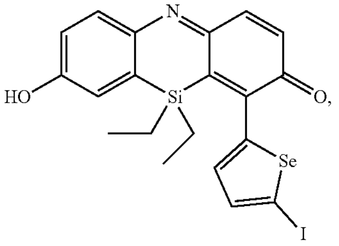
-continued
Compound 117
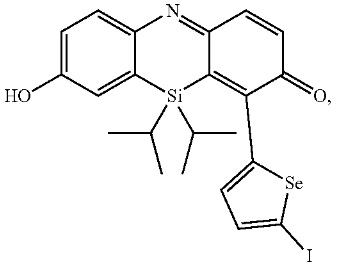
Compound 118
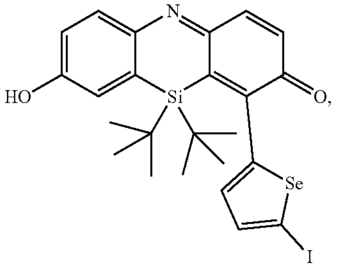
Compound 119
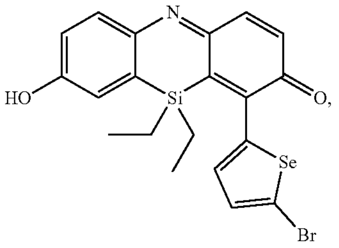
Compound 120
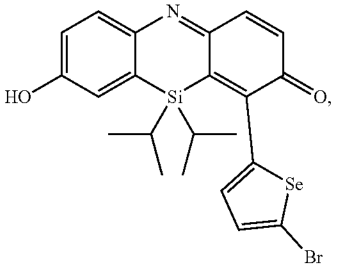
Compound 121
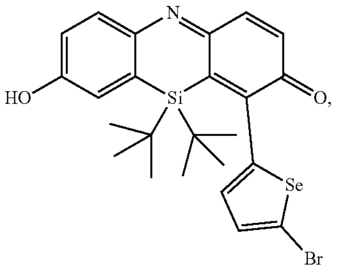
Compound 122
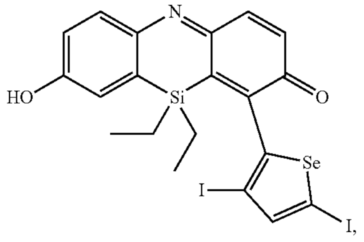

-continued
Compound 123
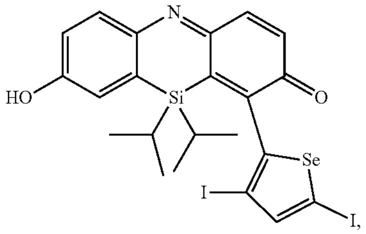
Compound 124
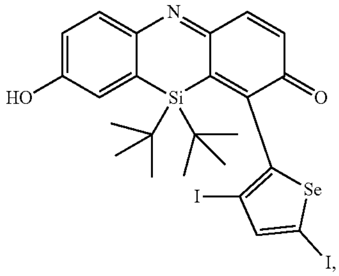
Compound 125
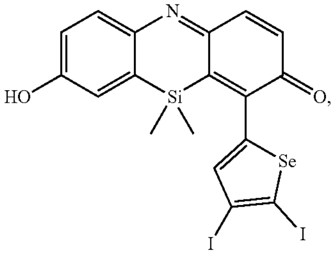
Compound 126
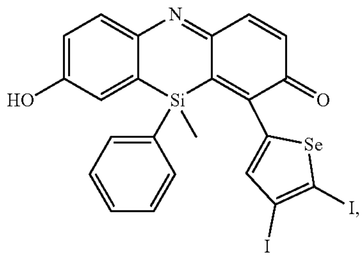
Compound 127
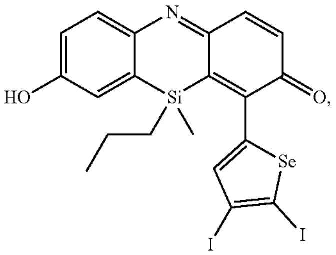
Compound 128
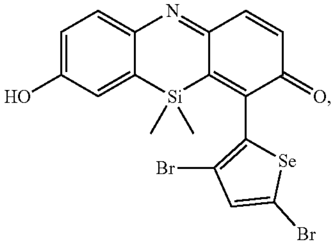
-continued
Compound 129
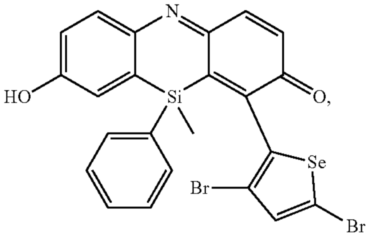
Compound 130
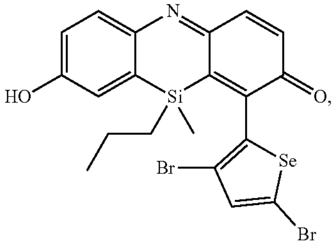
Compound 131
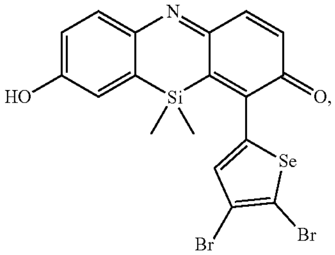
Compound 132
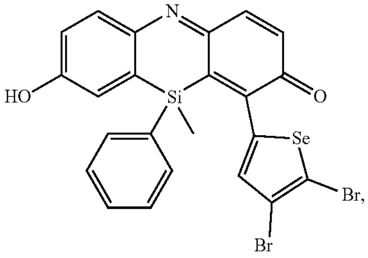
Compound 133
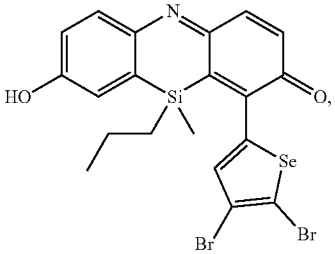
Compound 134
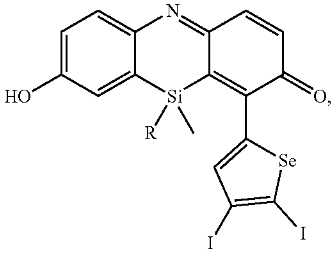
$R = -CH_2(CH_2)_{16}CH_3$ -continued
Compound 135
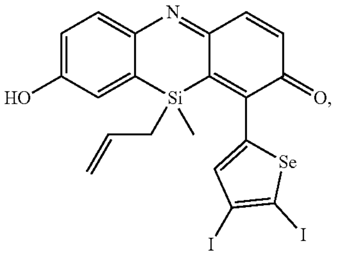
Compound 136
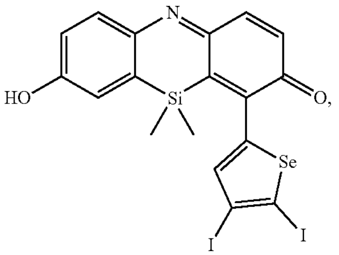
Compound 137
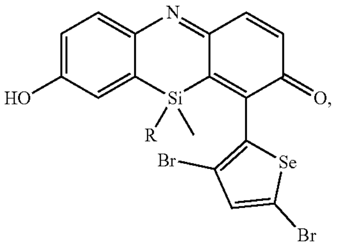
R = —$CH_2(CH_2)_{16}CH_3$
Compound 138
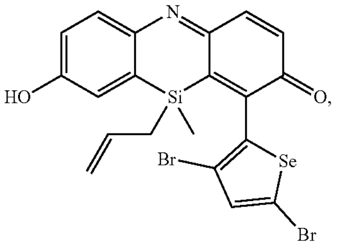
Compound 139
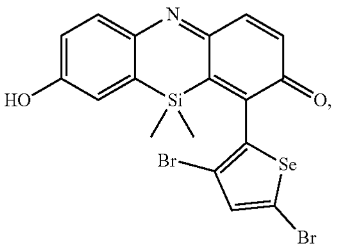
Compound 140
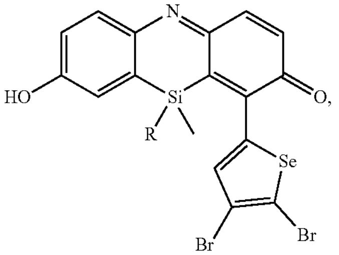
R = —$CH_2(CH_2)_{16}CH_3$
-continued
Compound 141
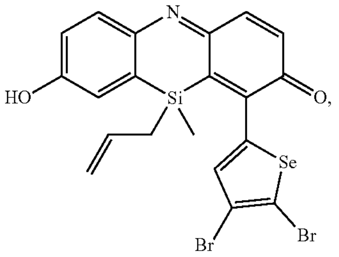
Compound 142
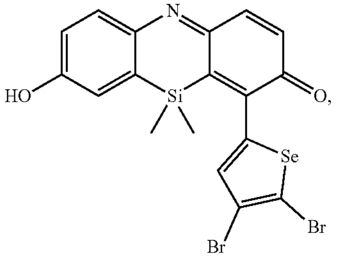
Compoud 143
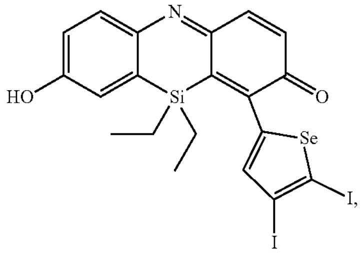
Compound 144
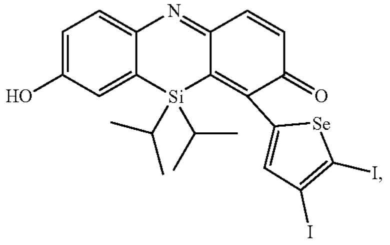
Compound 145
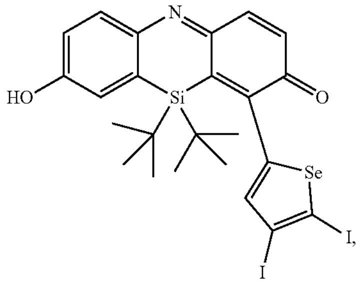
Compound 146
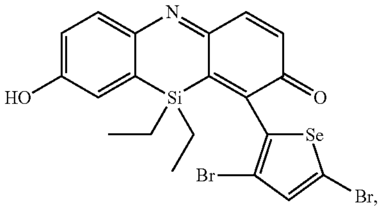

-continued
Compound 147
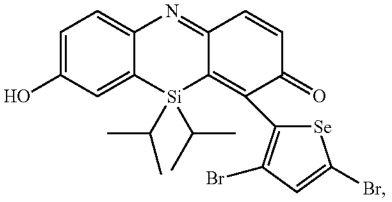
Compound 148
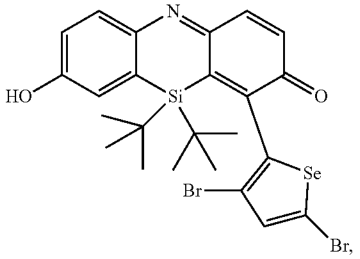
Compound 149
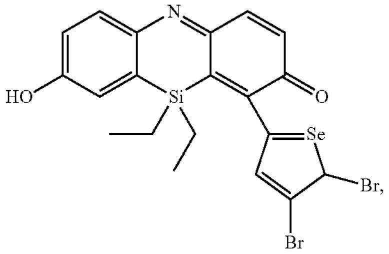
Compound 150
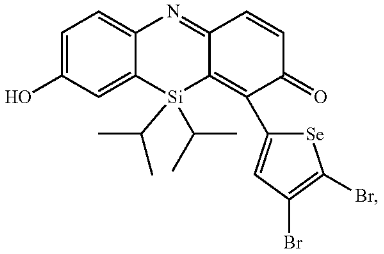
Compound 151
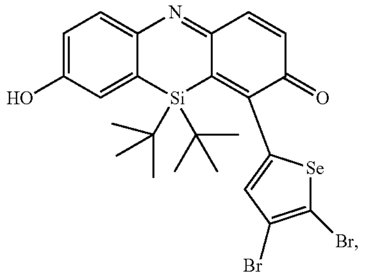
Compound 152
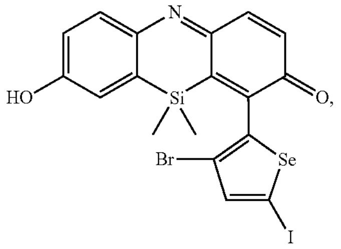
-continued
Compound 153
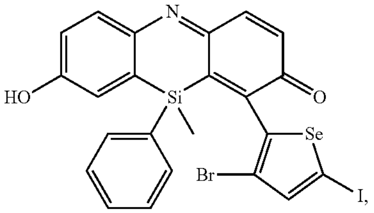
Compound 154
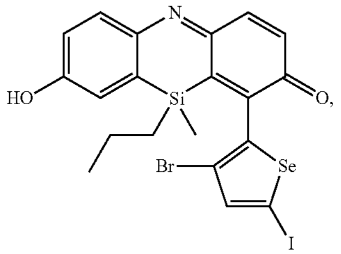
Compound 155
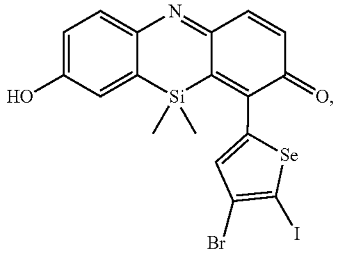
Compound 156
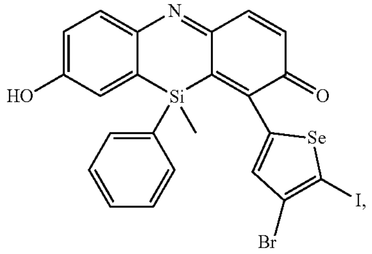
Compound 157
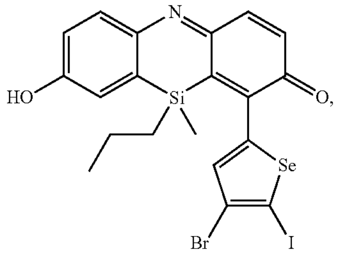
Compound 158
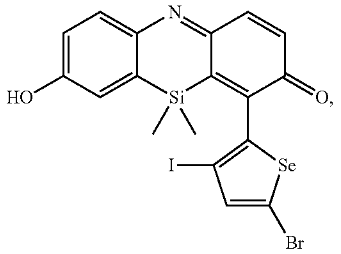

-continued
Compound 159
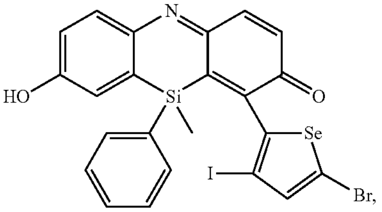
Compound 160
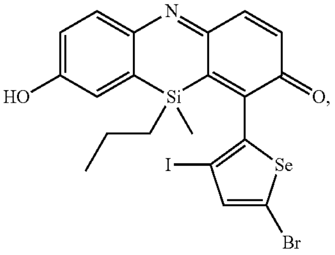
Compound 161
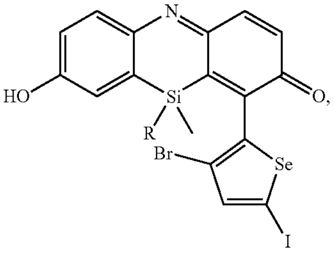
R = —$CH_2(CH_2)_{16}CH_3$
Compound 162
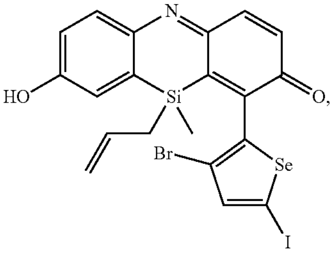
Compound 163
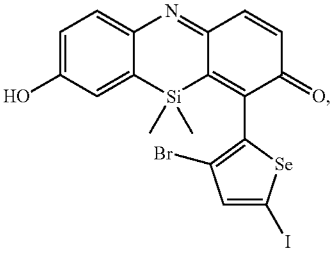
Compound 164
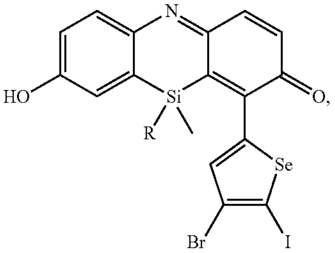
R = —$CH_2(CH_2)_{16}CH_3$
-continued
Compound 165
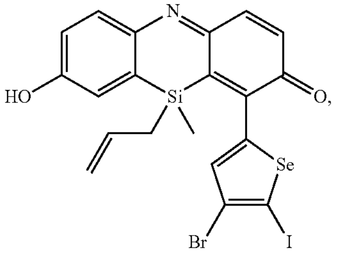
Compound 166
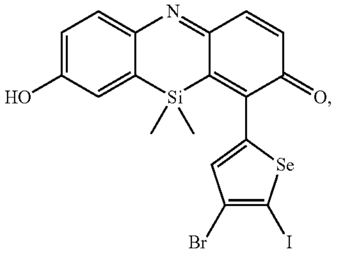
Compound 167
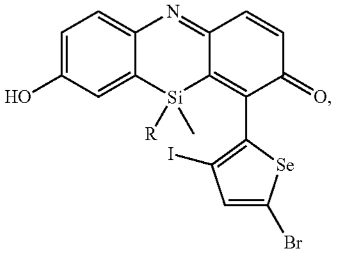
R = —$CH_2(CH_2)_{16}CH_3$
Compound 168
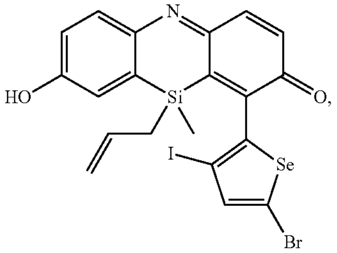
Compound 169
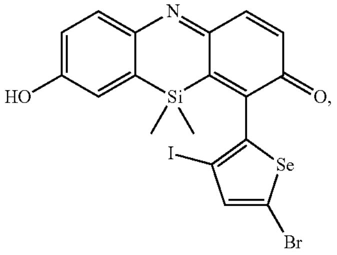
Compound 170
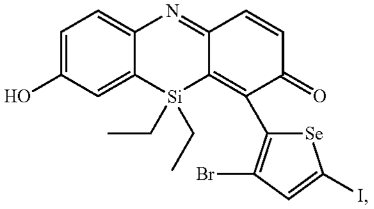

Compound 171
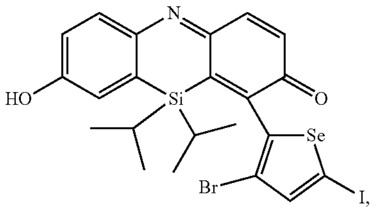
Compound 172
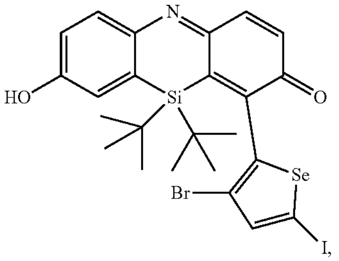
Compound 173
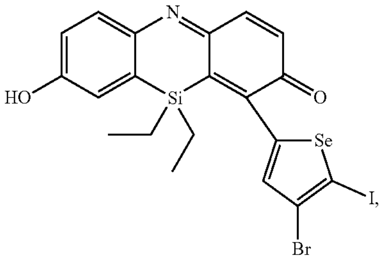
Compound 174
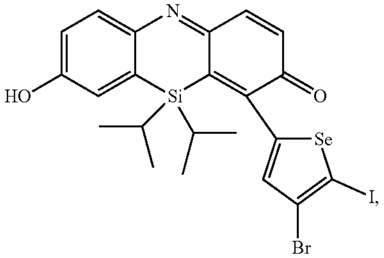
Compound 175
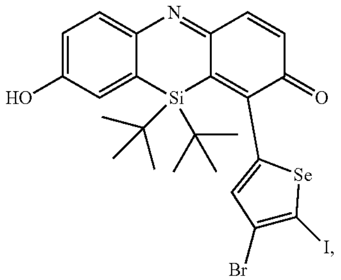
Compound 176
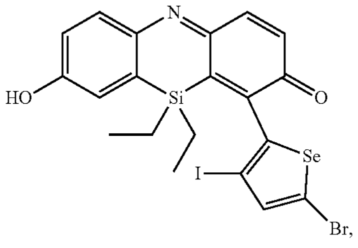
Compound 177
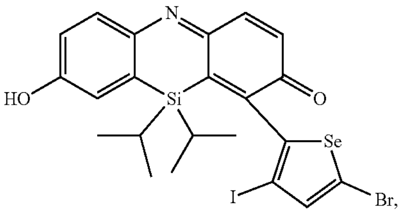
Compound 178
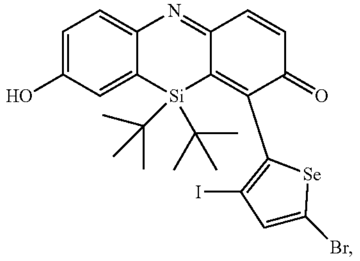
Compound 179
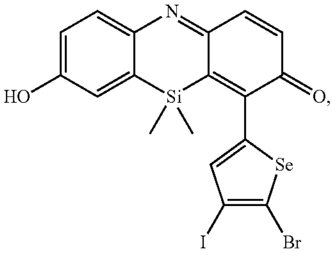
Compound 180
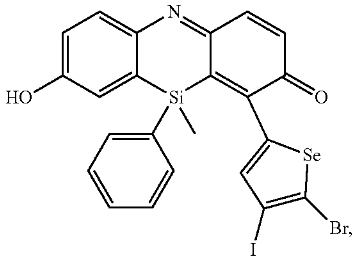
Compound 181
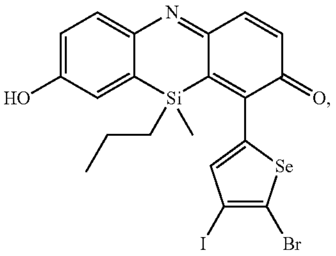
Compound 182
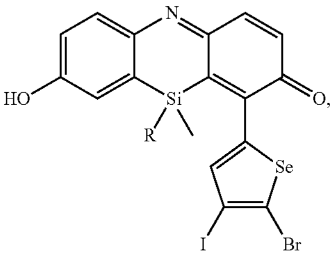
R = $-CH_2(CH_2)_{16}CH_3$ -continued
Compound 183
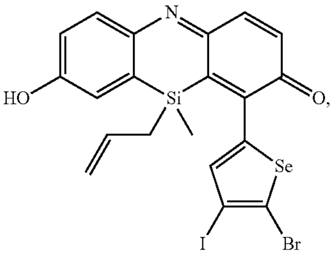
Compound 184
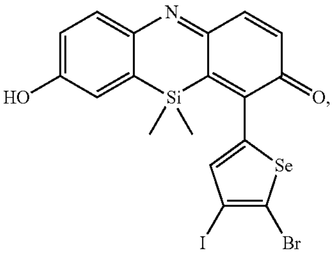
Compound 185
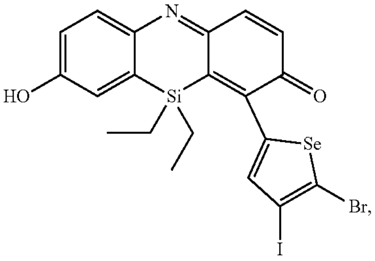
Compound 186
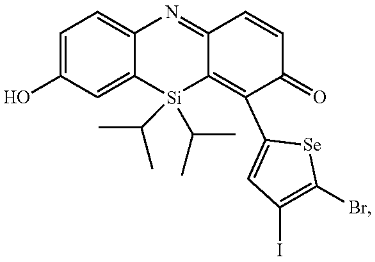
Compound 187
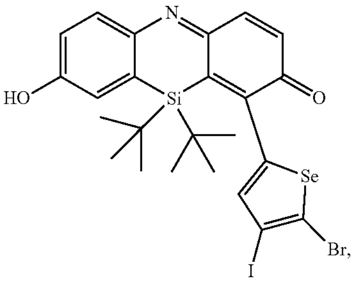
-continued
Compound 188
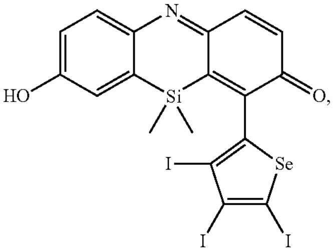
Compound 189
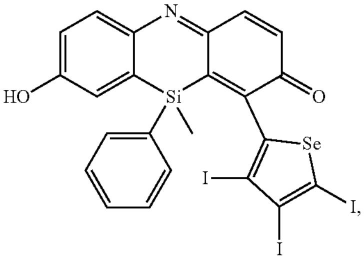
Compound 190
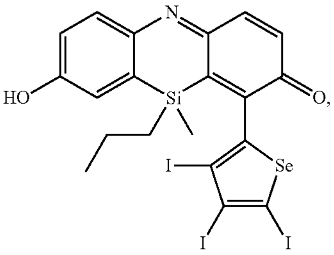
Compound 191
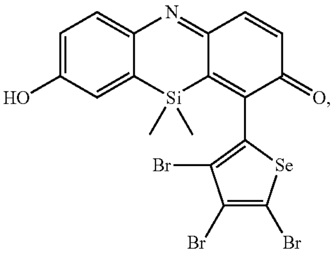
Compound 192
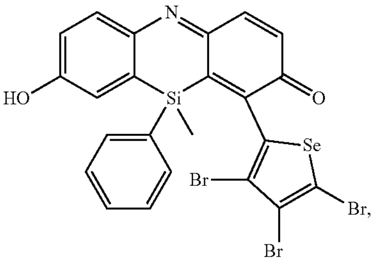
Compound 193
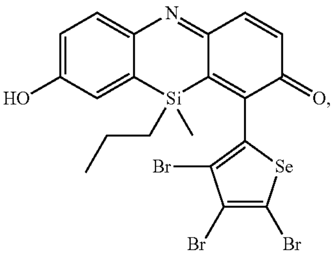

-continued
Compound 194
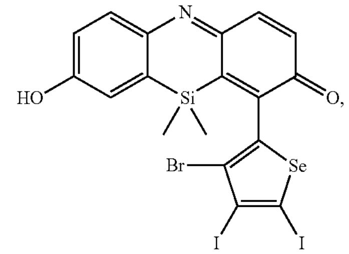
Compound 195
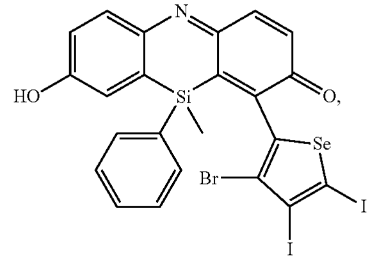
Compound 196
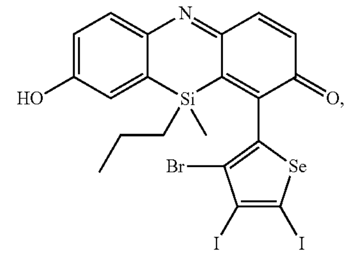
Compound 197
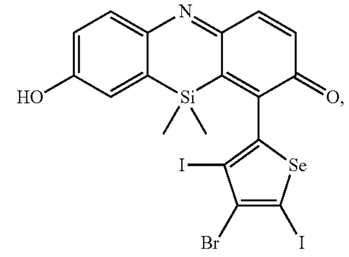
Compound 198
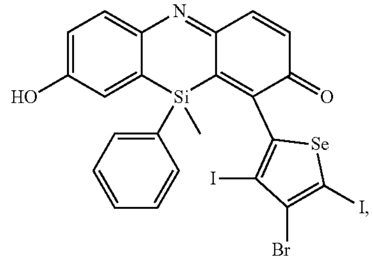
Compound 199
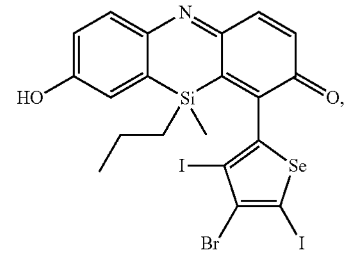
-continued
Compound 200
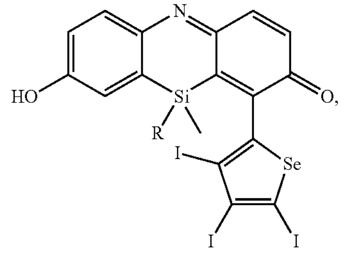
R = —$CH_2(CH_2)_{16}CH_3$
Compound 201
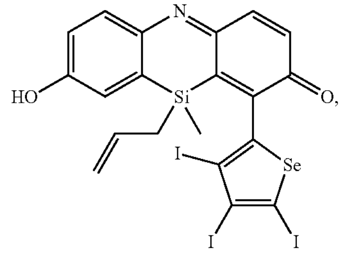
Compound 203
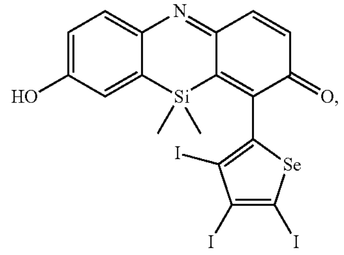
Compound 204
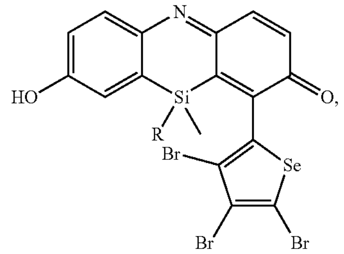
R = —$CH_2(CH_2)_{16}CH_3$
Compound 205
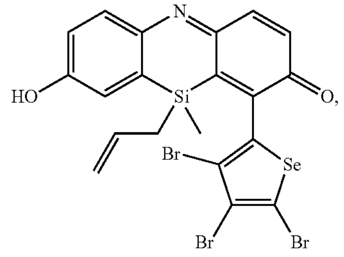

-continued
Compound 206
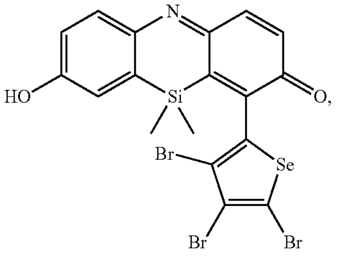
Compound 207
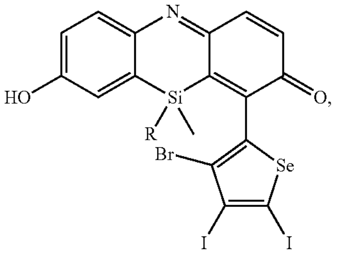
R = —— $CH_2(CH_2)_{16}CH_3$
Compound 208
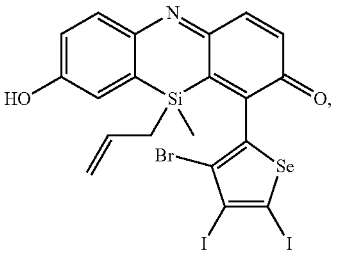
Compound 209
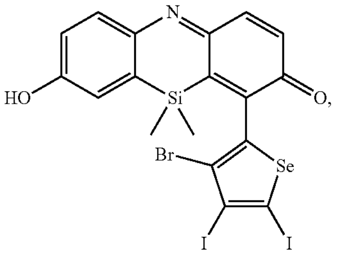
Compound 210
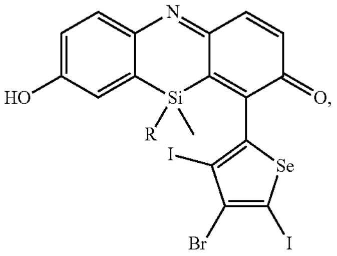
R = —— $CH_2(CH_2)_{16}CH_3$
-continued
Compound 211
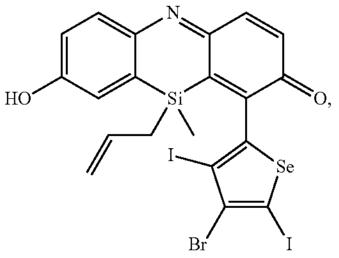
Compound 212
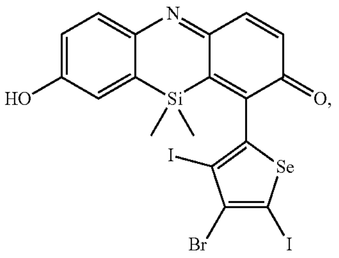
Compound 213
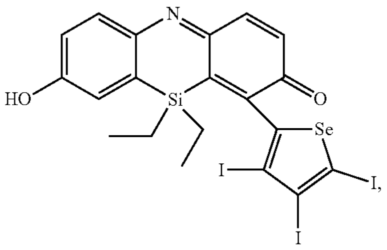
Compound 214
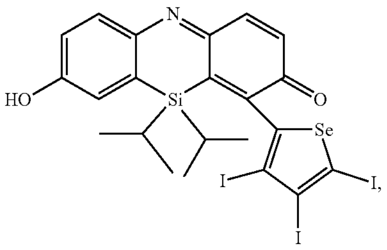
Compound 215
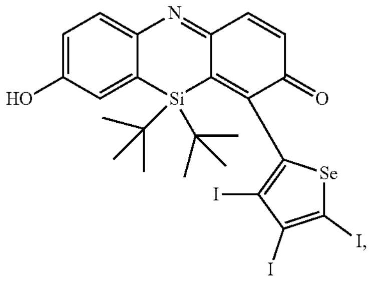

-continued
Compound 216
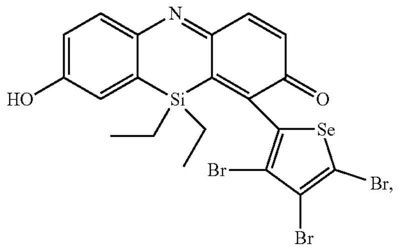
Compound 217
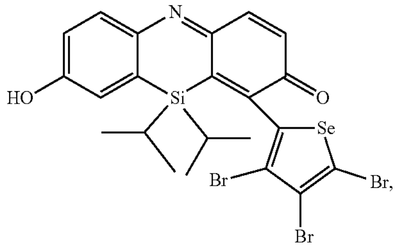
Compound 218
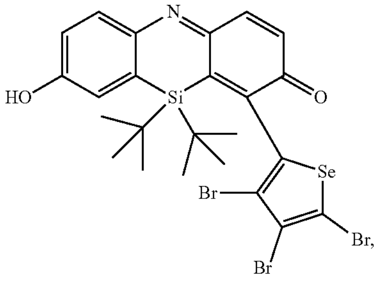
Compound 219
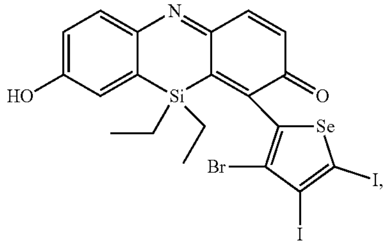
Compound 220
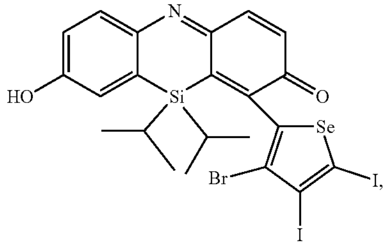
Compound 221
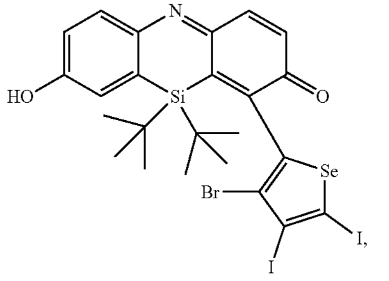
-continued
Compound 222
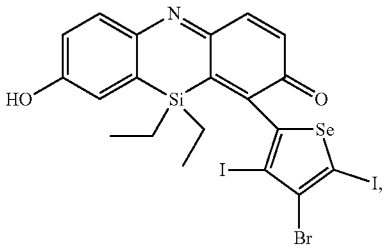
Compound 223
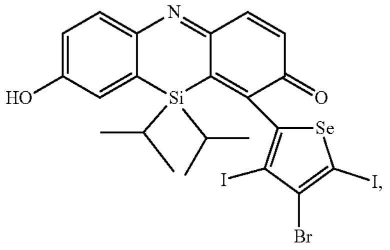
Compound 224
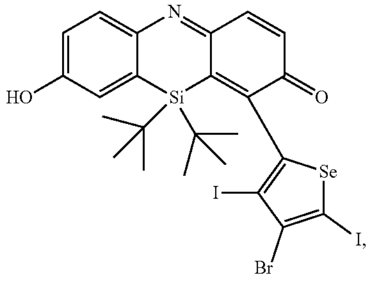
Compound 225
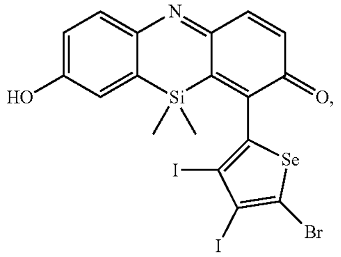
Compound 226
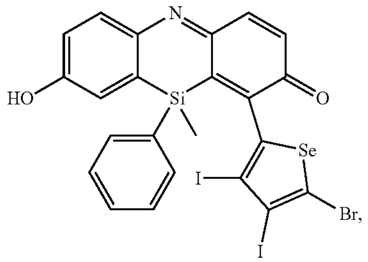
Compound 227
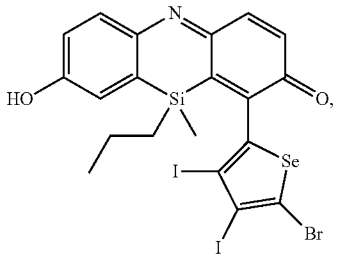

-continued
Compound 228
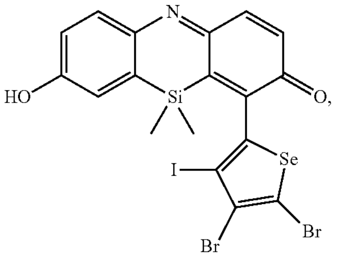
Compound 229
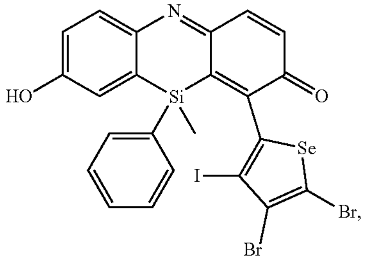
Compound 230
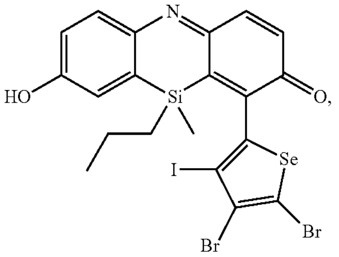
Compound 231
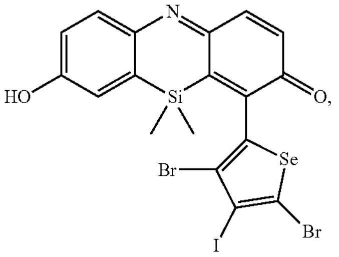
Compound 232
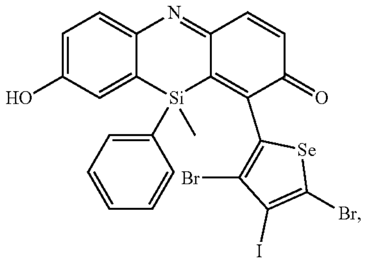
Compound 233
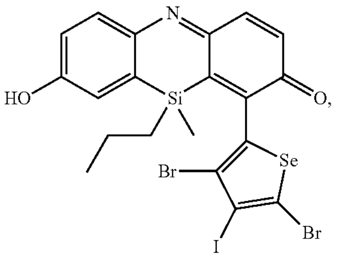
-continued
Compound 234
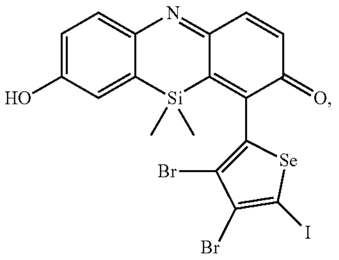
Compound 235
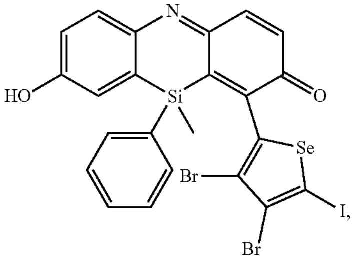
Compound 236
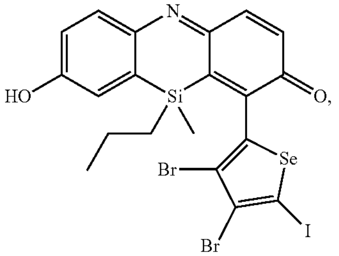
Compound 237
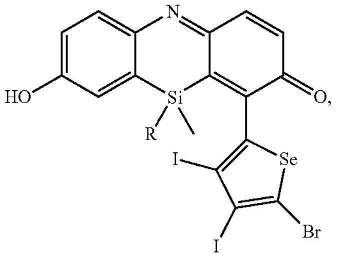
Compound 238
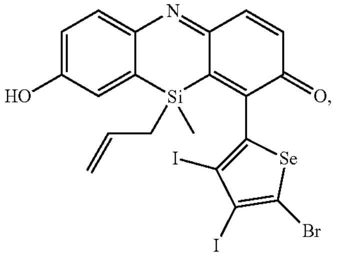
Compound 239
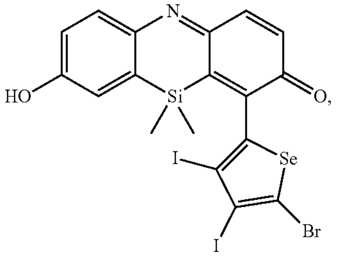

Compound 240
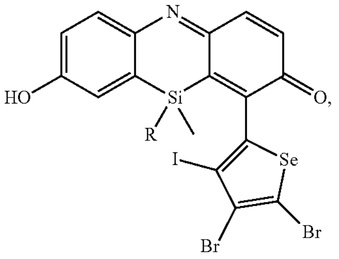
R = —$CH_2(CH_2)_{16}CH_3$
Compound 241
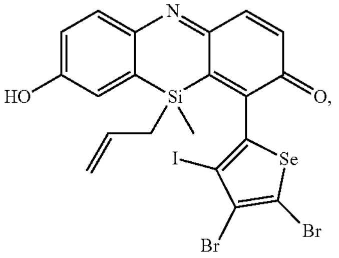
Compound 242
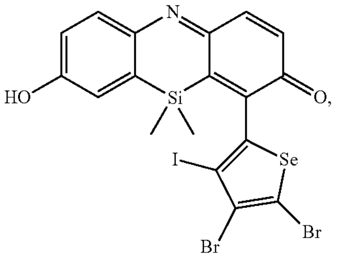
Compound 243
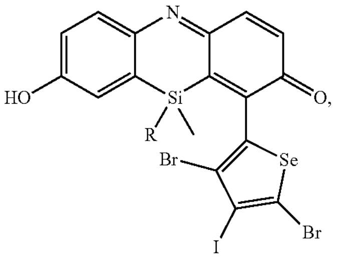
R = —$CH_2(CH_2)_{16}CH_3$
Compound 244
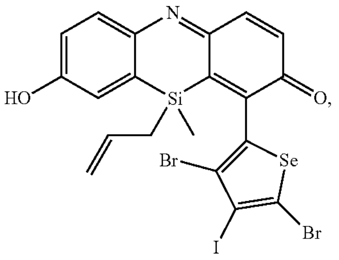
Compound 245
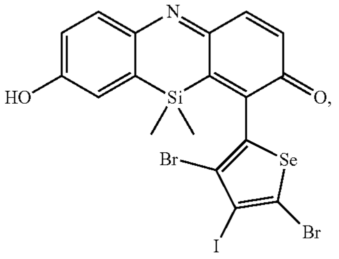
Compound 246
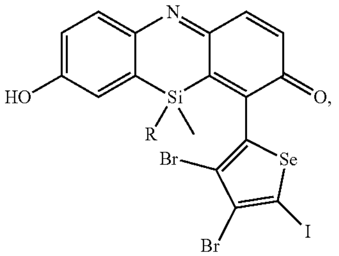
R = —$CH_2(CH_2)_{16}CH_3$
Compound 247
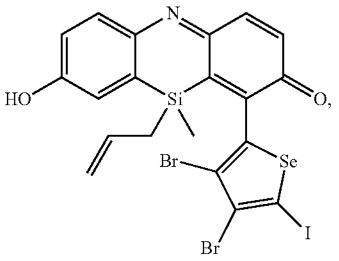
Compound 248
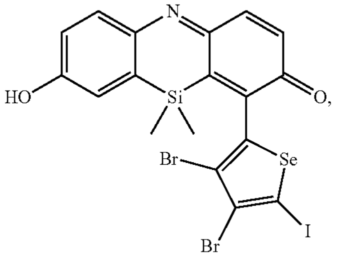
Compound 249
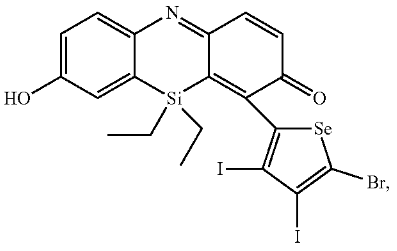
Compound 250
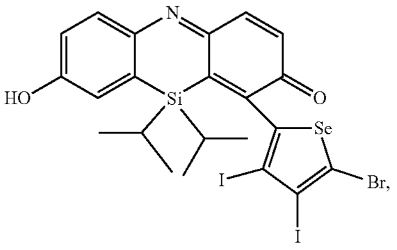

-continued
Compound 251
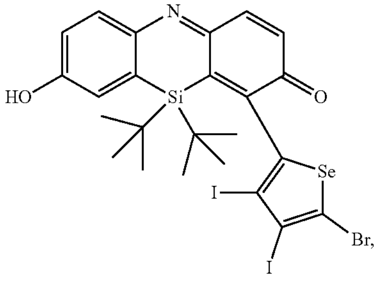
Compound 252
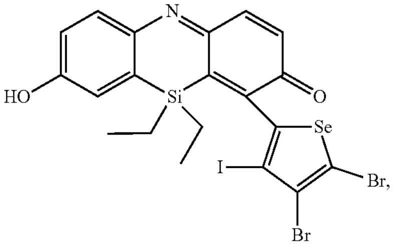
Compound 253
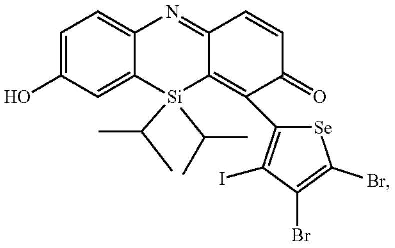
Compound 254
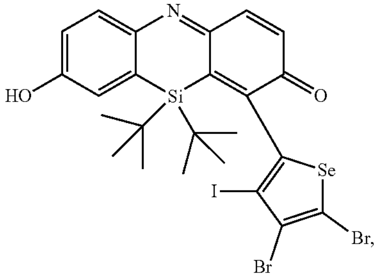
Compound 255
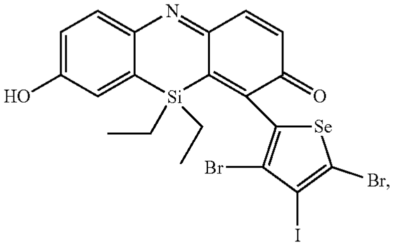
Compound 256
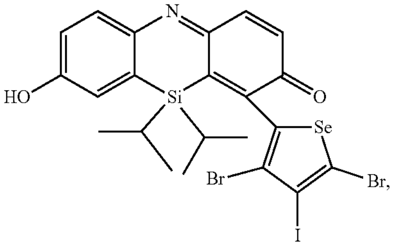
-continued
Compound 257
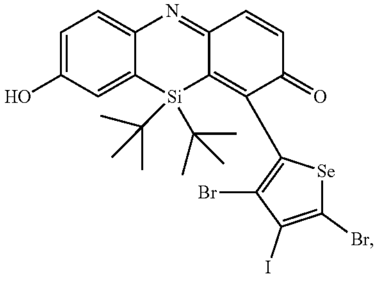
Compound 258
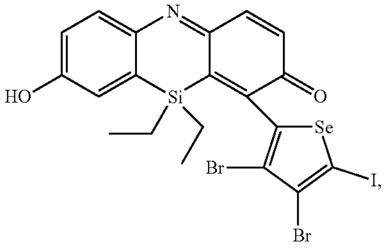
Compound 259
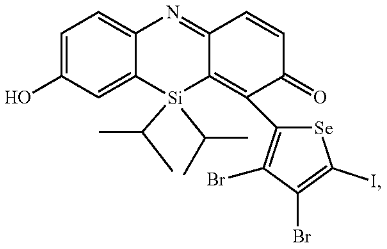
Compound 260
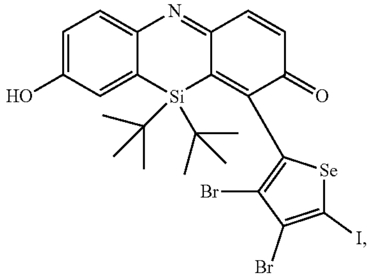
Compound 261
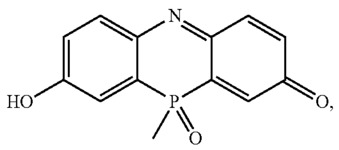
Compound 262
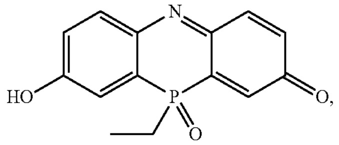

-continued

Compound 263

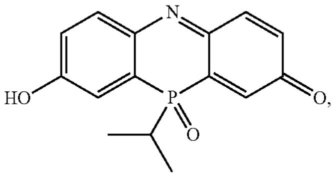

Compound 264

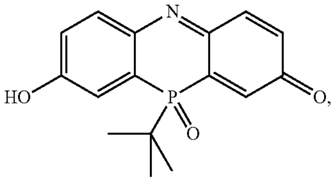

Compound 265

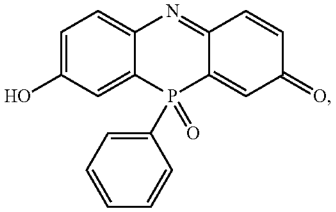

-continued

Compound 266

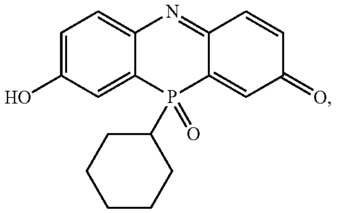

and

Compound 461

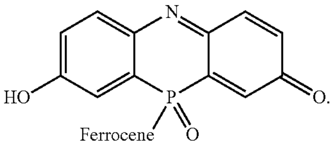

3. The NIR absorbing photosensitizer according to claim 1, wherein the NIR absorbing photosensitizer is mitochondria targeted.

4. The NIR absorbing photosensitizer according to claim 1, wherein the NIR absorbing photosensitizer is water-soluble.

5. The NIR absorbing photosensitizer according to claim 2, wherein the NIR absorbing photosensitizer is water-soluble.

6. A method of using a compound according to claim 1 for an imaging of cancer cells.

* * * * *